US010278883B2

(12) United States Patent
Walsh et al.

(10) Patent No.: US 10,278,883 B2
(45) Date of Patent: May 7, 2019

(54) SYSTEMS, METHODS, AND DEVICES FOR ASSISTING WALKING FOR DEVELOPMENTALLY-DELAYED TODDLERS

(71) Applicant: President and Fellows of Harvard College, Cambridge, MA (US)

(72) Inventors: Conor J. Walsh, Cambridge, MA (US); Eugene C. Goldfield, Sherborn, MA (US); Sang-Eun Song, Chestnut Hill, MA (US); Evelyn Park, Rolling Hills Estates, CA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 365 days.

(21) Appl. No.: 15/117,034

(22) PCT Filed: Feb. 5, 2015

(86) PCT No.: PCT/US2015/014672
§ 371 (c)(1),
(2) Date: Aug. 5, 2016

(87) PCT Pub. No.: WO2015/120186
PCT Pub. Date: Aug. 13, 2015

(65) Prior Publication Data
US 2016/0346156 A1    Dec. 1, 2016

Related U.S. Application Data

(60) Provisional application No. 61/936,162, filed on Feb. 5, 2014.

(51) Int. Cl.
*A61H 1/02*    (2006.01)
*A61H 3/00*    (2006.01)
(Continued)

(52) U.S. Cl.
CPC ............... *A61H 3/00* (2013.01); *A61H 1/024* (2013.01); *A61H 1/0244* (2013.01);
(Continued)

(58) Field of Classification Search
CPC . A61H 3/00; A61H 3/04; A61H 3/008; A61H 1/0266; A61H 1/0244; A61H 1/024;
(Continued)

(56) References Cited

U.S. PATENT DOCUMENTS 3,387,305 A    6/1968    Shafer
3,411,511 A    11/1968    Marino
(Continued)

FOREIGN PATENT DOCUMENTS

CN    1868434    11/2006
CN    202342034    7/2012
(Continued)

OTHER PUBLICATIONS

Banala, S. K. et al., "Active leg exoskeleton (alex) for gait rehabilitation of motor-impaired patients," in Proc. 2007 IEEE 10th Int. Conf. Rehabil Robotics, pp. 401-407, Jun. 2007.
(Continued)

*Primary Examiner* — Garrett K Atkinson
(74) *Attorney, Agent, or Firm* — Greenberg Traurig, LLP; David J. Dykeman; Todd C. Basile

(57) ABSTRACT

In at least some aspects, the present concepts include a method of enabling rehabilitation of bodily control of a user comprising the acts of: integrating the user within a multi-module robotic system, the multi-module robotic system comprising modules of a flexible exosuit, a support module, a mobile base, or a combination thereof, applying one or more forces, cues, or a combination thereof on the user, based on one or more subtask-specific functions of the modules, to cause a developing of one or more subtasks of (Continued)

the bodily control, and managing control of one or more remaining subtasks of the bodily control by the modules in place of at least in part, the user while applying the one or more forces, cues, or a combination thereof.

17 Claims, 19 Drawing Sheets

(51) Int. Cl.

| | | |
|---|---|---|
| A61H 3/04 | (2006.01) | |
| A63B 21/00 | (2006.01) | |
| A63B 22/00 | (2006.01) | |
| A63B 24/00 | (2006.01) | |
| A63B 26/00 | (2006.01) | |
| A63B 69/00 | (2006.01) | |
| A63B 71/00 | (2006.01) | |
| A63B 71/02 | (2006.01) | |
| A63B 71/06 | (2006.01) | |
| G09B 19/00 | (2006.01) | |
| A63B 21/005 | (2006.01) | |

(52) U.S. Cl.
CPC ........... *A61H 1/0266* (2013.01); *A61H 3/008* (2013.01); *A61H 3/04* (2013.01); *A63B 21/0058* (2013.01); *A63B 21/00178* (2013.01); *A63B 21/00181* (2013.01); *A63B 21/152* (2013.01); *A63B 21/4009* (2015.10); *A63B 21/4025* (2015.10); *A63B 24/0087* (2013.01); *A63B 26/003* (2013.01); *A63B 69/0064* (2013.01); *A63B 71/0054* (2013.01); *G09B 19/003* (2013.01); *A61H 1/0277* (2013.01); *A61H 2003/043* (2013.01); *A61H 2201/0107* (2013.01); *A61H 2201/123* (2013.01); *A61H 2201/1238* (2013.01); *A61H 2201/5007* (2013.01); *A61H 2201/5061* (2013.01); *A61H 2201/5064* (2013.01); *A61H 2201/5069* (2013.01); *A61H 2201/5071* (2013.01); *A61H 2201/5084* (2013.01); *A61H 2201/5097* (2013.01); *A63B 21/157* (2013.01); *A63B 2022/0092* (2013.01); *A63B 2024/0093* (2013.01); *A63B 2071/0072* (2013.01); *A63B 2071/025* (2013.01); *A63B 2071/0655* (2013.01); *A63B 2220/16* (2013.01); *A63B 2220/40* (2013.01); *A63B 2220/51* (2013.01); *A63B 2220/803* (2013.01); *A63B 2220/89* (2013.01); *A63B 2225/20* (2013.01); *A63B 2225/50* (2013.01)

(58) Field of Classification Search
CPC .... A61H 2201/1238; A61H 2201/5061; A61H 2201/5097; A61H 2201/5007; A61H 2003/043; A61H 2201/5064; A61H 2201/0107; A61H 2201/123; A61H 2201/5069; A61H 2201/5084; A61H 1/0277; A61H 2201/5071; A63B 21/00181; A63B 21/4009; A63B 69/0064; A63B 21/4025; A63B 24/0087; A63B 21/0058; A63B 71/0054; A63B 21/152; A63B 21/00178; A63B 26/003; A63B 21/157; A63B 2024/0093; A63B 2220/803; A63B 2220/51; A63B 2071/0072; A63B 2220/16; A63B 2225/50; A63B 2071/025; A63B 2220/89; A63B 2225/20; A63B 2071/0655; A63B 2220/40; A63B 2022/0092; G09B 19/003
See application file for complete search history.

(56) References Cited

U.S. PATENT DOCUMENTS

| | | | |
|---|---|---|---|
| 3,831,467 A | 8/1974 | Moore | |
| 4,023,215 A | 5/1977 | Moore | |
| 4,252,112 A | 2/1981 | Joyce | |
| 4,370,977 A | 2/1983 | Mauldin et al. | |
| 4,682,776 A | 7/1987 | Mitchell et al. | |
| 4,697,808 A | 10/1987 | Larson et al. | |
| 4,724,827 A * | 2/1988 | Schenck | A61H 1/0288 601/40 |
| 4,760,850 A | 8/1988 | Phillips et al. | |
| 5,020,790 A | 6/1991 | Beard et al. | |
| 5,282,460 A | 2/1994 | Boldt | |
| 5,584,799 A | 12/1996 | Gray | |
| 5,667,461 A * | 9/1997 | Hall | A61H 1/0229 472/15 |
| 5,865,714 A | 2/1999 | Marlowe | |
| 5,865,770 A | 2/1999 | Schectman | |
| 6,123,649 A * | 9/2000 | Lee | A63B 21/153 482/51 |
| 6,129,691 A | 10/2000 | Ruppert | |
| 6,168,634 B1 | 1/2001 | Schmitz | |
| 6,213,922 B1 | 4/2001 | Afanasenko et al. | |
| 6,500,138 B1 | 12/2002 | Irby et al. | |
| 6,517,503 B1 | 2/2003 | Naft et al. | |
| 6,633,783 B1 | 10/2003 | Dariush et al. | |
| 6,635,024 B2 | 10/2003 | Hatton et al. | |
| 6,666,831 B1 * | 12/2003 | Edgerton | A61H 1/0237 600/587 |
| 6,689,075 B2 | 2/2004 | West | |
| 6,741,911 B2 | 5/2004 | Simmons | |
| 6,783,555 B2 | 8/2004 | Kuhn et al. | |
| 6,790,165 B2 | 9/2004 | Huang | |
| 6,796,926 B2 * | 9/2004 | Reinkensmeyer | A61B 5/1038 482/51 |
| 6,812,624 B1 | 11/2004 | Pei et al. | |
| 6,955,692 B2 | 10/2005 | Grundei | |
| 6,989,669 B2 | 1/2006 | Low et al. | |
| 7,034,432 B1 | 4/2006 | Pelrine et al. | |
| 7,034,527 B2 | 4/2006 | Low et al. | |
| 7,049,732 B2 | 5/2006 | Pei et al. | |
| 7,056,297 B2 | 6/2006 | Dohnu et al. | |
| 7,064,472 B2 | 6/2006 | Pelrine et al. | |
| 7,090,650 B2 | 8/2006 | Ou et al. | |
| 7,153,242 B2 | 12/2006 | Goffer | |
| 7,153,246 B2 | 12/2006 | Koscielny et al. | |
| 7,166,953 B2 | 1/2007 | Heim et al. | |
| 7,190,141 B1 | 3/2007 | Ashrafiuon et al. | |
| 7,199,501 B2 | 4/2007 | Pei et al. | |
| 7,211,937 B2 | 5/2007 | Kornbluh et al. | |
| 7,224,106 B2 | 5/2007 | Pei et al. | |
| 7,229,390 B2 | 6/2007 | Fujii et al. | |
| 7,233,097 B2 | 6/2007 | Rosenthal et al. | |
| 7,252,644 B2 | 8/2007 | Dewald et al. | |
| 7,259,503 B2 | 8/2007 | Pei et al. | |
| 7,259,553 B2 | 8/2007 | Arns, Jr. et al. | |
| 7,307,418 B2 | 12/2007 | Low et al. | |
| 7,331,906 B2 * | 2/2008 | He | A61H 1/0237 482/69 |
| 7,341,295 B1 | 3/2008 | Veatch et al. | |
| 7,367,958 B2 | 5/2008 | McBean et al. | |
| 7,368,862 B2 | 5/2008 | Pelrine et al. | |
| 7,378,878 B2 | 5/2008 | Pelrine et al. | |
| 7,390,309 B2 | 6/2008 | Dariush | |
| 7,410,471 B1 | 8/2008 | Campbell et al. | |
| 7,411,332 B2 | 8/2008 | Kornbluh et al. | |
| 7,429,253 B2 | 9/2008 | Shimada et al. | |
| 7,436,099 B2 | 10/2008 | Pei et al. | |
| 7,445,606 B2 | 11/2008 | Rastegar et al. | |
| 7,456,549 B2 | 11/2008 | Heim et al. | |
| 7,476,185 B2 | 1/2009 | Drennan | |
| 7,494,450 B2 * | 2/2009 | Solomon | A61H 1/0229 482/51 |
| 7,521,840 B2 | 4/2009 | Heim | |
| 7,521,847 B2 | 4/2009 | Heim | |
| 7,537,573 B2 | 5/2009 | Horst | |

(56) References Cited

U.S. PATENT DOCUMENTS

| | | |
|---|---|---|
| 7,549,969 B2 | 6/2009 | van den Bogert |
| 7,567,681 B2 | 7/2009 | Pelrine et al. |
| 7,578,799 B2 | 8/2009 | Thorsteinsson et al. |
| 7,595,580 B2 | 9/2009 | Heim |
| 7,598,651 B2 | 10/2009 | Kornbluh et al. |
| 7,598,652 B2 | 10/2009 | Kornbluh et al. |
| 7,626,319 B2 | 12/2009 | Heim |
| 7,650,204 B2 | 1/2010 | Dariush |
| 7,652,386 B2 | 1/2010 | Donelan et al. |
| 7,654,973 B2 | 2/2010 | Firsov |
| 7,679,267 B2 | 3/2010 | Heim |
| 7,684,896 B2 | 3/2010 | Dariush |
| 7,705,521 B2 | 4/2010 | Pelrine et al. |
| 7,737,685 B2 | 6/2010 | Low et al. |
| 7,750,532 B2 | 7/2010 | Heim |
| 7,758,481 B2 | 7/2010 | Drennan |
| 7,774,177 B2 | 8/2010 | Dariush |
| 7,775,999 B2 | 8/2010 | Brown |
| 7,785,279 B2 | 8/2010 | Sankai |
| 7,785,656 B2 | 8/2010 | Pei et al. |
| 7,787,646 B2 | 8/2010 | Pelrine et al. |
| 7,804,227 B2 | 9/2010 | Pelrine et al. |
| 7,857,774 B2 | 12/2010 | Sankai |
| 7,860,562 B2 | 12/2010 | Endo et al. |
| 7,883,546 B2 | 2/2011 | Kazerooni et al. |
| 7,887,471 B2 * | 2/2011 | McSorley .......... A63B 21/0552 |
| | | 482/136 |
| 7,897,168 B2 | 3/2011 | Chen et al. |
| 7,911,761 B2 | 3/2011 | Biggs et al. |
| 7,915,790 B2 | 3/2011 | Heim et al. |
| 7,918,808 B2 | 4/2011 | Simmons |
| 7,921,541 B2 | 4/2011 | Pei et al. |
| 7,923,064 B2 | 4/2011 | Pelrien et al. |
| 7,923,902 B2 | 4/2011 | Heim |
| 7,947,004 B2 | 5/2011 | Kazerooni et al. |
| 7,952,261 B2 | 5/2011 | Lipton et al. |
| 7,985,193 B2 | 6/2011 | Thorsteinsson et al. |
| 7,977,923 B2 | 7/2011 | Pelrine et al. |
| 7,981,508 B1 | 7/2011 | Sharma et al. |
| 7,990,022 B2 | 8/2011 | Heim |
| 7,998,040 B2 * | 8/2011 | Kram ................ A63B 21/4015 |
| | | 482/124 |
| 8,048,007 B2 | 11/2011 | Roy |
| 8,057,410 B2 * | 11/2011 | Angold .................... A61H 3/00 |
| | | 601/35 |
| 8,058,861 B2 | 11/2011 | Pelrine et al. |
| 8,075,633 B2 | 12/2011 | Herr et al. |
| 8,083,644 B2 | 12/2011 | Purdy et al. |
| 8,096,965 B2 | 1/2012 | Goffer et al. |
| 8,114,034 B2 | 2/2012 | Ikeuchi et al. |
| 8,125,755 B2 | 2/2012 | Garcia et al. |
| 8,127,437 B2 | 3/2012 | Lipton et al. |
| 8,142,370 B2 | 3/2012 | Weinberg et al. |
| 8,147,436 B2 | 4/2012 | Agrawal et al. |
| 8,164,232 B2 | 4/2012 | Kornbluh et al. |
| 8,183,739 B2 | 5/2012 | Heim |
| 8,222,799 B2 | 7/2012 | Polyakov et al. |
| 8,231,687 B2 | 7/2012 | Bedard et al. |
| 8,235,869 B2 | 8/2012 | Rastegar et al. |
| 8,246,559 B2 | 8/2012 | Hoffman et al. |
| 8,248,750 B2 | 8/2012 | Biggs et al. |
| 8,274,244 B2 | 9/2012 | Bhugra et al. |
| 8,283,839 B2 | 10/2012 | Heim |
| 8,287,477 B1 | 10/2012 | Herr et al. |
| 8,292,836 B2 | 10/2012 | Matsuoka et al. |
| 8,299,634 B2 | 10/2012 | Donelan et al. |
| 8,311,623 B2 | 11/2012 | Sanger |
| 8,316,526 B2 | 11/2012 | Pei et al. |
| 8,316,719 B2 | 11/2012 | Majidi et al. |
| 8,323,355 B2 | 12/2012 | Latour |
| 8,325,458 B2 | 12/2012 | Prahlad et al. |
| 8,348,875 B2 | 1/2013 | Goffer et al. |
| 8,376,971 B1 | 2/2013 | Herr et al. |
| 8,409,117 B2 | 4/2013 | Cheng et al. |
| 8,436,508 B2 | 5/2013 | Kornbluh et al. |
| 8,438,757 B2 | 5/2013 | Roser |
| 8,467,904 B2 | 6/2013 | Dariush |
| 8,488,295 B2 | 7/2013 | Garcia et al. |
| 8,508,109 B2 | 8/2013 | Pelrine et al. |
| 8,551,029 B1 | 10/2013 | Herr et al. |
| 8,551,184 B1 | 10/2013 | Herr |
| 8,562,691 B2 | 10/2013 | Endo et al. |
| 8,564,926 B2 | 10/2013 | Prahlad et al. |
| 8,585,620 B2 | 11/2013 | McBean et al. |
| 8,597,369 B2 | 12/2013 | Hansen et al. |
| 8,608,479 B2 * | 12/2013 | Liu ........................ A61H 1/024 |
| | | 434/255 |
| 8,608,674 B2 | 12/2013 | Krebs et al. |
| 8,622,938 B2 | 1/2014 | Sankai |
| 8,663,133 B2 | 3/2014 | Johnson et al. |
| 8,665,578 B2 | 3/2014 | Pelrine et al. |
| 8,679,575 B2 | 3/2014 | Biggs et al. |
| 8,766,925 B2 | 6/2014 | Perlin et al. |
| 8,764,850 B2 | 7/2014 | Hansen et al. |
| 8,773,148 B2 | 7/2014 | Sankai et al. |
| 8,847,611 B2 | 9/2014 | Ulmen et al. |
| 8,905,955 B2 | 12/2014 | Goffer et al. |
| 8,920,517 B2 | 12/2014 | Smith et al. |
| 8,926,534 B2 | 1/2015 | McBean et al. |
| 8,938,289 B2 | 1/2015 | Einav et al. |
| 8,961,439 B2 | 2/2015 | Yang et al. |
| 8,975,888 B2 | 3/2015 | Pelrine et al. |
| 8,981,621 B2 | 3/2015 | Pelrine et al. |
| 8,986,233 B2 | 3/2015 | Aoki et al. |
| 9,044,346 B2 | 6/2015 | Langlois et al. |
| 9,072,941 B2 | 7/2015 | Duda et al. |
| 9,101,323 B2 | 8/2015 | Einarsson et al. |
| 9,144,528 B2 | 9/2015 | Agrawal et al. |
| 9,149,370 B2 | 10/2015 | Herr et al. |
| 9,195,794 B2 | 11/2015 | Dariush |
| 9,198,821 B2 | 12/2015 | Unluhisarcikli et al. |
| 9,221,177 B2 | 12/2015 | Herr et al. |
| 9,228,822 B2 | 1/2016 | Majidi et al. |
| 9,231,186 B2 | 1/2016 | Busgen et al. |
| 9,266,233 B2 | 2/2016 | Kornbluh et al. |
| 9,333,097 B2 | 5/2016 | Herr et al. |
| 9,351,900 B2 | 5/2016 | Walsh et al. |
| 9,387,096 B2 | 6/2016 | Sverrisson et al. |
| 9,403,272 B2 | 8/2016 | Kornbluh et al. |
| 9,427,864 B2 | 8/2016 | Kornbluh et al. |
| 10,115,319 B2 | 10/2018 | Asbeck et al. |
| 2001/0007845 A1 | 7/2001 | Afanasenko et al. |
| 2003/0009120 A1 | 1/2003 | MacAllister |
| 2003/0030397 A1 | 2/2003 | Simmons |
| 2003/0064869 A1 * | 4/2003 | Reinkensmeyer ... A61B 5/1038 |
| | | 482/100 |
| 2003/0092545 A1 | 5/2003 | Koscielny et al. |
| 2003/0120183 A1 | 6/2003 | Simmons |
| 2003/0125781 A1 | 7/2003 | Dohno et al. |
| 2004/0043879 A1 | 3/2004 | Huang |
| 2004/0064195 A1 | 4/2004 | Herr |
| 2004/0087418 A1 * | 5/2004 | Eldridge .............. A63B 21/157 |
| | | 482/54 |
| 2004/0106881 A1 | 6/2004 | McBean et al. |
| 2004/0116260 A1 | 7/2004 | Drennan |
| 2004/0147378 A1 | 7/2004 | Conklin et al. |
| 2004/0204294 A2 * | 10/2004 | Wilkinson ........... A63B 21/015 |
| | | 482/54 |
| 2005/0010150 A1 | 1/2005 | Firsov |
| 2005/0049865 A1 | 3/2005 | Yaxin et al. |
| 2005/0070834 A1 | 3/2005 | Herr et al. |
| 2005/0101448 A1 * | 5/2005 | He ...................... A61H 1/0237 |
| | | 482/54 |
| 2005/0157893 A1 | 7/2005 | Pelrine et al. |
| 2005/0288157 A1 | 12/2005 | Santos-Munne et al. |
| 2006/0079817 A1 | 4/2006 | Dewald et al. |
| 2006/0108755 A1 | 5/2006 | Smyler et al. |
| 2006/0136206 A1 | 6/2006 | Ariu et al. |
| 2006/0192465 A1 | 8/2006 | Kornbluh et al. |
| 2006/0249315 A1 | 11/2006 | Herr et al. |
| 2007/0004570 A1 | 1/2007 | Afanasenko et al. |
| 2007/0004571 A1 | 1/2007 | Gonzalez |
| 2007/0066918 A1 | 3/2007 | Dewald et al. |
| 2007/0111868 A1 | 5/2007 | Fujii et al. |

(56) References Cited

U.S. PATENT DOCUMENTS

| | | |
|---|---|---|
| 2007/0123997 A1 | 5/2007 | Herr et al. |
| 2007/0135279 A1 | 6/2007 | Purdy et al. |
| 2008/0039756 A1 | 2/2008 | Thorsteinsson et al. |
| 2008/0062589 A1 | 3/2008 | Drabing |
| 2008/0071386 A1 | 3/2008 | McBean et al. |
| 2008/0075930 A1 | 3/2008 | Kornbluh et al. |
| 2008/0097269 A1 | 4/2008 | Weinberg et al. |
| 2008/0156363 A1 | 7/2008 | Ikeuchi et al. |
| 2008/0218132 A1 | 9/2008 | Pelrine et al. |
| 2008/0224564 A1 | 9/2008 | Pelrine et al. |
| 2008/0289952 A1 | 11/2008 | Pelrine et al. |
| 2008/0300118 A1* | 12/2008 | Wehrell .............. A63B 21/04 482/129 |
| 2009/0042702 A1 | 2/2009 | Toronto et al. |
| 2009/0221928 A1 | 9/2009 | Einav et al. |
| 2009/0255531 A1 | 10/2009 | Johnson et al. |
| 2009/0256817 A1 | 10/2009 | Perlin et al. |
| 2009/0306548 A1 | 12/2009 | Bhugra et al. |
| 2009/0319054 A1 | 12/2009 | Sankai |
| 2010/0000547 A1 | 1/2010 | Johnson et al. |
| 2010/0007240 A1 | 1/2010 | Kornbluh et al. |
| 2010/0024180 A1 | 2/2010 | Pei et al. |
| 2010/0026143 A1 | 2/2010 | Pelrine et al. |
| 2010/0030343 A1 | 2/2010 | Hansen et al. |
| 2010/0038983 A1 | 2/2010 | Bhugra et al. |
| 2010/0056966 A1 | 3/2010 | Toth |
| 2010/0144490 A1 | 6/2010 | Purdy et al. |
| 2010/0152630 A1 | 6/2010 | Matsuoka et al. |
| 2010/0185259 A1 | 7/2010 | Shiba et al. |
| 2010/0185301 A1 | 7/2010 | Hansen et al. |
| 2010/0204804 A1* | 8/2010 | Garrec .............. A61H 1/0277 623/24 |
| 2010/0271051 A1 | 10/2010 | Sankai et al. |
| 2010/0274364 A1 | 10/2010 | Pacanowsky |
| 2010/0280628 A1 | 11/2010 | Sankai |
| 2010/0286796 A1 | 11/2010 | Clausen |
| 2010/0298834 A1 | 11/2010 | Hildebrandt |
| 2010/0319215 A1 | 12/2010 | Roser |
| 2010/0324698 A1 | 12/2010 | Sverrisson et al. |
| 2011/0004322 A1 | 1/2011 | Sankai |
| 2011/0009793 A1 | 1/2011 | Lucero |
| 2011/0033835 A1 | 1/2011 | Endo et al. |
| 2011/0025170 A1 | 2/2011 | Rosenthal et al. |
| 2011/0040216 A1 | 2/2011 | Herr et al. |
| 2011/0062948 A1 | 3/2011 | Arns, Jr. et al. |
| 2011/0071647 A1 | 3/2011 | Mahon |
| 2011/0093089 A1 | 4/2011 | Martin |
| 2011/0150966 A1 | 5/2011 | Kazerooni et al. |
| 2011/0154641 A1 | 6/2011 | Pelrine et al. |
| 2011/0155307 A1 | 6/2011 | Pelrine et al. |
| 2011/0174524 A1 | 7/2011 | Sharma et al. |
| 2011/0193362 A1 | 8/2011 | Prahlad et al. |
| 2011/0201978 A1 | 8/2011 | Jeon et al. |
| 2011/0209337 A1 | 9/2011 | Pei et al. |
| 2011/0245738 A1 | 10/2011 | Agrawal et al. |
| 2011/0282255 A1 | 11/2011 | Nace |
| 2011/0295384 A1 | 12/2011 | Herr et al. |
| 2011/0295385 A1 | 12/2011 | Herr et al. |
| 2011/0313331 A1* | 12/2011 | Dehez .............. A61H 1/0277 601/33 |
| 2012/0019223 A1 | 1/2012 | Pelrine et al. |
| 2012/0023638 A1 | 2/2012 | Leicester |
| 2012/0056903 A1 | 3/2012 | Shinohara et al. |
| 2012/0071797 A1 | 3/2012 | Aoki et al. |
| 2012/0100286 A1 | 4/2012 | Sharma et al. |
| 2012/0109031 A1 | 5/2012 | Vollbrecht |
| 2012/0120544 A1 | 5/2012 | Pelrine et al. |
| 2012/0128960 A1 | 5/2012 | Busgen et al. |
| 2012/0165709 A1 | 6/2012 | Goffer et al. |
| 2012/0169184 A1 | 7/2012 | Pelrine et al. |
| 2012/0177934 A1 | 7/2012 | Vogel et al. |
| 2012/0179075 A1 | 7/2012 | Perry et al. |
| 2012/0181896 A1 | 7/2012 | Kronbluh et al. |
| 2012/0185052 A1 | 7/2012 | Lefeber |
| 2012/0209152 A1 | 8/2012 | Cordo |
| 2012/0238914 A1 | 9/2012 | Goldfield et al. |
| 2012/0248942 A1 | 10/2012 | Biggs et al. |
| 2012/0253234 A1 | 10/2012 | Yang et al. |
| 2012/0271207 A1 | 10/2012 | Schoen et al. |
| 2012/0279175 A1 | 11/2012 | Biggs et al. |
| 2012/0289870 A1 | 11/2012 | Hsiao-Wecksler et al. |
| 2012/0330198 A1 | 12/2012 | Patoglu |
| 2013/0013085 A1 | 1/2013 | Smith et al. |
| 2013/0019749 A1 | 1/2013 | Hufton et al. |
| 2013/0040783 A1 | 2/2013 | Duda et al. |
| 2013/0058001 A1 | 3/2013 | Prahlad et al. |
| 2013/0079686 A1 | 3/2013 | Sessions |
| 2013/0093439 A1 | 4/2013 | Ulmen et al. |
| 2013/0102935 A1 | 4/2013 | Kazerooni et al. |
| 2013/0123672 A1 | 5/2013 | Goffer et al. |
| 2013/0130866 A1* | 5/2013 | Wehrell .............. A61H 1/0229 482/5 |
| 2013/0158444 A1 | 6/2013 | Herr et al. |
| 2013/0165817 A1 | 6/2013 | Horst et al. |
| 2013/0179154 A1 | 7/2013 | Okuno |
| 2013/0186699 A1 | 7/2013 | Prahald et al. |
| 2013/0211295 A1 | 8/2013 | Johnson et al. |
| 2013/0225371 A1* | 8/2013 | Harrer .............. A63B 21/0552 482/8 |
| 2013/0226048 A1 | 8/2013 | Unluhisarcikli et al. |
| 2013/0230667 A1 | 9/2013 | Sharma et al. |
| 2013/0237884 A1 | 9/2013 | Kazerooni et al. |
| 2013/0245512 A1 | 9/2013 | Goffer et al. |
| 2013/0253385 A1 | 9/2013 | Goffer et al. |
| 2013/0261513 A1 | 10/2013 | Goffer et al. |
| 2013/0261766 A1 | 10/2013 | Langlois et al. |
| 2013/0268256 A1 | 10/2013 | Dariush |
| 2013/0274640 A1 | 10/2013 | Butters et al. |
| 2013/0288863 A1 | 10/2013 | Yamamoto et al. |
| 2013/0289452 A1 | 10/2013 | Smith et al. |
| 2013/0296746 A1 | 11/2013 | Herr et al. |
| 2013/0307370 A1 | 11/2013 | Jenninger et al. |
| 2013/0310979 A1 | 11/2013 | Herr et al. |
| 2013/0312541 A1 | 11/2013 | Majidi et al. |
| 2013/0328440 A1 | 12/2013 | Kornbluh et al. |
| 2014/0046455 A1 | 2/2014 | Herr et al. |
| 2014/0194781 A1 | 7/2014 | Einarsson et al. |
| 2015/0173993 A1 | 6/2015 | Walsh et al. |
| 2015/0266180 A1 | 9/2015 | Kornbluh et al. |
| 2015/0266181 A1 | 9/2015 | Kornbluh et al. |
| 2015/0297934 A1* | 10/2015 | Agrawal .............. A61H 1/0266 482/4 |
| 2015/0298765 A1 | 10/2015 | Golden, Jr. |
| 2015/0321399 A1 | 11/2015 | Hong et al. |
| 2016/0101516 A1 | 4/2016 | Kornbluh et al. |
| 2016/0101517 A1 | 4/2016 | Kornbluh et al. |
| 2016/0107309 A1 | 4/2016 | Walsh et al. |
| 2016/0220438 A1 | 8/2016 | Walsh et al. |
| 2016/0278948 A1 | 9/2016 | Piercy et al. |
| 2016/0284231 A1 | 9/2016 | Walsh et al. |
| 2017/0027735 A1 | 2/2017 | Walsh et al. |
| 2017/0163435 A1 | 6/2017 | Ehsani et al. |
| 2017/0202724 A1 | 7/2017 | Walsh et al. |
| 2018/0008502 A1 | 1/2018 | Asbeck et al. |

FOREIGN PATENT DOCUMENTS

| | | |
|---|---|---|
| CN | 101175456 | 3/2013 |
| CN | 102327173 | 5/2013 |
| DE | 19944139 | 4/2001 |
| EP | 0016268 | 10/1980 |
| EP | 0141640 | 10/1984 |
| EP | 0302148 | 2/1989 |
| EP | 0509723 A1 | 10/1992 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |

(56) References Cited

FOREIGN PATENT DOCUMENTS

| | | |
|---|---|---|
| JP | H07163607 A | 6/1995 |
| JP | 2002301124 A | 10/2002 |
| JP | 2005000500 A | 1/2005 |
| JP | 2007000391 A | 1/2007 |
| JP | 2008/067762 | 3/2008 |
| JP | 4345025 | 10/2009 |
| JP | 2010042069 A | 2/2010 |
| JP | 2010/051416 | 3/2010 |
| JP | 4424269 | 3/2010 |
| JP | 2010075656 A | 4/2010 |
| JP | 4582523 | 11/2010 |
| JP | 2011/036375 | 2/2011 |
| JP | 4848260 | 12/2011 |
| JP | 2012/192013 | 10/2012 |
| JP | 2013146328 A | 8/2013 |
| JP | 2014018536 A | 2/2014 |
| JP | 2014034145 A1 | 3/2014 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011/008934 | 1/2011 |
| WO | WO2011/026086 | 3/2011 |
| WO | WO2011/030641 | 3/2011 |
| WO | 2011126985 A2 | 10/2011 |
| WO | 2012014164 A2 | 2/2012 |
| WO | WO2012/050938 | 4/2012 |
| WO | WO2012/103073 | 8/2012 |
| WO | WO2012/124328 | 9/2012 |
| WO | WO2012/178171 | 12/2012 |
| WO | WO2013/019749 | 2/2013 |
| WO | 2013033669 A2 | 3/2013 |
| WO | WO2013/033669 | 3/2013 |
| WO | WO2013/044226 | 3/2013 |
| WO | 2013049658 A1 | 4/2013 |
| WO | WO2014/109799 | 7/2014 |
| WO | WO2014/194257 | 12/2014 |
| WO | WO2015/120186 | 8/2015 |
| WO | WO2015/157731 | 10/2015 |
| WO | WO2015/088863 | 12/2015 |
| WO | WO2016/089466 | 6/2016 |
| WO | WO2017/040669 | 3/2017 |
| WO | 2017160751 A1 | 9/2017 |
| WO | 2018017436 A1 | 1/2018 |

OTHER PUBLICATIONS

Browning, R. C. et al., "The effects of adding mass to the legs on the energetics and biomechanics of walking," Medicine and Science in Sports and Exercise, col. 39, p. 515, Apr. 2007.

Chu, A. et al, "On the biomimetric design of the Berkeley lower extremity exoskeleton (BLEEX)", Proc. 2005 in IEEE Int. Conf. Robotics and Automation (IEEE Press, Barcelona, Spain, pp. 4356-4363 Apr. 2006).

Clevertex: Development of Strategic Master Plan for the transformation of the traditional textile and clothing into a knowledge driven industrial sector by 2015, 160 pages, dated prior to Jul. 2014.

Collins, S., et al., "Efficient Bipedal Robots Based on Passive-Dynamic Walkers," Science, vol. 307, Issue 5712, pp. 1082-1085, Feb. 18, 2005.

Cool, J.C., "Biomechanics of orthoses for the subluxed shoulder," Prosthetics & Orthotics International; vol. 13, Issue 2, pp. 90-96, 1989.

da Silva, A. F. et al., "FBG Sensing Glove for Monitoring Hand Posture," IEEE Sensors Journal, vol. 11, Issue 10, pp. 2442-2448, Oct. 2011.

De Rossi, D. et al., "Wearable technology for biomechanics: e-textile or micromechanical sensors?" IEEE engineering in medicine and biology magazine, vol. 29, No. 3, pp. 37-43, May/Jun. 2010. [Online]. Available: http://www.ncbi.nlm.nih.gov/pubmed/20659856.

Delp, S. L. et al., "OpenSim: open-source software to create and analyze dynamic simulations of movement." IEEE transactions on bio-medical engineering, vol. 54, No. 11, pp. 1940-1950, Nov. 2007. [Online]. Available: http://www.ncbi.nlm.nih.gov/pubmed/18018689.

Dollar, A. M. et al., "Lower extremity exoskeletons and active orthoses: Challenges and state-of-the-art,", IEEE Transactions on Robotics, vol. 24, No. 1, pp. 144-158, Feb. 2008.

Erk, K. A. et al., "Strain stiffening in synthetic and biopolymer networks," Biomacromolecules, vol. 11, No. 5, pp. 1358-1363, May 2010.

Farris D.J., et al., Human medial gastrocnemius force-velocity behavior shifts with locomotion speed and gait. Proc Natl Acad Sci USA. Jan. 2012; 109:977-982.

Ferris, D. P. et al., "Robotic lower limb exoskeletons using proportional myoelectric control," in EMBC 2009, Annual International Conference of the IEEE Engineering in Medicine and Biology Society, 2009.

Ferris, D.P. et al., A Physiologist's Perspective on Robotic Exoskeletons for Human Locomotion. Int J HR, 4(3): p. 507-528, 2007.

Ghodsi et al., De novo Likelihood-based measures for comparing genome assemblies. In: BMC Research Notes 2013, Aug. 22, 2013—online retrieved on Oct. 25, 2016.

Gibbs, P. et al.: Wearable Conductive Fiber Sensors for Multi-Axis Human Joint Angle Measurements.

Journal of NeuroEngineering and Rehabilitation, Mar. 2, 2005.

Goodvin, C.I.: Development of a Real-time Spinal Motion Inertial Measurement System for Vestibular Disorder Application, University of Victoria, 155 pages, date 2003.

Gregorczyk, K. N., et al., The effects of a lower body exoskeleton load carriage assistive device on oxygen consumption and kinematics during walking with loads, in 25th Army Sci. Conf., Florida, USA, 2006.

Hallemans, A. et al.: 3D joint dynamics of walking in toddlers. A cross-sectional study spanning the first rapid development phase of walking. Gait & Posture, 22:107-118, 2005.

Kadaba, M. P., et al., "Measurement of lower extremity kinematics during level walking." Journal of orthopaedic research: official publication of the Orthopaedic Research Society, vol. 8, No. 3, pp. 383-392, May 1990. [Online]. Available: http://www.ncbi.nlm.nih.gov/pubmed/2324857.

Kawamoto, H., et al., Power assist method for HAL-3 using EMG-based feedback controller. in Systems, Man and Cybernetics, 2003. IEEE International Conference on. 2003.

Kim, D.-H. et al., "Epidermal electronics." Science, vol. 333, No. 6044, pp. 838-843, Aug. 2011. [Online] Available: http://www.sciencemag.org/cgi/doi/10.1126/science.1206157.

Kramer, R. K. et al., "Soft curvature sensors for joint angle proprioception," in 2011 IEEE/RSJ International Conference on Intelligent Robots and Systems. IEEE, pp. 1919-1926, Sep. 2011. [Online]. Available: http://ieeexplore.ieee.org/lpdocs/epic03/wrapper.htm?arnumber=6094701.

Kramer, R. K. et al., "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.

Kulyukin, V. A.: Advances in Human-Robot Interaction, 354 pages, Dec. 2009.

Lee, S. W. et al.: Biomimetic Approach Enables Functional Movements of Hand Post Stroke: A Pilot Study, 2 pages, dated 2012.

Lipomi, D. J. et al., "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.

Majidi, C. et al., "A non-differential elastomer curvature sensor for softer-than-skin electronics," Smart Materials and Structures, vol. 20, No. 10, p. 105017, Oct. 2011. [Online]. Available: http://stacks.iop.org/0964-1726/20/i=10/a=105017?key=crossref.0cca7e97d6ad7110bcdcaf45f30f3b60.

Malcolm, Philippe et al., Fast Exoskeleton Optimization. Science, vol. 356, Issue 6344, pp. 1230-1231, Jun. 23, 2017.

(56) References Cited

OTHER PUBLICATIONS

Mattila, H. R., Intelligent textiles and clothing, Woodhead Publishing Limited, 525 pages, © 2006.

McGeer, T., Passive Bipedal Running. Proceedings of the Royal Society of London. Series B, Biological Sciences, 240(1297): p. 107-134, May 1990.

Newman, D. J. et al., Astronaut Bio-Suit System to Enable Planetary Exploration. In International Astronautical Conference, Vancouver, Canada, Oct. 2004.

Park, Y. L. et al., Active Modular Elastomer Sleeve for Soft Wearable Assistance Robots, 2012 IEEE/RSJ International Con. On Intelligent Robots and Systems Vilamoura, Algarve, Portugal, 8 pages, Oct. 7-12, 2012.

Park, Y.-L., et al., "Design and Fabrication of Soft Artificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber=6203551.

Park, Y.-L., "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=125029?key=crossref.84cffc44789ba7bde0bdfd169e25af91.

Park, Y.-L., et al.: Bio-inspired Active Soft Orthotic Device for Ankle Foot Pathologies, 2011 IEEE/RSJ International Conference on Intelligent Robots and Systems, San Francisco, CA, USA, 8 pages, Sep. 25-30, 2011.

Pereira da Fonseca, P. F.: Validation of two types of textile electrodes for electrocardiography and electromyography measurement applications, 126 pages, dated Jul. 2012.

Polonen et al. Automatic Intensity Quantification of Fluorescence Targets from microscope Images with Maximum Likelihood Estimation. 17th European Signal Processing Conference, Aug. 24-28, 2009—retrieved online Oct. 25, 2016.

Pratt, J. et al., The RoboKnee: An exoskeleton for enhancing strength and endurance during walking, in IEEE Int. Conf. Robotics and Automation (ICRA), New Orleans, USA (IEEE Press), pp. 2430-2435, Apr. 2004.

Quintero, H. A. et al., "Control and Implementation of a Powered Lower Limb Orthosis to Aid Walking in Paraplegic Individuals," in IEEE International Conference on Rehabilitation Robotics, Switzerland, pp. 1-6, Jun. 29-Jul. 1, 2011.

Ramuz, M. et al., "Transparent, Optical, Pressure-Sensitive Artificial Skin for Large-Area Stretchable Electronics," Advanced Materials, May 2012. [Online]. Available: http://doi.wiley.com/10.1002/adma.201200523.

Reid, S. A. et al., "Biomechanical assessment of rucksack shoulder strap attachment location: effect on load distribution to the torso," presented at the RTO HFM specialists' Meeting on "Soldier Mobility: Innovations in Load Carriage System Design and Evaluation," NATO-RTO Meeting Proceedings: MP-056 (Neuilly-sur-Seine: NATO). Jun. 1-6, 2000.

Royer, T.D. et al., (2005) 'Manipulations of Leg Mass and Moment of Inertia: Effects on Energy Cost of Walking, Medicine & Science in Sports & Exercise, vol. 37, No. 4: p. 649-656, 2005.

Salvendy, G.: Smart Clothing Technology and Applications, Human Factors and Ergonomics, by Taylor and Francis Group, LLC, 290 pages, © 2010.

Schiele, A. "Ergonomics of Exoskeletons: Objective Performance Metrics" in Euro Haptics conference and symposium on Haptic Interfaces for Virtual Environmental Teleoperator Systems, Salt Lake City, UT, USA, Mar. 2009.

Scilingo, E. P. et al., "Strain-sensing fabrics for wearable kinaesthetic-like systems," IEEE Sensors Journal, vol. 3, No. 4, pp. 460-467, Aug. 2003. [Online]. Available: http://ieeexplore.ieee.org/lpdocs/epic03/wrapper.htm?arnumber=1226639.

Silva, H. R., et al.: Wireless Hydrotherapy Smart-Suit Network for Posture Monitoring, 5 pages, dated 2007.

Strauser, K. A. et al., "The development and testing of a human machine interface for a mobile medical exoskeleton" in IEEE Int Conf, Intelligent Robots and Systems, San Francisco, CA. USA, Sep. 2011.

Tesconi, M., et al., "Wearable sensorized system for analyzing the lower limb movement during rowing activity," 2007 IEEE International Symposium on Industrial Electronics, pp. 2793-2796, Jun. 2007. [Online]. Available: http://ieeexplore.ieee.org/lpdocs/epic03/wrapper.htm?arnumber=4375052.

Tiwana, M. I., et al., "A review of tactile sensing technologies with applications in biomedical engineering," Sensors and Actuators A: Physical, vol. 179, pp. 17-31, Jun. 2012. [Online]. Available: http://linkinghub.elsevier.com/retrieve/pii/S0924424712001641.

Vogt, D. M., et al., Design and Characterization of a Soft Multi-Axis Force Sensor Using Embedded Microfludic Channels, IEEE Sensors Journal, vol. 13. No. 10, 9 pages, Oct. 2013.

Walsh, C. J., et al., A Quasi-Passive Leg Exoskeleton for Load Carrying Augmentation. International Journal of Humanoid Robotics, Special Issue: Active Exoskeletons, 4(3): 487-506, 2007.

Wehner, M., 2012 "Man to Machine, Applications in Electromyography," EMG Methods for Evaluation Muscle and Nerve Functions. Intech Publishing, Sep. 13, 2012 http://intechopen.com/articles/show/title/man-to-machine-applications-in-electromyography.

Wehner, M., et al., "Experimental characterization of components for active soft orthotics," in Proc. IEEE Int. Conf. Biomed. Rob. Biomechatron., Roma, Italy, Jun. 2012.

Wehner, M., et al., "Lower Extremity Exoskeleton Reduces Back Forces in Lifting" ASME Dynamic Systems and Control Conference, Hollywood, California, USA pp. 49-56, Oct. 12-14, 2009.

Woodman, O.J. "An introduction to inertial navigation," Technical Report UCAM-CL-TR-696, Aug. 2007.

Yamada, T. et al., "A stretchable carbon nanotube strain sensor for human-motion detection." Nature Nanotechnology, vol. 6, No. 5 pp. 296-301, May 2011. [Online]. Available: http:/ncbi.nlm.nih.gov/pubmed/21441912.

Zhang, R. et al., "Carbon nanotube polymer coatings for textile yarns with good strain sensing capability," Sensors and Actuators A: Physical, vol. 179, pp. 83-91, Jun. 2012. [Online]. Available: http://linkinghub.elsevier.com/retrieve/pii/S0924424712001938.

Zhang, Juanjuan et al., Human-in-the-Loop Optimization of Exoskeleton Assistance During Walking, Science, vol. 356, pp. 1280-1284, Jun. 23, 2017.

Zoss, A.B., et al., Biomechanical design of the Berkeley lower extremity exoskeleton (BLEEX), IEE/ASME Transactions on Mechatronics, 11(2): p. 128-138, Apr. 2006.

PCT International Search Report, issued in International Application No. PCT/EP2003/012123, dated Jun. 22, 2004.

PCT International Search Report and Written Opinion, issued in International Application No. PCT/US2013/060225, dated May 27, 2014.

PCT International Search Report and Written Opinion, issued in International Application No. PCT/US2014/040340, dated Oct. 31, 2014.

PCT International Search Report and Written Opinion, issued in International Application No. PCT/US2014/068462, dated May 22, 2015.

PCT International Search Report and Written Opinion, issued in International Application No. PCT/US2015/014672, dated Jul. 6, 2015.

PCT International Search Report and Written Opinion, issued in International Application No. PCT/US2015/025472, dated Sep. 4, 2015.

PCT International Search Report and Written Opinion, issued in International Application No. PCT/US2015/051107 dated Aug. 5, 2016.

PCT International Search Report and Written Opinion, issued in International Application No. PCT/US2016/049706 dated Nov. 29, 2016.

Extended European Search Report issued in European Application No. 13871010.8 dated Sep. 2, 2016.

(56) References Cited

OTHER PUBLICATIONS

PCT International Search Report and Written Opinion, issued in International Application No. PCT/US2017/022150 dated Jun. 9, 2017.
Extended European Search Report issued in European Application No. 14803880.5 dated May 19, 2017.
PCT International Search Report and Written Opinion, issued in International Application No. PCT/US2017/042286, dated Sep. 28, 2017.
Supplementary European Search Report issued in European Application No. 15 77 6544 dated Oct. 20, 2017.
USPTO Office Action in U.S. Appl. No. 14/660,704 dated Feb. 7, 2018.
Extended European Search Report issued in European Application No. 15746146.8 dated Feb. 27, 2018.
USPTO Office Action in U.S. Appl. No. 14/660,704 dated Jun. 28, 2018.
USPTO Office Action in U.S. Appl. No. 14/660,704 dated Nov. 8, 2018.

* cited by examiner

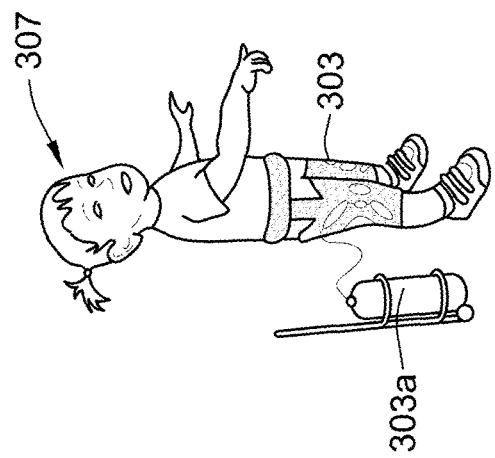
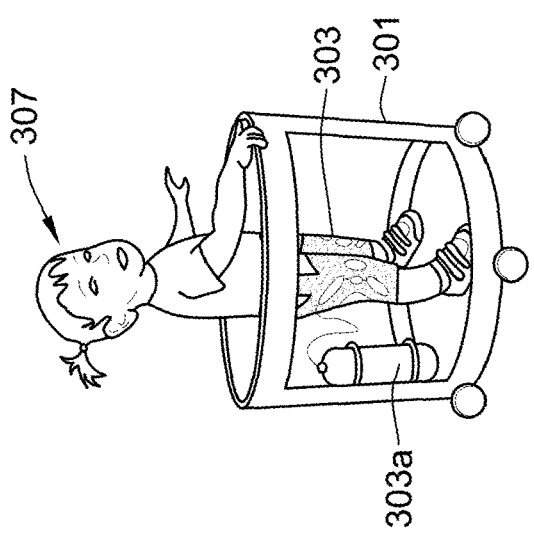
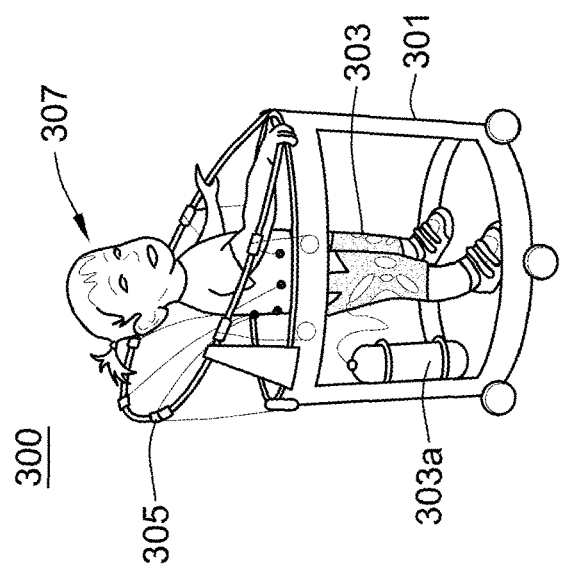
FIG. 3C
FIG. 3B
FIG. 3A

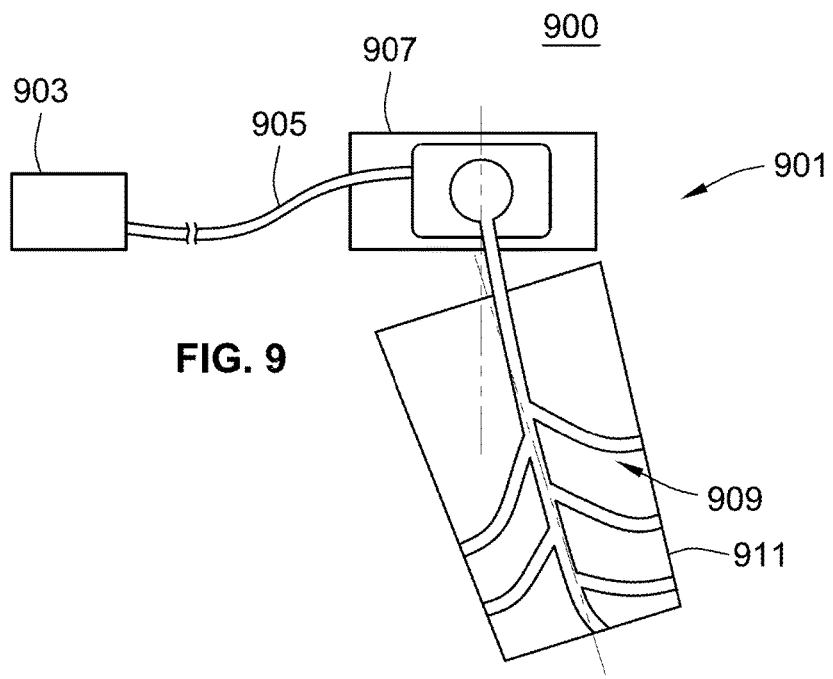
FIG. 9
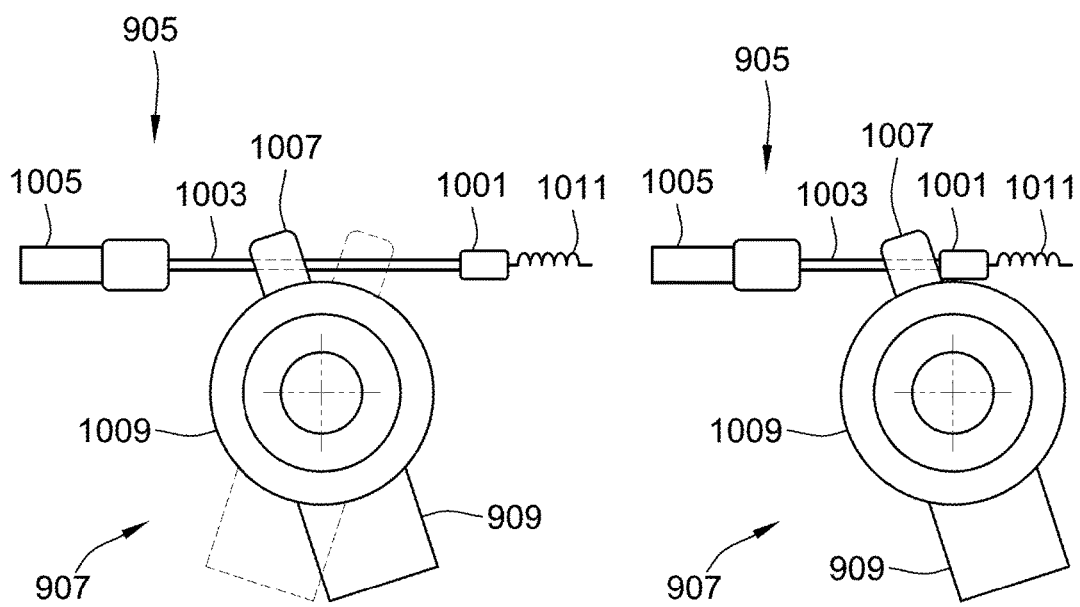
FIG. 10A  FIG. 10B

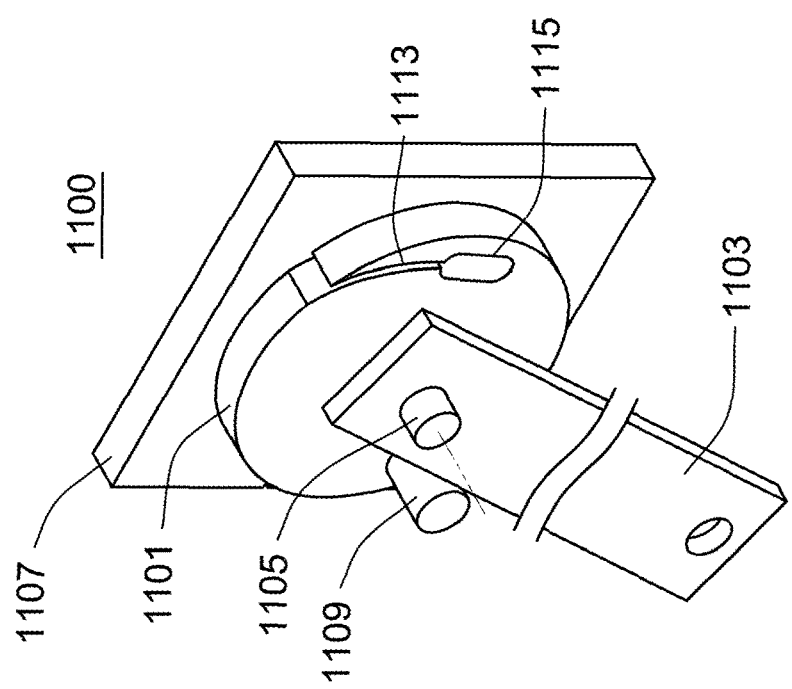
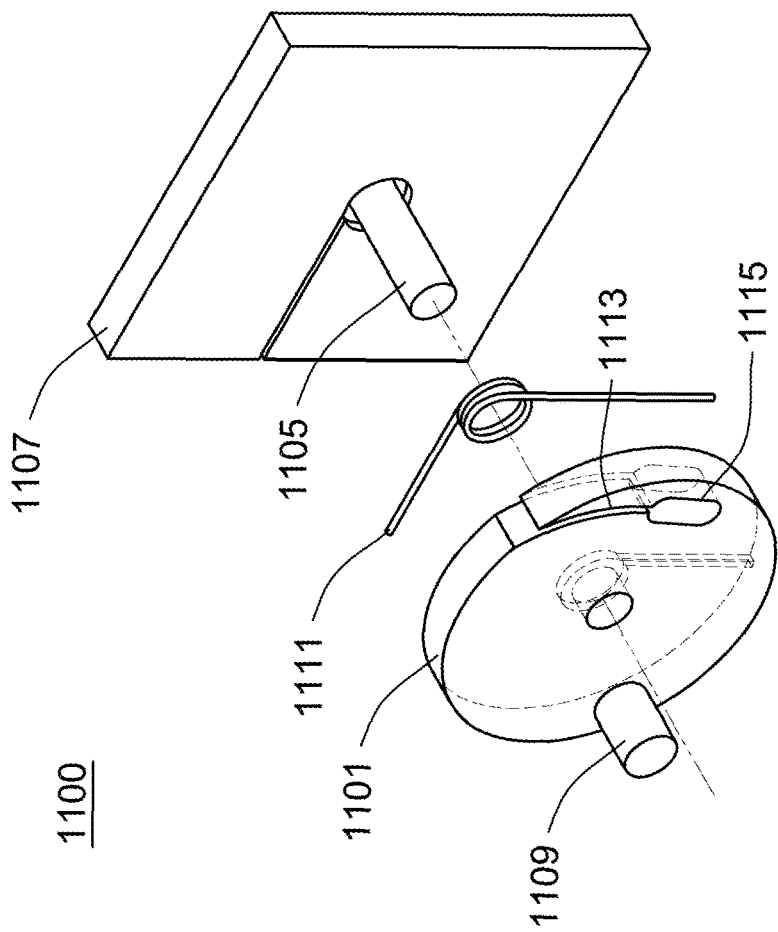

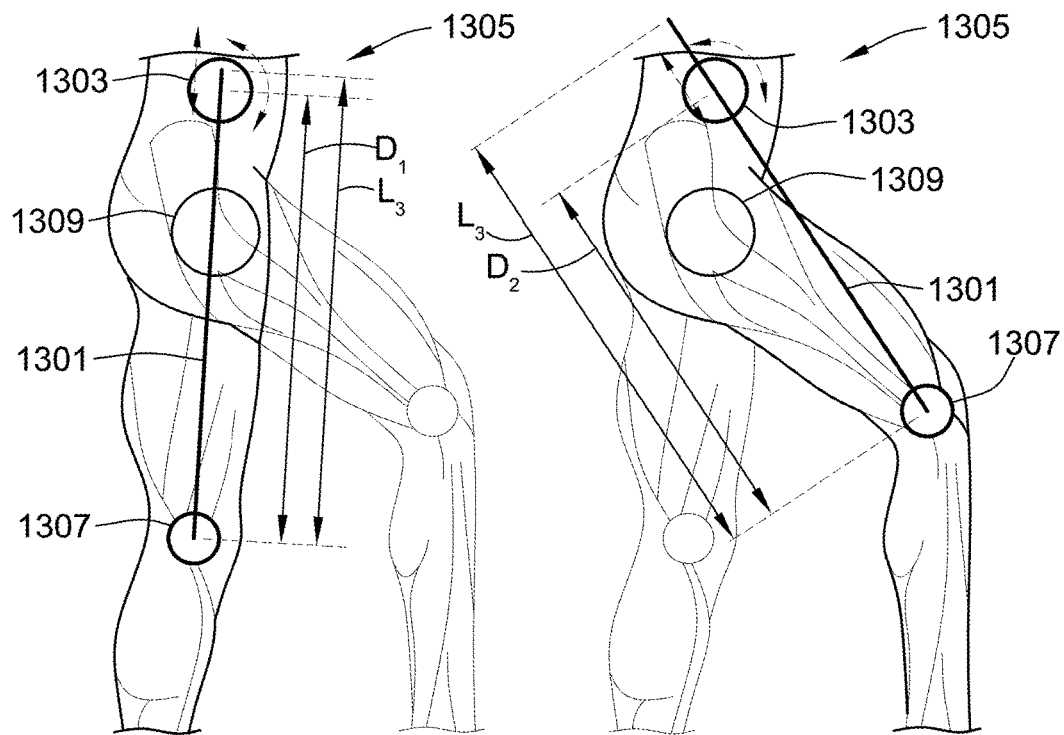
FIG. 13A  FIG. 13B
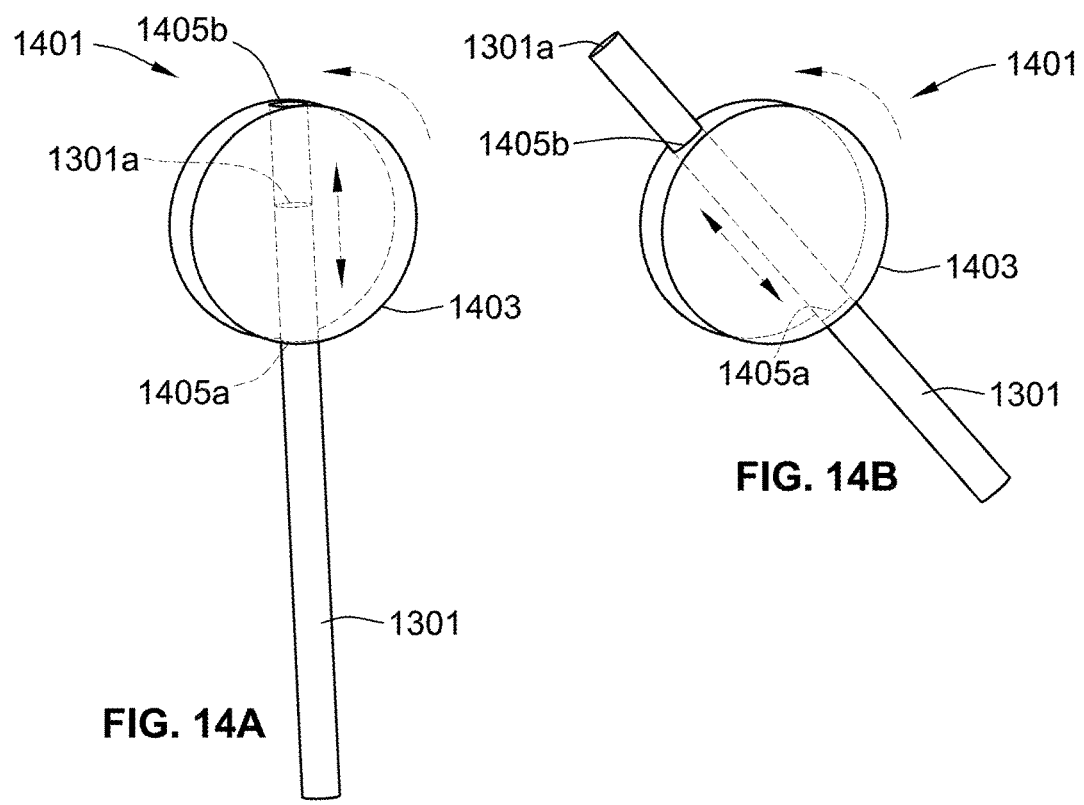
FIG. 14A  FIG. 14B

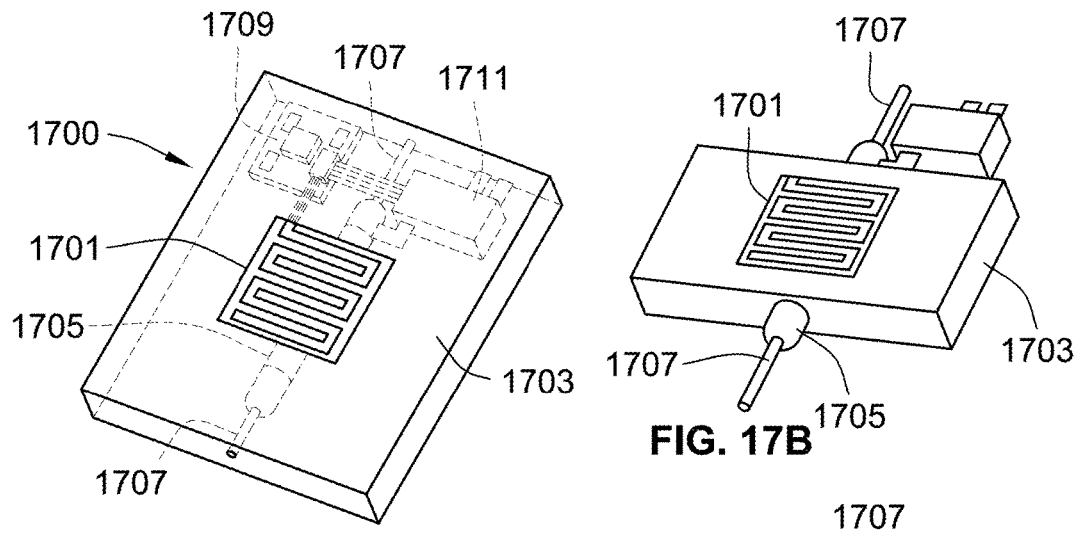
FIG. 17A
FIG. 17B
FIG. 17C
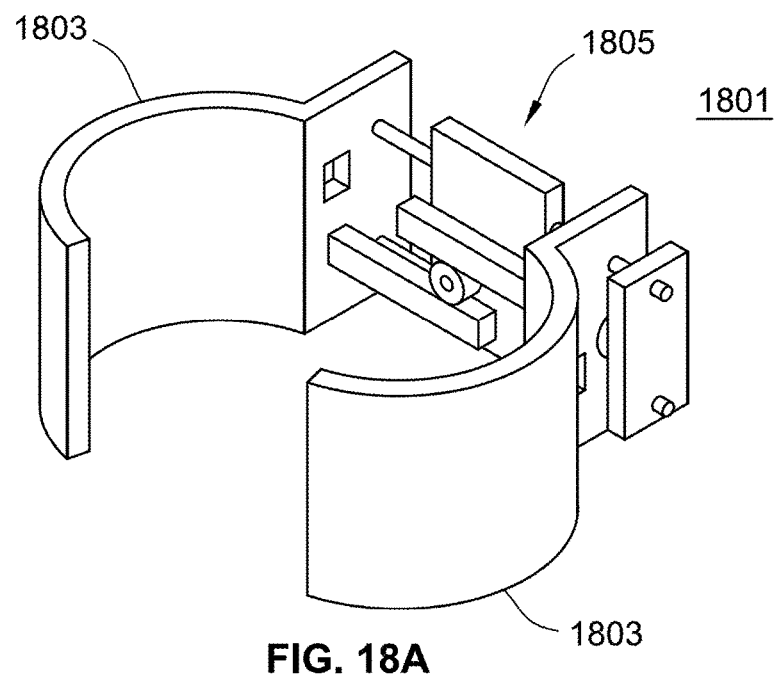
FIG. 18A

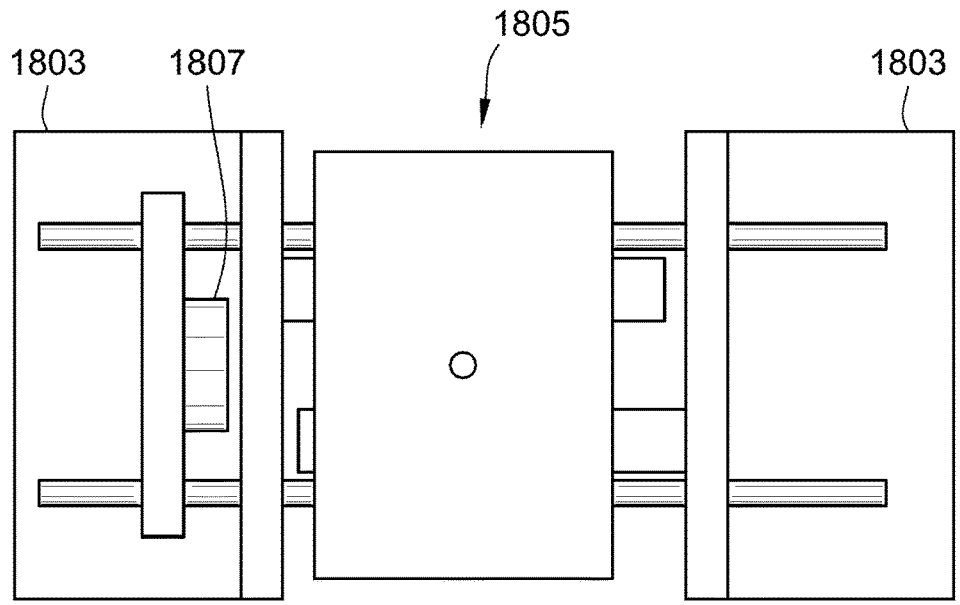
FIG. 18B
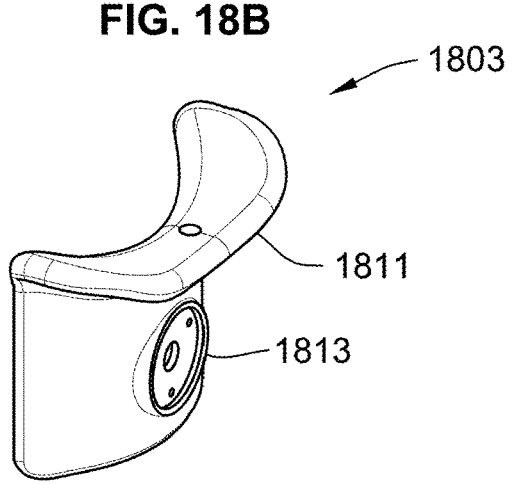
FIG. 19A
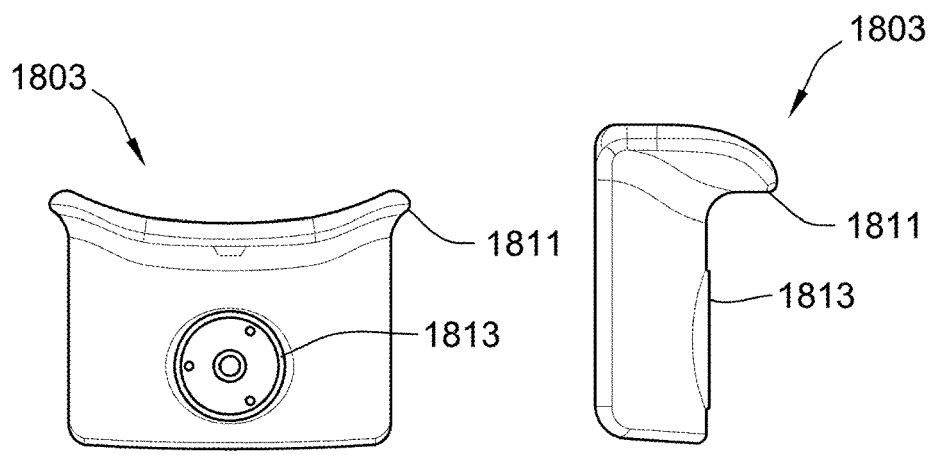
FIG. 19B     FIG. 19C

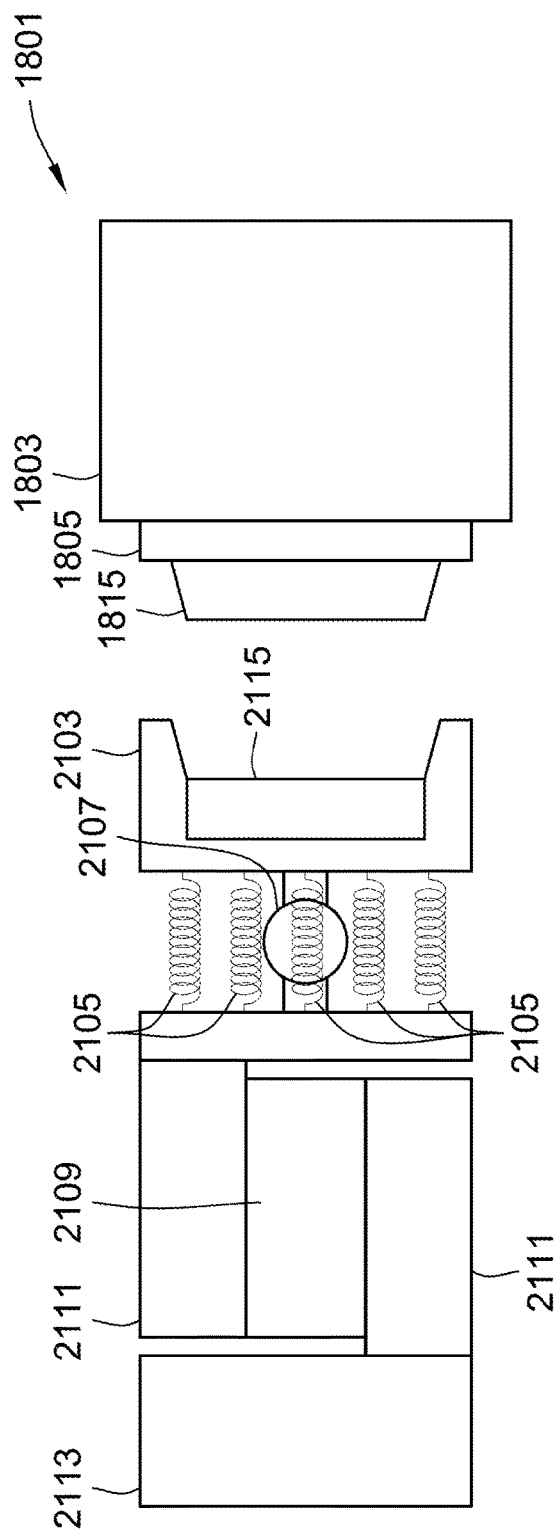
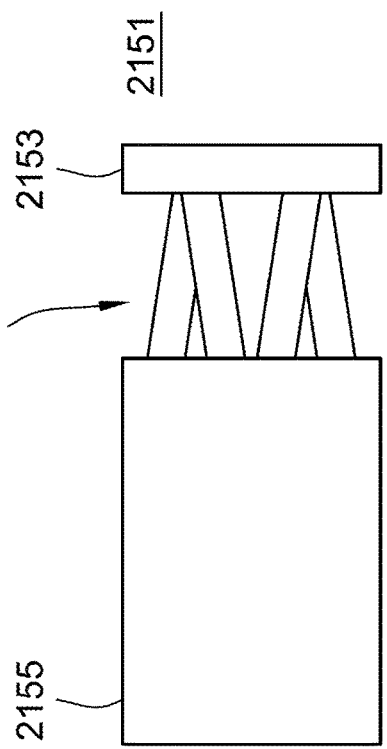
FIG. 21A
FIG. 21B

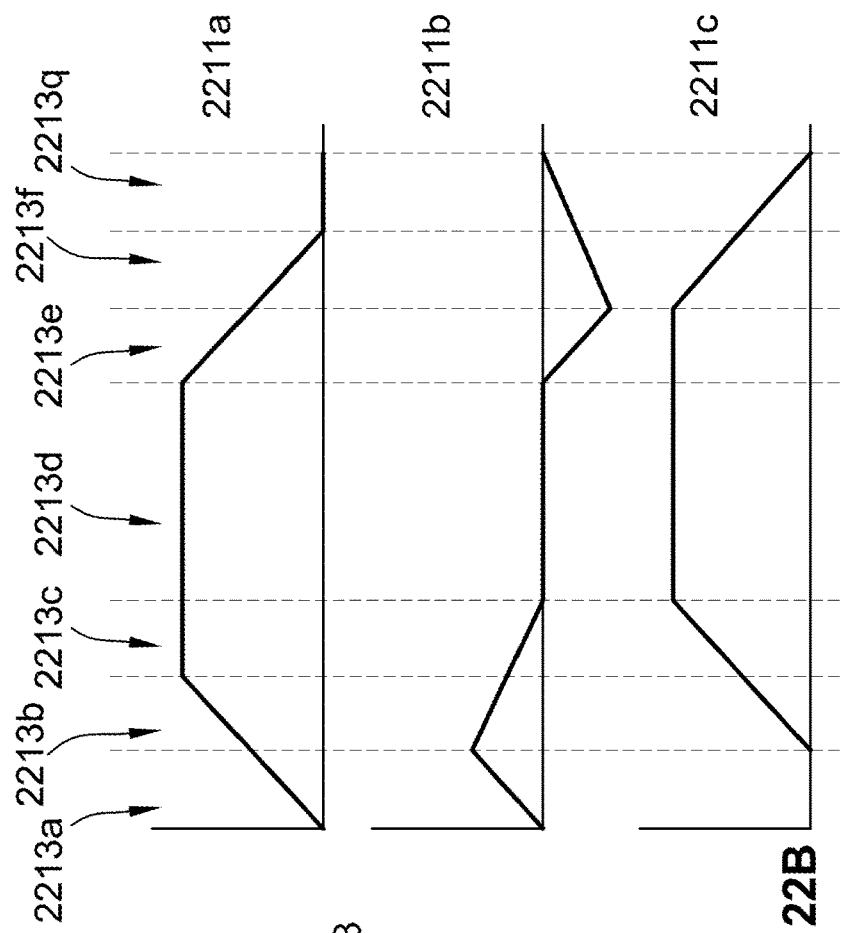
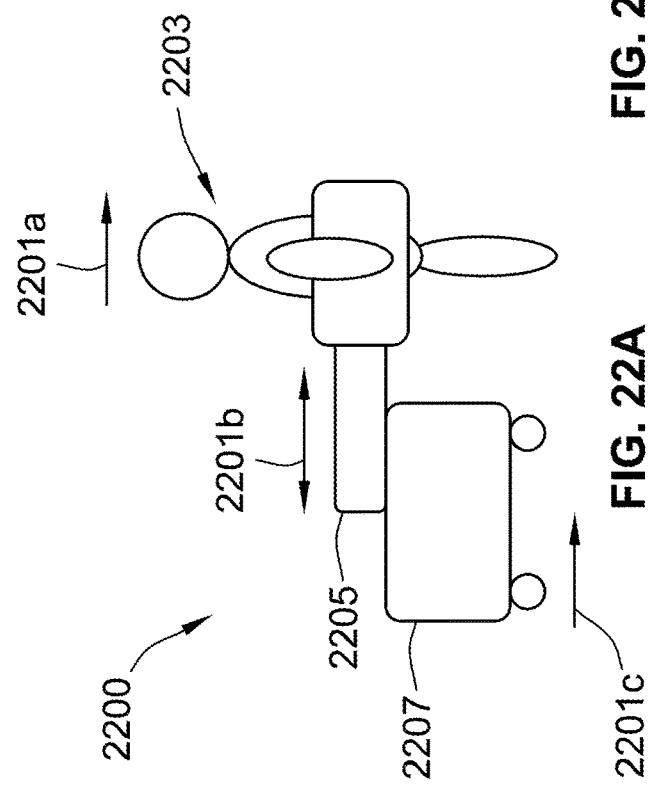
FIG. 22A
FIG. 22B

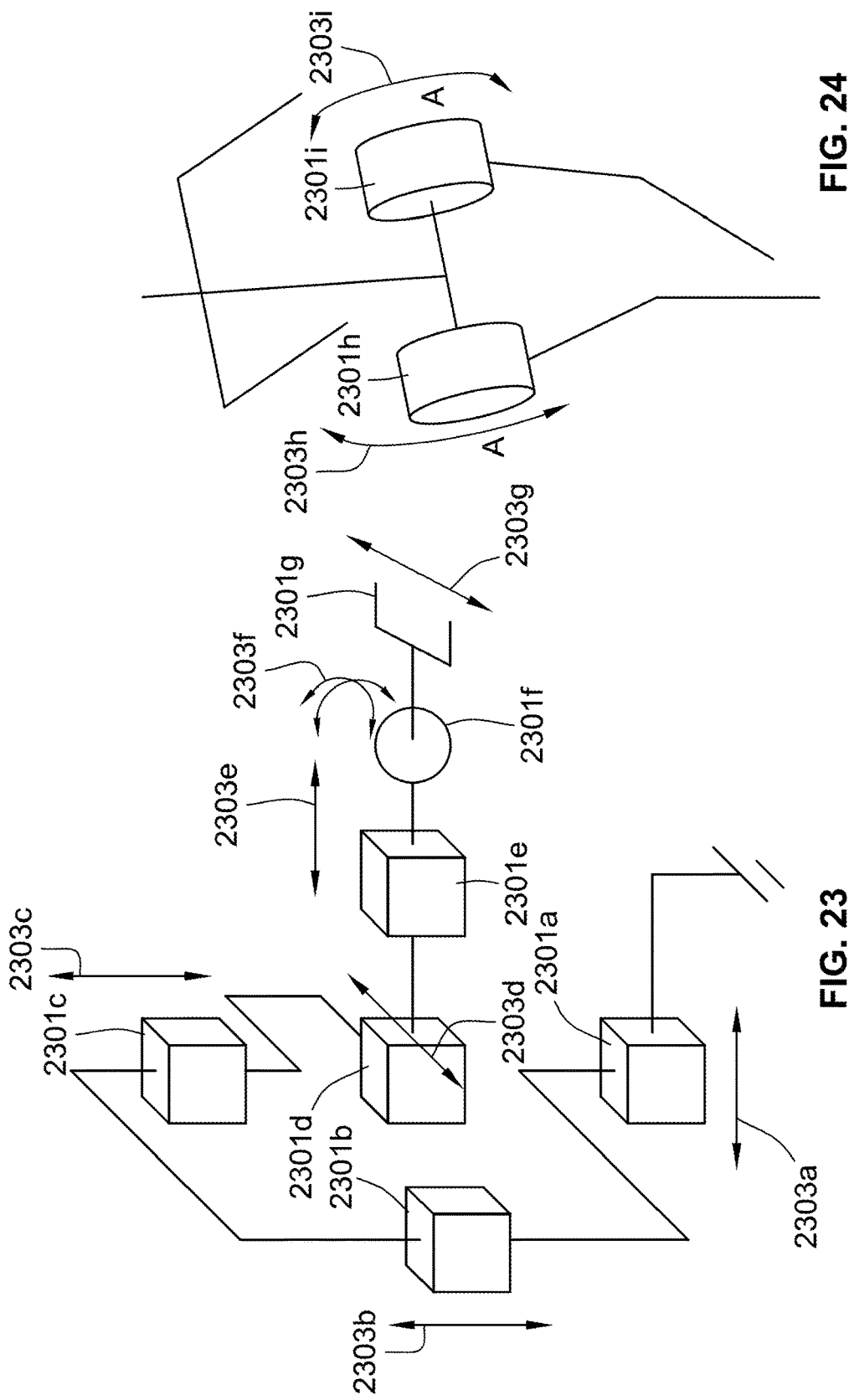

SYSTEMS, METHODS, AND DEVICES FOR ASSISTING WALKING FOR DEVELOPMENTALLY-DELAYED TODDLERS

CROSS-REFERENCE AND CLAIM OF PRIORITY TO RELATED APPLICATIONS

The present application is a U.S. national phase application of PCT International Patent Application No. PCT/US2015/014672, filed on Feb. 5, 2015, titled, "Systems, Methods, and Devices for Assisting Walking for Developmentally-Delayed Toddlers," which claims priority to U.S. Provisional Patent Application No. 61/936,162, titled "Multi-Robot Cyberphysical System for Assisting Walking in Developmentally-Delayed Toddlers," filed Feb. 5, 2014, each of the preceding applications being incorporated herein by reference in its entirety.

STATEMENT REGARDING FEDERALLY SPONSORED RESEARCH

Some aspects of the present disclosure were made with government support under NSF Grant No. CNS-1329363 awarded by the National Science Foundation, and the government shares rights to such aspects of the present disclosure.

TECHNICAL FIELD

The present concepts are generally directed to methods and systems for developing motion in humans. More particularly, aspects of the present disclosure are directed to systems, methods, and devices for developing motion by passively and/or actively adding assistive energy or resistive energy to one or more movements, and for providing cues for the movements, as appropriate, in developmentally-delayed and/or impaired toddlers.

BACKGROUND

Newly walking toddlers face difficult challenges in learning to walk. Such challenges result from the high number of degrees-of-freedom of individual body segment rotations and the inherent variability of body motion during bipedal gait in a gravitational field.

In learning to walk, toddlers may take up to 9000 steps per day. For the average toddler, this is equivalent to traversing the length of more than 20 football fields. During these first steps, and throughout the learning process, newly walking toddlers may be assisted in their exploratory behavior by adults who stabilize their body motion by holding one or both hands, or supporting the toddler's trunk at the hips. Adults assisting toddlers learning to walk provide ever-changing postural support that provides the toddlers the opportunity to safely explore the forces acting on their bodies.

A fundamental challenge in learning to walk is that stepping attempts result in simultaneous body motion in two planes, anterior-posterior and medial-lateral. However, with an abundance of body degrees-of-freedom (DOF) to control, toddlers appear to be able to learn to control body motion in only one plane at a time. As most toddlers learn to walk, the toddlers learn to reduce variability in one plane of motion while relaxing motion variability in another other. However, there are limits to the toddlers' abilities to use their muscles to control motion variability. Therefore, learning may be a continuously modulated process, rather than a fixed or absolute freezing in one plane and relaxation in the other.

Adding to the complexity and challenges in learning to walk for some toddlers can be developmental delays caused by injury (e.g., brain injury or other bodily injury). Premature birth remains a major public health problem despite recent advances. By way of example, in 2008 alone, 1.5% of the more than 4.25 million births (i.e., more than 63,000 infants) were born at a very low birth weight (VLBW) (≤1500 g). Of the 90% of surviving VLBW infants, 25-50% experienced a brain injury that accounts for delays in locomotive development. The long-term consequences of early brain injury (e.g., in children born prematurely) constitute a major health problem and a significant emotional and financial burden for families and society.

Therefore, a need exists for developing locomotive motion in developmentally-delayed toddlers to relieve the physical, emotional and financial burdens such development delay causes.

SUMMARY

The present concepts are directed to methods, systems, and devices configured to promote locomotive motion to overcome developmental delays and/or regression in bodily control caused by injuries (e.g., developmental delays caused by premature birth and regression in bodily control caused by strokes and/or spinal cord injuries).

In at least some aspects of the present concepts, a multi-robot cyber-physical system is disclosed for assisting developmentally delayed toddlers in learning to walk. The modular system is a tight conjoining of and coordination between computational and physical resources by multiple robotic devices (or modules) that each address a subtask of motion. The modular system help toddlers lacking in mobility to learn or regain abilities related to motion (e.g., walking).

In at least some aspects of the present concepts, a method of enabling rehabilitation of bodily control of a user comprises the acts of integrating the user within a multi-module robotic system comprising a plurality of interrelated modules. In some aspects, this multi-module robotic system comprises at least one of a flexible exosuit, a support module, and a mobile base. The flexible exosuit is worn on the user and is configured to modify motion of the user at one or more joint- and/or limb-specific locations. The support module is configured to dynamically influence the center-of-mass (COM) of the user according to one or more influences to one or more body segments and/or the entire body. The mobile base provides a structural support for one or more of the flexible exosuit, the support module, and the user. The method further includes applying one or more forces, cues, or a combination thereof on the user, based on one or more subtask-specific functions of the modules, to cause a developing of one or more subtasks of the bodily control. The method further includes managing control of one or more remaining subtasks of the bodily control by the modules in place of, at least in part, the user, while applying the one or more forces, cues, or a combination thereof in a coordinated matter.

In at least some other aspects of the present concepts, disclosed is a modular robotic system configured to therapeutically assist a mobility-challenged user. The system includes a flexible exosuit configured to be worn on the user and to apply forces, cues, or a combination thereof to provide assistance to gait. The system further includes a support module configured to modulate a center-of-mass (COM), one or more positions of one or more body segments, or a combination thereof of the user with respect to an anterior-posterior direction, a medial-lateral direction, or a combination thereof. The system further includes a mobile base comprising a structural support for one or more elements of the flexible exosuit, one or more elements of the support module, and the user. The system also includes a controller configured to, from a predetermined plurality of different walking parameters, selectively vary one or more of the plurality of walking parameters through control inputs to one or more of the flexible exosuit, the support module, or the mobile base, while maintaining remaining ones of the plurality of the walking parameters, to assist the user to learn bodily control with respect to the plurality of walking parameters.

In at least some other aspects of the present concepts, a method of using a modular robotic system to enable rehabilitation of a user with respect to stance and/or mobility comprises the acts of equipping the user with the modular robotic system. The modular robotic system includes at least one of a flexible exosuit, a support module, a mobile base, or combination thereof. The modular robotic system being configured to apply forces, cues, or a combination thereof to the user to assist at least one of limb movement and balance. The support module being configured to dynamically influence a position of the center-of-mass (COM) of the user and/or one or more positions of one or more body segments and/or limbs of the user. The mobile base providing a structural support connected to one or more of the flexible exosuit, the support module, and the user. The method further includes developing a first subset of parameters with respect to stance and/or mobility of the user based on one or more operations of the modular robotic system on the user. Further, the method includes determining whether the first subset of parameters of the stance and/or mobility satisfies a first rehabilitative progression threshold. The method further includes modifying the modular robotic system at or following satisfaction of the first rehabilitative progression threshold for the first subset of parameters of the stance and/or mobility by removing a component of the modular robotic system, the component comprising the flexible exosuit or the support module. In addition, the method includes developing a second subset of parameters of the stance and/or mobility of the user based on one or more operations of the modified modular robotic system.

In at least some other aspects of the present concepts, a method of providing feedback to a user of a therapeutic multi-module robotic system comprises the acts of integrating the user within a multi-module robotic system. In some aspects, the multi-module robotic system comprises a flexible exosuit, a support module, or a mobile base, or a combination thereof. The flexible exosuit is worn on the user and configured to modify motion of the user at one or more joint- and/or limb-specific locations. The support module is configured to influence a center-of-mass (COM), one or more body segments, or a combination thereof of the user. The mobile base provides a structural support for one or more of the flexible exosuit, the support module, and the user. The method further includes applying one or more forces, cues, or a combination thereof on the user, based on one or more subtask-specific functions of the multi-module robotic system, to cause a developing of one or more subtasks of the bodily control. The method further includes managing control of one or more remaining subtasks of the bodily control by the multi-module robotic system in place of, at least in part, the user, while applying the one or more forces, cues, or a combination thereof.

The above summary is not intended to represent each embodiment or every aspect of the present disclosure. Rather, the foregoing summary merely provides an exemplification of some of the novel aspects and features presented herein. The above features and advantages, and other features and advantages of the present disclosure, will be readily apparent from the following detailed description of exemplary embodiments and modes for carrying out the present invention when taken in connection with the accompanying drawings and the appended claims.

BRIEF DESCRIPTION OF THE FIGURES

FIGS. 3A-3C show a progression of a modular system based on a corresponding development in motion of a user in accord with at least some aspects of the present concepts.

FIG. 9 shows a hip drive unit in accord with at least some aspects of the present concepts.

FIGS. 10A and 10B show actuation states of a hip drive unit in accord with at least some aspects of the present concepts.

FIGS. 11A and 11B show an expanded view (FIG. 11A) and a schematic view (FIG. 11B) of an alternative drive hip unit in accord with at least some aspects of the present concepts.

FIGS. 13A and 13B show centers of rotation of the leg in straight (FIG. 13A) and bent (FIG. 13B) configurations with respect to a drive shaft in accord with at least some aspects of the present concepts.

FIGS. 14A and 14B illustrate various configurations of a prismatic joint in accord with at least some aspects of the present concepts.

FIGS. 17A-17C show a hyper-elastic strain sensor and actuation states (FIGS. 17B and 17C) in accord with at least some aspects of the present concepts.

FIGS. 18A and 18B show a schematic view (FIG. 18A) and a rear-facing view (FIG. 18B) of a body attachment in accord with at least some aspects of the present concepts.

FIGS. 19A-19C show a perspective view (FIG. 19A), a side view (FIG. 19B), and a rear-facing view (FIG. 19C) of the body attachment of FIGS. 18A and 18B in accord with at least some aspects of the present concepts.

FIGS. 21A and 21B show side views of flexible joints of support modules in accord with at least some aspects of the present concepts.

FIGS. 22A and 22B illustrate movements of a modular system with a toddler (FIG. 22A) and velocity profiles of sub-modules (FIG. 22B) in accord with at least some aspects of the present concepts.

FIGS. 23 and 24 show kinematic elements of motion of a modular system in accord with at least some aspects of the present concepts.

Figure 1A:
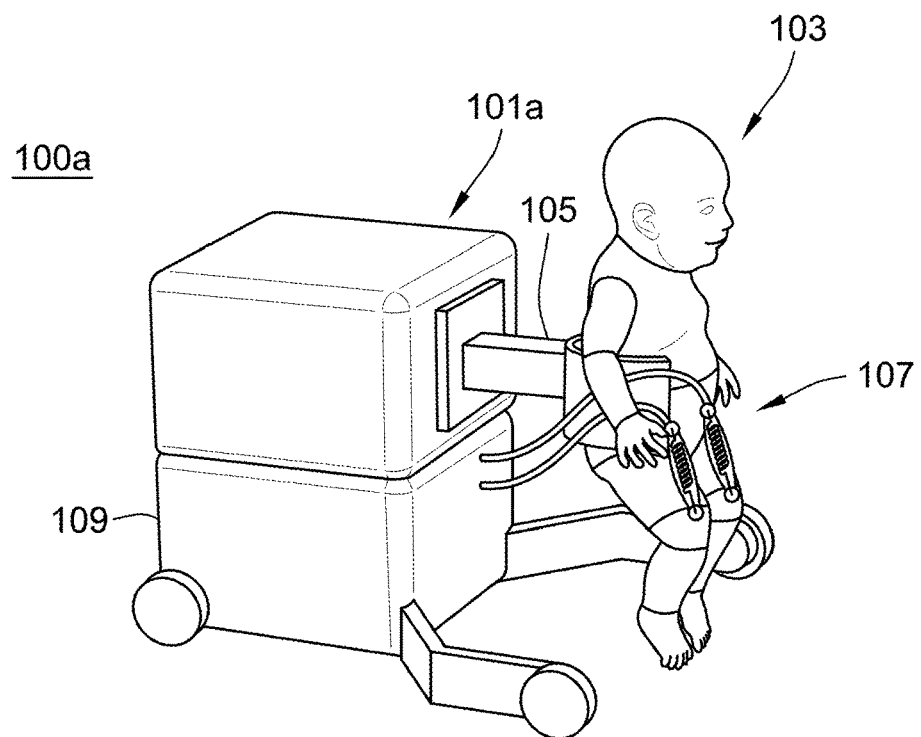
FIGS. 1A and 1B show representations of modular systems in accord with at least some aspects of the present concepts.

While the disclosed aspects are susceptible to various modifications and alternative forms, specific embodiments have been shown by way of example in the drawings and will be described in detail herein. It should be understood, however, that the disclosure is not intended to be limited to the particular forms disclosed. Rather, the invention is to cover all modifications, equivalents, and alternatives falling within the spirit and scope of the disclosure and the appended claims, without limitation.

DETAILED DESCRIPTION OF REPRESENTATIVE EMBODIMENTS

Concepts disclosed herein are directed to a multi-robot (e.g., modular) cyber-physical system, also referred to as a modular system, for assisting mobility-challenged or developmentally challenged persons (e.g., developmentally delayed toddlers, persons suffering from strokes and/or spinal cord injuries undergoing rehabilitation to regain bodily control, etc.) in learning to walk or, in some instances, re-learning to walk. The modular system is a tight conjoining of and coordination between computational and physical resources. The modular system includes multiple robotic devices (or modules) that each address a subtask of motion (e.g., balance, forward propulsion, etc. with respect to walking) As discussed in detail below, disclosed configurations of the modular system help persons lacking in mobility to learn or regain abilities related to motion (e.g., walking) The modular system provides opportunities for a user to explore the body's stability and instability under controlled and safe conditions to explore how the body is used during locomotion (e.g., walking). In part to solve the above-discussed issues for developmentally delayed toddlers, the present disclosure introduces a modular system for assisting a user (e.g., a toddler) in learning to control his or her body to promote and/or develop the ability to walk, preferably with less and less intervention by the modular system over time. The modular system includes a plurality of modules that interoperate both physically and computationally with respect to control of each module to assist a person in exploring how the body is used during locomotion, such as in the context of training and/or re-training a user how to walk, which encompasses the coordination, the stabilization, and the propulsion required to be able to walk. Although a focus in the following disclosure is on promoting and assisting a toddler with walking, the modular system is scalable for use with infants through adults. Further, although a focus of the present disclosure is on a developmental delay, the modular system is applicable to other bases for assisted development, such as a brain injury (e.g., stroke) or other bodily injury unrelated to birth or delayed maturity.

Adults assisting toddlers learning to walk provide various forms of postural support that give the toddlers the opportunity to safely explore the forces acting on their bodies. According to this approach, the modular system provides an explorative safe space in which toddlers can learn and practice to walk. Through a gradual release of support, the modular system provides a toddler with learning opportunities in a manner similar to how the toddler would receive support from adult caregivers, and encourages the toddler to harness the natural passive dynamics of walking (e.g., stance inverted pendulum and swing pendulum). Simultaneously, the modular system provides quantitative longitudinal data on the development of the toddler that can provide guidance on the development of walking.

The modular system includes multiple robotic systems (or modules), with each specific module tailored to address one or more specific subtasks of bodily control relating to stance and/or movement (e.g., walking) Such subtasks include functions and/or acts performed by a user that, in combination, result in the task of walking and/or the ability to be able to walk (e.g., standing upright, under control). The subtasks can pertain to one or more of propulsion, coordination, and stabilization. By way of example, and without limitation, subtasks of propulsion for walking include movement and/or control of the body, and/or elements thereof, that relate to propelling and stopping the body, such as plantar flexion and dorsiflexion moments about the ankle, hip extension and hip flexion moments about the hip, the use of these moments to move the limbs against gravity, harnessing the passive dynamics of gait for more efficient walking, movements of the upper extremities that create complimentary inertia moments for the lower extremities, and the control over the center of mass (COM) during the standing to walking and walking to standing transitions.

Further, by way example, and without limitation, subtasks of coordination include timing of gait events, activating correct muscle groups for specific movements, accounting for the forces and moments that the motion of one body segment causes on other segments, and synchronizing the timing of the loading and unloading of weight to the movements of extremities.

Further, by way of example, and without limitation, subtasks of stabilization include stabilizing the body, and/or elements thereof, about one or more bodily planes, such as controlling medial-lateral stability and posterior-anterior stability and range of sway/oscillation in each plane, and controlling the COM during the standing to walking and walking to standing transitions. For limbs, stabilization subtasks include co-contraction of muscles to modulate joint stiffness.

The modular system leverages a division of labor for the learning of, for example, two tasks: (1) guiding the behavior of the body (e.g., legs) in a gravitational field to harness the mechanical properties of the body (e.g., legs as pendula during walking), and (2) redirecting the body's center of mass (COM) so that the COM moves forward while maintaining medial-lateral and anterior-posterior stability. Each module can interoperate in close collaboration with the other modules via a high-level, shared control system that ensures that the assistance from each module is coordinated such as to maximize the benefit to the user. Additionally, each module can operate independent of the other modules depending on the desired assistance and level of control.

According to the above principles, the modular system can be used to supplement and/or inform clinical therapy, and the modular nature of the system means that at any time, a human (such as a physical therapist or a parent) may substitute for one or more modules of the modular system to provide therapeutic interventions, while the modules continue to perform specific module-based tasks (e.g., gait assistance, sensing, etc.). Moreover, specific modules of the system are able to mimic specific functions of what a human (such as a physical therapist or a parent) would do in helping the user to learn to walk. The use of the modular system allows for therapeutic interventions to be provided with less effort and in a more controlled manner, as compared to human intervention, both within a clinical and a home environment. The use of the modular system can also allow therapeutic interventions typically available only in clinical settings to be continued in a home environment. Further, the quantitative data (e.g., information) gathered by the modular system not only aids control, but also provides a log of information that can be used to assess performance during a therapeutic session and track the progress of the user across various timescales to compare performance over time and inform further decisions regarding therapy or rehabilitation.

Adverting to FIG. 1A, a modular system 100a according to an embodiment of the present concepts includes a support module 101a configured to modulate the COM of a toddler 103 and stabilize medial-lateral and anterior-posterior sway during movement of the toddler. Modulation of the COM can be considered as modulation with respect to the entire body. Alternatively, or in addition, modulation of the COM can be with respect to modulation of specific body parts and/or regions, such as modulations of the pelvis, lower body, upper body, etc., which affect the body's COM. As illustrated in FIG. 1A, the support module 101a, according to some embodiments, can include an arm 105 for interfacing with the toddler 103. The modulation of the support module 101a can occur continuously (e.g., in real-time), periodically, or on demand, depending the requirements and needs to the toddler and the desired assistance to be provided. As discussed in detail below, the support module 101a includes a distinct controller configured to control aspects of the medial-lateral and anterior-posterior support provided by the arm, in addition to receiving one or more control inputs from a high-level controller of the modular system 100a.

The modular system 100a further includes a soft, flexible exosuit 107 worn by the toddler 103. The flexible exosuit 107 includes embedded actuation and sensing functionality that can monitor and assist movement of the toddler 103. By way of example, and as described in detail below, such assistance includes forces promoting stance push off and swing flexion with respect to the legs of the toddler 103. The embedded actuation and sensing functionality also allows the flexible exosuit 107 to provide information for the development of timing of body movements, and to provide resistive or antagonistic moments for further development of stabilization and propulsion. The flexible exosuit may comprise, for example, the flexible exosuit disclosed in PCT/US2013/060225, PCT/US2014/040340, and PCT/US2014/068462, which are each incorporated by reference herein in its entirety.

The modular system 100a further includes a mobile base 109 that carries the components of the modular system 100a so that the user (e.g., toddler 103) does not have to carry the additional weight of the modular system 100a. The mobile base 109 carries the top-level controller for the modular system 100a. According to some embodiments, the mobile base 109 also carries the control systems for each separate module (e.g., support module 101a, flexible exosuit 107, and mobile base 109); however, in alternative embodiments, each module can separately carry the respective controller. The mobile base 109 can include further elements, such as batteries to power the system, one or more power sources for the flexible exosuit 107, such as a pressure source for pneumatic actuators or an electrical power source (AC or DC) for electro-mechanical actuators, in addition to one or more sensors, such as proximity sensors, motion sensors, etc. According to some embodiments, the mobile base 109 is configured to passively or actively move with the toddler 103 as the toddler walks forward. Accordingly, the mobile base 109 includes one or more controllers and one or more sensors (e.g., proximity sensor) that determine the location and movement of the toddler 103 so that the mobile base 109 can actively follow the toddler 103 independent of sensors associated with other modules that may be on the mobile base 109.

Although the mobile base 109 is illustrated by way of example herein as a wheeled cart, the mobile base 109 may comprise any form of mobile base including, but not limited to a rail-based, gantry-based or supported structure. In at least some aspects, the mobile base 109 can be configured to provide additional support for the toddler 103, or the potential for additional support to the toddler 103, such as in the form of a structure or members surrounding the toddler 103 that the toddler 103 may grasp for leverage and support.

Figure 1B:
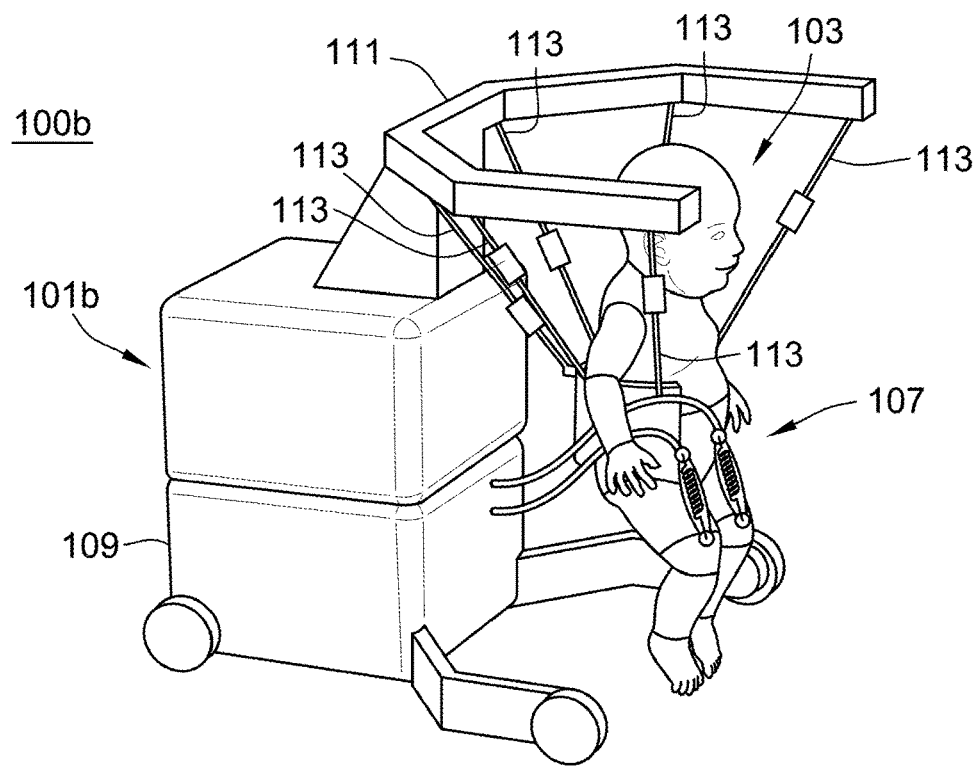

FIG. 1B shows an alternative modular system 100b in accord with aspects of the present concepts. The modular system 100b includes the flexible exosuit 107 and mobile base 109 illustrated in FIG. 1A. However, the modular system 100b includes a support module 101b in place of the support module 101a. The support module 101b includes a scaffold 111 that interfaces with the toddler 103 via multiple tethers 113. Like the support module 101a, the scaffold 111 and the tethers 113 of the support module 101b function together to modulate one or more limbs, one or more body segments and/or the COM of the toddler 103 and stabilize medial-lateral and anterior-posterior sway, as described in detail below. In at least some aspects, the tethers 113 include sensors that determine the direction and the magnitude of the forces of the child's body COM, such as according to those in "Design of a Cable Driven Arm Exoskeleton (CAREX) for Neural Rehabilitation," Mao, Y. and Agrawal, S. K., IEEE Transactions on Robotics, Vol. 28, No. 4, 2012, 922-931, and as described in "Force adaptation in human walking with symmetrically applied downward forces on the pelvis," V. Vashista et al., IEEE Transactions on Neural Systems and Rehabilitation Engineering, 21(6), 969-978 (2013), the entirety of each of which is herein incorporated by reference. The tethers 113 can further include actuators that apply forces to stabilize the toddler's body sway to keep the toddler safely upright at all times. The actuators can selectively relax the forces to give the toddler an opportunity to safely explore body motion.

Figure 2:
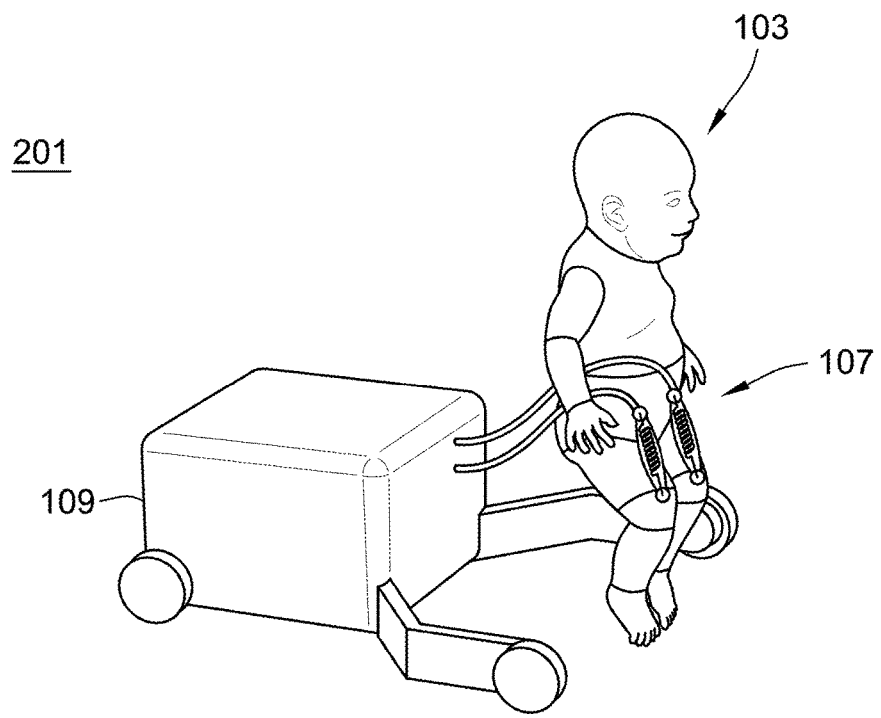
FIG. 2 shows an alternative and/or modified modular system according to at least some aspects of the present concepts.

According to another embodiment, FIG. 2 shows a modular system 201 in accord with the present concepts. The modular system 201 may be a separate and distinct modular system as compared to the modular systems 100a and 100b. Alternatively, the modular system 201 is the modular system 100a or 100b modified such that modular system 201 does not include a support module (e.g., support module 101a or 101b). In such an embodiment, the modular system 201 evidences the modularity of the system in that the support module 101a or 101b can be removed if the user (e.g., toddler) does not require, or no longer requires, the functionality provided by the support module 101a or 101b.

Based on the modularity, the modular systems 100a, 100b, and 201 (referred to generally as modular system 100) can direct the toddler's attention to one specific task at a time, such as stabilization or forward propulsion, while reducing the demands for other tasks, which is in accord with the natural progression of learning to walk. That is, learning to walk is simplified for the toddler because one or more modules may provide a set threshold or percentage of support (e.g., maximum support) for one task (e.g., by providing maximum medial-lateral stability) while different or the same one or more modules provide a different set threshold or percentage of support (e.g., minimal support) for another task, which allows the child to focus on the other task (e.g., learning to step for forward propulsion). Based on this specific-task focus, a toddler can develop and master a task prior to working on other tasks, rather than having to develop all tasks simultaneously. The assistance provided by the modular system can be tailored to each individual by removing one or more modules, as well as tuned by continuous, periodic, or on demand adjustments of the assistance provided by each module. The assistance provided by each module can also progress at different rates from one another, which allows for the modular system 100 to be tailored for an individual's needs.

The modular system 100 works on several timescales for the development of motion (e.g., walking) of the toddler. According to one timescale, the modular system 100 receives real-time inputs from sensors located throughout the various modules and/or sensors disposed externally thereto (as well as the modular system 100 as a whole) and controls the system to stabilize and/or propel the toddler to develop the toddler's motion. According to a second timescale, the modular system 100 stores longitudinal data regarding the toddler's development for analysis by a user (e.g., physician, clinician, technician, caregiver, parent, guardian, etc.) to monitor and adjust performance characteristics of the modular system 100 for continued progression and development of the toddler.

The choice of module(s) used is typically based on the requirements of the toddler to provide tailored assistance, as needed. According to some embodiments, maximum assistance utilizing all three modules can be provided. Alternatively, partial support utilizing only one or two of the modules can be provided. Different toddlers with different levels of debility and/or ability may use different configurations of the modular system 100. In addition, as the user improves his or her walking, modules of the modular system 100 can be individually adjusted over time to scale back assistance and match the user's developmental progress. The adjustments or tuning can be automatic or manual. Manual adjustments may be made by a user monitoring the progress, such as a physician, clinician, technician, parent, or guardian. Automatic adjustments may be made by the controllers within the modular system 100. The automatic adjustments can be based on sensors within the modular system 100 monitoring in real-time, or over the course of therapeutic treatment, the state of the system 100 and determining if the behavior of the user is correct or not based on threshold parameter values that relate to normal or typical walking or subtasks of walking Such parameters are based on, for example, gait kinematics during locomotion, which include joint angle and acceleration measurements, as well as spatial-temporal measures such as step length, step width, and cadence, and are determined based on, for example, gyroscopes, inertial measurement units (IMUs), encoders, foot switches, and/or hyper-elastic soft strain sensors across joints. Based on the parameter values, the modular system 100 instructs the actuation appropriately.

By way of example, based on the information from sensors within the modular system 100, controllers within the modular system 100 respond to developmental changes in behavior of the body's COM, behaviors in one or more limbs and/or body segments, and in gait parameters by allowing greater relaxation of media-lateral and/or anterior-posterior sway, and by reducing, and eventually eliminating, forces provided by the modular system 100, such as from the flexible exosuit for hip and/or ankle torques. Moreover, based on the dynamic nature of the modular system 100, at any time a human (such as a physical therapist or a parent) may substitute for one or more functions of the modular system 100 to provide therapeutic interventions. The modules of the modular system 100 can dynamically respond to the interventions by continuing to provide and modify therapeutic intervention with respect to the other functions.

Alternatively, or in addition, as the user develops one or more subtasks of walking, the user may no longer need the assistance provided by one or more modules. For example, the user may have developed medial-lateral and anterior-posterior stability control such that assistance provided by the support module is no longer required. The user may be able to walk independently from the support module while wearing the soft exosuit for support and propulsion, as needed. Based on the user's development, one or more modules are removed from the modular system 100.

FIGS. 3A through 3C illustrate the above-described modularity with respect to a modular system 300 in accord with aspects of the present concepts. As shown in FIG. 3A, the modular system 300 initially can include a mobile base 301, such as in the form of a cart, a flexible exosuit 303, including a pressurized tank 303a for actuation of one or more pneumatic elements of the flexible exosuit 303 or, in other aspects, an electrical source for actuation of one or more electro-mechanical actuators (not shown in FIGS. 3A-3C), and a support module 305 in the form of a tethered scaffold. According to the modular system 300, the toddler 307 can begin modular-system-assisted development with maximum assistance from all three modules (e.g., mobile base 301, flexible exosuit 303, and support module 305).

As the toddler progresses in the development of walking, the modular system 300 can be tailored to match the toddler's progression and promote further progression. FIG. 3B shows a modification to the modular system 300, such as removal of the support module 305. The support module 305 can be removed as, for example, progression evidenced by the longitudinal data indicates that the toddler 307 no longer needs medial-lateral and/or anterior-posterior support. Such progression may be evidenced by the width of the toddler's gait being less than a threshold width, which indicates medial-lateral stability. The modular system 300 continues to provide active assistance from the flexible exosuit 303 and passive support provided by the toddler 307 being able to hold onto the mobile base 301.

As shown in FIG. 3C, as the toddler 307 continues to demonstrate progression in walking, the mobile base 301 can be removed, leaving only the flexible exosuit 303. Such progression can be demonstrated, for example, by the toddler 103 making minimal or no contact with the mobile base 301 for support or for balance. Such progression can be detected, for example, by one or more contact sensors on the mobile base 301 detecting minimal or no contact by the toddler 103 during walking Ultimately, the goal is for the toddler 307 to progress to the point where the flexible exosuit 303 is no longer needed and the toddler is able to walk independently of all of the modules/modular system 300. By way of example, as the user demonstrates the application of forces and/or motions of a leg like an inverted pendulum, or swings the leg forward like a pendulum in anticipation of redirecting the COM with another heel strike, the flexible exosuit 303 is further tuned or removed entirely from the modular system 300.

Modification of the modular system 300 is based on progression of the user in developing the ability to walk. Such progression is evidenced based on data collected during the course of therapeutic assistance provided by the modular system 300 indicating improvement in one or more subtasks of walking. The data can be collected with respect to one or more parameters that quantify the subtasks of walking, or walking in general. By way of example, and without limitation, the one or more parameters include cadence (e.g., steps per minute), stride time, stride length, step width, duration of double support (e.g., both feet contacting ground), joint angles and accelerations, the overall forward walking speed achieved by the toddler, the ratio of weight the user is placing on the support module vs. supporting themselves, the frequency of the toddler's coordination "errors" detected by the system, etc.

By way of example, after several successive assisted steps in which propulsive force is added at heel strike, the pattern of accelerations and decelerations within the footpath boundaries may become increasingly stable. Further, gait parameters may exhibit greater stride length and narrower step width, which indicate more controlled, mature walking. These changes in the walking behavior of the user evidence the user's development and can result in the tuning and/or removal of one or more modules of the modular system 300.

Figures 4A, 4B:
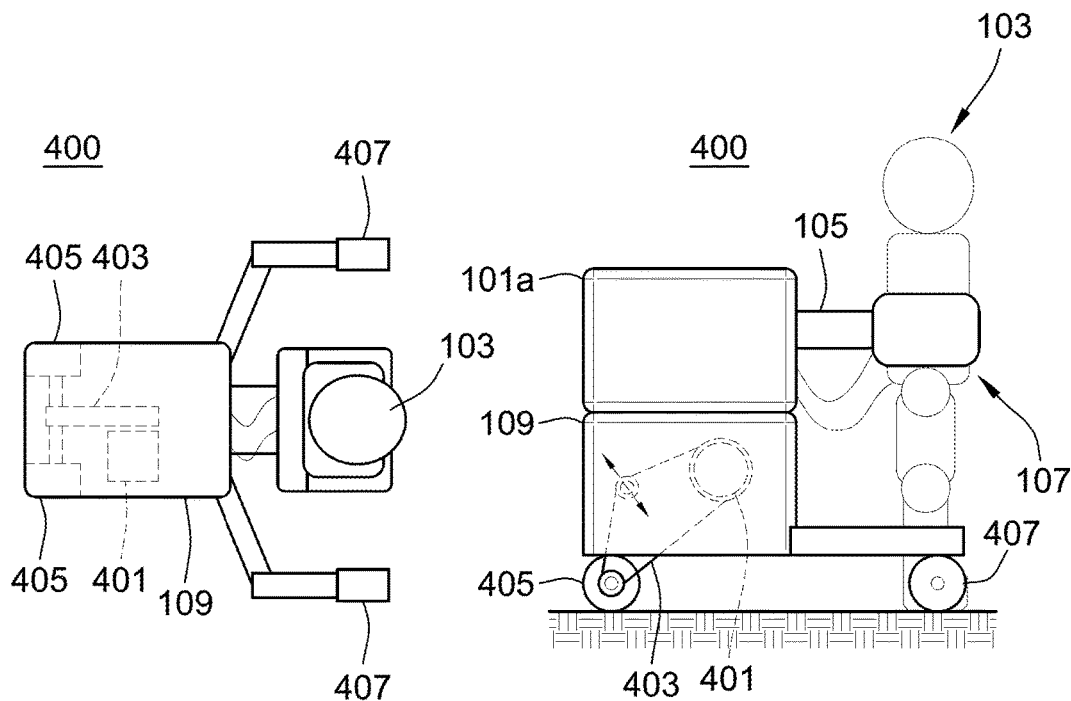
FIGS. 4A and 4B show a top view (FIG. 4A) and a side view (FIG. 4B) of a modular system in accord with at least some aspects of the present concepts.

As discussed above, the mobile base of a modular system 100 is configured to be passive, such that the mobile base follows the toddler under power provided by the toddler (e.g., pulling the mobile base). Alternatively, the mobile base is configured to actively follow the toddler under self-powered assistance. In doing so, the mobile base is configured to dynamically estimate the relative position, velocity, and acceleration between the mobile cart and the toddler. In at least some other aspects of the present concepts, a controller of the mobile base further utilizes the sensor(s) of the modular system 100 to ascertain predictive signals corresponding to movement (i.e., sensing the toddler's intent to actively control one or more motion systems (e.g., sensing of muscle activation, etc.)) to follow the toddler. In the case of the modular system 100a being actively powered to follow the toddler 103, FIG. 4A shows a top view, and FIG. 4B shows a side view, of the elements of the modular system 101a that actively power the system in accord with concepts of the present disclosure. The mobile base 109 includes a motor 401 that powers the movement of the mobile base 109. The motor 401 is connected to, for example, a timing belt/pulley arrangement 403 that rotates drive wheels 405. The forward section of the mobile base 109 is supported by free wheels 407.

Operation of the motor 401 drives the drive wheels 405 to move the mobile base 109 and the modular system 101a forward to actively and dynamically follow the movement of the toddler 103. In at least some aspects, the mobile base 109 includes one or more sensors, such as a proximity sensor and a motion sensor, to determine the position and motion of the toddler. Alternatively, information from one or more elements located throughout the modular system 100a, or external to the modular system, is fed to a controller of the mobile base 109 to dynamically follow the toddler.

A focus for control of the modular system 100a and, indeed, a modular system 100 in general, is the toddler's COM. The COM can be considered a compression of the many biomechanical degrees of freedom of the toddler's body into a single lower dimensional form. As such, the COM of the toddler's body is information available to both the child and the modular system 100 for the stabilization and coordination of body movement. By way of example, the modular system 100 can model COM behavior as the toddler learns to walk by considering each leg during a single support phase of the gait cycle as an inverted spring-pendulum system. During a double support phase, the modular system 100 models the COM behavior as a redirection of body motion as a consequence of transitions between single-support phases. Sensors within the modular system 100 detect information that is processed to determine and monitor the state of the toddler and understand if the behavior of the toddler is correct or not and instruct the actuation appropriately in a closed-loop manner.

According to a single support phase of posterior-anterior oscillations, the toddler can be considered as an inverted pendulum and during the swing phase the leg can be considered as a pendulum. The potential and kinetic energy can be monitored and used as part of the control scheme to help guide the user to a more natural human walking pattern that leverages the natural passive dynamics of the body and limb. During walking, each transition to a new stance leg requires redirection of the COM velocity from one inverted pendulum to the next. In other words, walking consists of an inverted pendulum phase for one leg, a step-to-step-transition phase, and an inverted pendulum phase for the other leg. By using sensors to monitor the movement of the body and limbs, a top-level controller of the modular system 100 interoperates with and directs controllers of one or more of the modules (e.g., flexible exosuit, support module, and mobile base) to assist in the manipulations of the COM, while promoting stabilization and support.

Within the modular system 100, a focus of specific body motion and control of self-propelled forward motion is with respect to the flexible exosuit (e.g., flexible exosuit 107). As discussed above, the flexible exosuit is a soft, lightweight, flexible, and wearable garment worn by the toddler, which serves as an interface for the modular system 100 to apply forces and/or torques to the toddler's body. Application of these forces and/or torques can be at (or across) various different joints of the toddler, such as at the hip, the knee, the ankle, etc. At each one of the locations, various forces and/or torques can be applied for different orientations/functions (e.g., flexion, extension, abduction, adduction, etc. with respect to the hip).

The benefits of the forces and/or torques applied by the flexible exosuit are multifold. In at least some aspects, the forces and/or torques applied by the flexible exosuit are used to provide an instructive and/or coordinating cue for the toddler to move a limb. In at least some aspects, the forces and/or torques applied by the flexible exosuit are used to provide assistance to movement if the toddler lacks the strength, or enough strength, to perform the movement without assistance. In at least some aspects, the forces applied by the flexible exosuit are used to modulate joint stiffness to help the toddler achieve correct limb behavior.

Specific applications of forces and/or torques by the flexible exosuit can affect limb behavior in different ways. According to one application, the flexible exosuit can create a moment about one or more joints by applying a force across a joint between a limb segment on one side of the joint (e.g., a distal segment) and a limb segment on another side of the joint (e.g., a proximal segment). The moments assist a motion when the moments compliment the natural moments created by the user for the motion. The moments can also resist or modulate joint stiffness when the moments oppose the natural moments created by the user. With respect to antagonistic moments, the flexible exosuit is configured to control the joint stiffness through co-contraction of one or more actuation units within the flexible exosuit that create antagonistic moments that resist natural moments created by the user. The flexible exosuit selectively achieves these various results by transferring forces and/or torques along load paths emulating real-life arrangements of muscles, tendons, and ligaments.

According to one embodiment, the flexible exosuit is worn on the toddler's legs like clothing. In some aspects, the flexible exosuit can be anchored at the hips and/or waist of the toddler, and extend to above, at, or below the toddler's knees. Alternatively, the flexible exosuit can include a lower leg and/or ankle component, which extends past the knee and interfaces with the lower calf and/or ankle.

When actuated, the flexible exosuit can provide forces (e.g., assistive and/or resistive) to help the toddler learn, for example, that a leg can either serve to propel the COM forward like an inverted pendulum, or swing the leg forward like a pendulum in anticipation of redirecting the COM with another ground contact.

In addition to the above-described actuation, the flexible exosuit acts as a sensory platform. That is, the flexible exosuit can have integrated sensing to monitor toddler motion with respect to, for example, joint angles, gait events, etc. The information collected by the sensors about the flexible exosuit can be used both for control and for monitoring performance (e.g., longitudinal data with respect to development and growth), in addition to detecting and avoiding abnormal joint motions that could cause sprain or other injury.

By way of example, the flexible exosuit can contain integrated sensing that provides information, such as joint angle measurements, that can be inputted into the top-level controller of the modular system for the control of the system, in addition to being a source of quantitative longitudinal data that can be provided to a user (e.g., physician, clinician, technician, etc.) to evaluate the toddler's walking.

Like the flexible exosuit itself, the sensor(s) can comprise flexible or unobtrusive sensors, such as elastomer-based hyper-elastic strain sensors. By way example and without limitation, some exemplary sensors are disclosed in publications WO 2013/044226 A2, WO 2012/103073 A2, WO 2012/050938 A2, and U.S. Pat. No. 8,316,719 B2, and applications PCT/US2014/068462 and PCT/US13/66034, each of which is hereby incorporated by reference in its entirety. For example, one or more hyper-elastic strain-sensors may comprise a stretchable silicone rubber sheet with one or more conductive-liquid-filled micro-channels provided to measure a change in electrical resistance when the sheet is stretched. In addition, or alternatively, the sensors can include gyroscopes, which can detect certain peaks that correspond to specific gait events, foot switches which detect heel strike, toe-off, or other foot contact events, encoders or potentiometers on the joints that give joint angle measurements, and/or inertial measurement units (IMUs) that provide absolute coordinate measurements. Information provided by strain sensors and IMUs, such as strain and inertial data, can be used, alone or in combination, to further refine the estimation of joint kinematics during locomotion.

Actuation within the flexible exosuit can be achieved according to one or more different techniques. According to a first technique, the flexible exosuit includes soft actuators that utilize soft elastomeric synthetic muscles and sensors. By way example and without limitation, some exemplary soft actuators are disclosed in publication WO 2013/033669 A2, which is hereby incorporated by reference in its entirety. According to some embodiments, the soft actuators include miniaturized pneumatic muscles, artificial tendons and/or ligaments, and hyper-elastic strain sensors in successive layers. Multiple pneumatic muscles within a single soft actuator allow the actuator to behave according to specific contractions, such as simultaneous contraction, sequential contraction, or bending. The artificial tendons and ligaments can constrain motion of the soft actuators according to specific directions that can be aligned to biological muscles and tendons to create the same muscle contraction effects. The soft actuators can be lightweight, flexible, and impact-resistant so as to not weigh down or impede the natural motion of a toddler. Such properties make the soft actuators particularly applicable to wearable application for toddlers.

The soft actuators can be configured and located about the flexible exosuit to apply the above-described forces and/or pressures. According to some embodiments, the soft actuators can be shaped to conform to one or more body segments, such as the leg, the hip, the thigh, the arm, the elbow, the calf, the ankle, etc. According to some embodiments, a combination of modular soft actuators can be configured and located about the user to form the flexible exosuit. Such soft actuators may be bending soft actuators, such as those placed at a joint and configured to bend according to the natural movement of the joint. Such soft actuators may alternatively, or in addition, be linear soft actuators that apply forces at distal and/or proximal ends of limbs.

The soft actuators can be actuated by a fluid, such as by increases/decreases in the pressure of a gas or a liquid. The pressure source that drives the fluid is advantageously located off of the flexible exosuit, such as on the mobile base, and may comprise, for example, an air pump or a compressed air tank. Alternatively, the pressure source that drives the actuators of the flexible exosuit can be integrated on the flexible exosuit, or on a standalone component worn by the user or pulled alongside the toddler (e.g., pressurized tank). In applications of toddlers, the pressure source is located off board on the mobile base to minimize the added weight on the toddler.

One possible method of actuation is to place bending soft actuators on the joint to induce flexion when actuated. An alternative to bending actuators are linear actuators, such as pneumatic artificial muscles (PAMs), which contract/shorten in length when pressurized.

With respect to PAMs, as an example, PAMs allow for the flexible exosuit to create moments about selected joints. These moments can be used to create perturbations and/or impulses that act as cues for the toddler as they progress through the gait cycle. The moments can also provide power assistance for developmentally-delayed toddlers who lack the motor strength for normal walking. If the PAMs are placed in an antagonistic configuration, the moments generated by the flexible exosuit can also modulate joint stiffness through co-contraction.

Figure 5A:
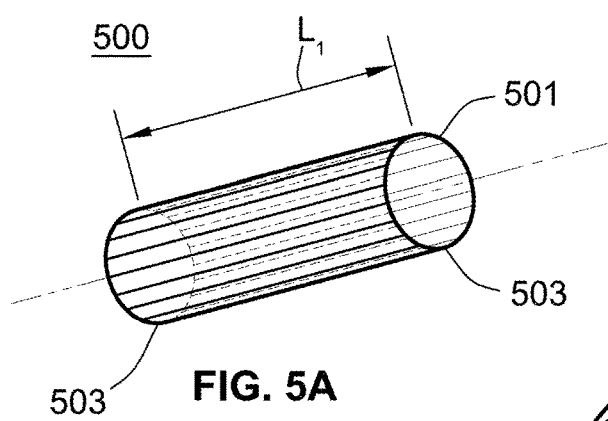
FIGS. 5A and 5B show actuation states of an actuator of a flexible exosuit within a modular system in accord with at least some aspects of the present concepts.
Figure 5B:
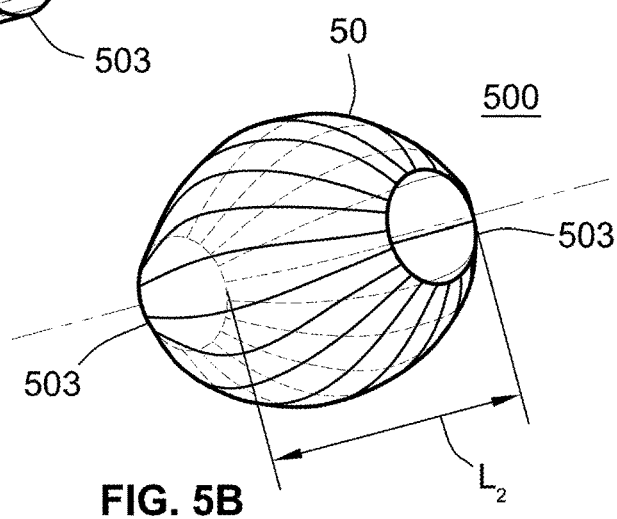

FIGS. 5A and 5B illustrate the geometric configuration of an exemplary PAM 500. As illustrated in FIG. 5A, the PAM 500 includes an inextensible sheet 501 of woven fibers in the shape of a cylinder when in a relaxed, non-actuated state.

However, the shape of the inextensible sheet 501 may vary without departing from the scope of the present disclosure. Although not shown (for illustrative convenience), the PAM 500 includes an inflatable material surrounded by the inextensible sheet 501. In the non-actuated state, the inextensible sheet 501 may have a length $L_1$, such as 42 mm.

Upon actuation, a fluid causes the inflatable material to inflate. Inflation of the inflatable material causes the inextensible sheet 501 to contract lengthwise as it expands radially at the center, as shown in FIG. 5B. The contraction causes the length of the inextensible sheet 501 to reduce to $L_2$ (i.e., $L_2<L_1$). The reduction in length of the inextensible sheet 501 from $L_1$ to $L_2$ applies a contractile force between the ends 503 of the PAM 500. When the PAM 500 is connected between two elements, such as anchors within the flexible exosuit attached at specific points about the toddler's body, the PAM 500 applies a contractile force between the elements.

Figure 6A:
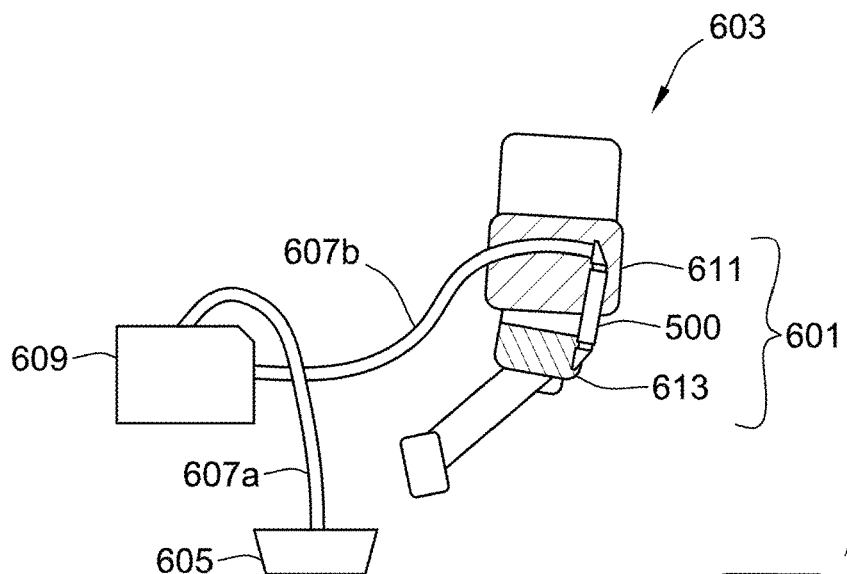
FIGS. 6A and 6B show assistance provided by a flexible exosuit of a modular system in accord with at least some aspects of the present concepts.
Figure 6B:
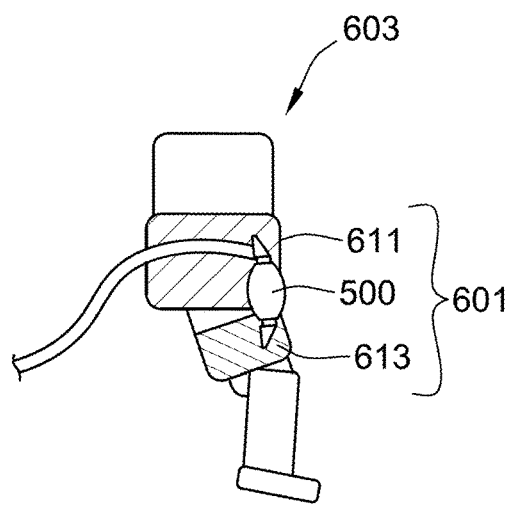

FIGS. 6A and 6B illustrate the placement of the PAM 500 within a flexible exosuit 601 to apply a contractile assistive force on a toddler 603, in accordance with the present concepts. Specifically, the PAM 500 is connected to a flexible exosuit 601 at the hip of the toddler 603. The PAM 500 is connected to a power source 605, such as a compressor, through pressure lines 607a and 607b and a mobile base 609. Although illustrated as two separate elements, the power source 605 can be located within the mobile base 609.

In a non-actuated state, the PAM 500 is in a straight configuration, as illustrated in FIG. 5A. When actuated, the PAM 500 contracts into a generally spherical shape, as illustrated in FIG. 5B. The contraction of the PAM 500 located at the hip of the toddler 603 induces hip flexion. The amount of the contraction of the PAM 500 (e.g., $L_1$-$L_2$), in addition to the speed at which the PAM 500 contracts, controls force applied through the flexible exosuit for the hip flexion. Such an amount may be small, such as to provide a cue to the toddler 603 for when to flex the hip, or may be large, such as to provide assistance in flexing the hip.

The forces generated by the PAM 500 are transferred through the fabric of the flexible exosuit 601 to the toddler 603 according to anchor points within the fabric and the configuration of the fabric. In FIGS. 6A and 6B, the flexible exosuit 601 can consist of a hip brace 611 located at the hip of the toddler 601, and a cuff 613 located around the lower thigh of the toddler 601. The hip brace 611 provides anchoring of the force generated by the PAM 500 at an area of the toddler 603 that can accept and dissipate large loads. The cuff 613 provides anchoring of the transmitted force across the hip. Although FIGS. 6A and 6B illustrate a single PAM 500, the flexible exosuit 601 may include a plurality of PAMs located about the toddler 603, such as at least one PAM 500 located about each hip.

Figure 7:
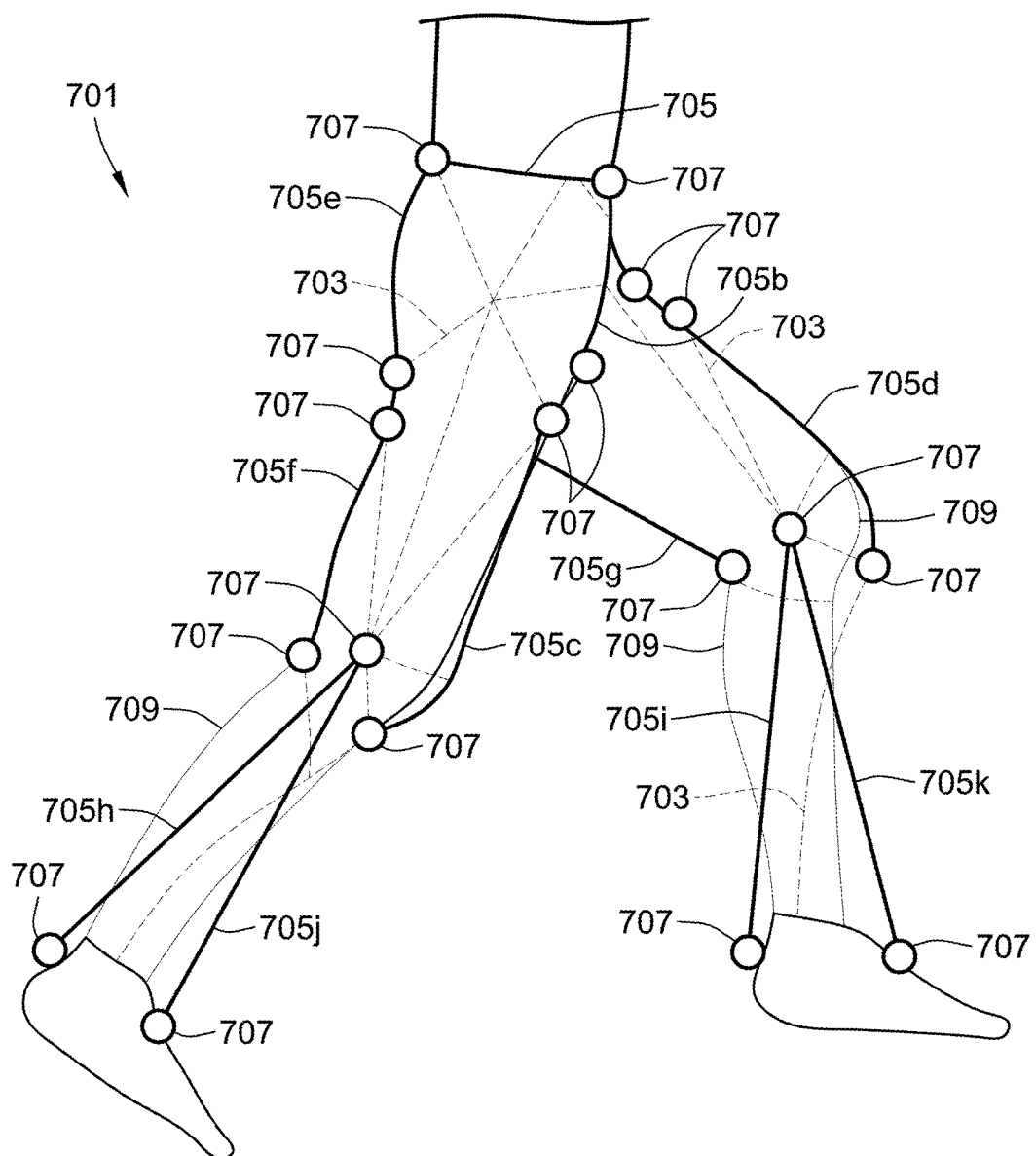
FIG. 7 shows a flexible exosuit worn on lower extremities of a user in accord with at least some aspects of the present concepts.

FIG. 7 illustrates a flexible exosuit 701 made of interconnected straps 703 in accord with aspects of the present concepts. The interconnect straps 703 provide a structural foundation of PAMs 705 located throughout the flexible exosuit 701. The straps 703 are located about the perimeter 709 of the body to support and dissipate the applied forces of the PAMs 705. The PAMs 705 are located about the perimeter 709 of the body to apply forces and/or cues to various locations.

By way of example, PAMs 705a-705d provide hip flexion assistance and/or cues about the hips, PAMs 705e-705g provide hip extension assistance and/or cues about the hips, PAMs 705h and 705i provide plantar flexion assistance and/or cues about the ankles, and PAMs 705j and 705k provide dorsiflexion assistance and/or cues about the ankles. The PAMs 705h-705j connect at one end to anchor points 707 on one or more straps 703 and at the opposite end to anchor point 707s at the foot of the toddler, such as on a shoe, a sock, or a foot plate. According to the illustrated and described arrangement, a variety of assistance and cues can be applied to the toddler during the development of walking.

Rather than applying forces and/or cues with PAMs, according to some embodiments of the present concepts, assistance and/or cues can be provided by cables, such as Bowden cables. Based on a force being transmitted from an off-board power source, such as a drive motor, to an attachment point on the flexible suit, a flexible exosuit may be configured differently than the flexible exosuit of FIG. 7 to dissipate the forces across load paths on the body.

Figure 8:
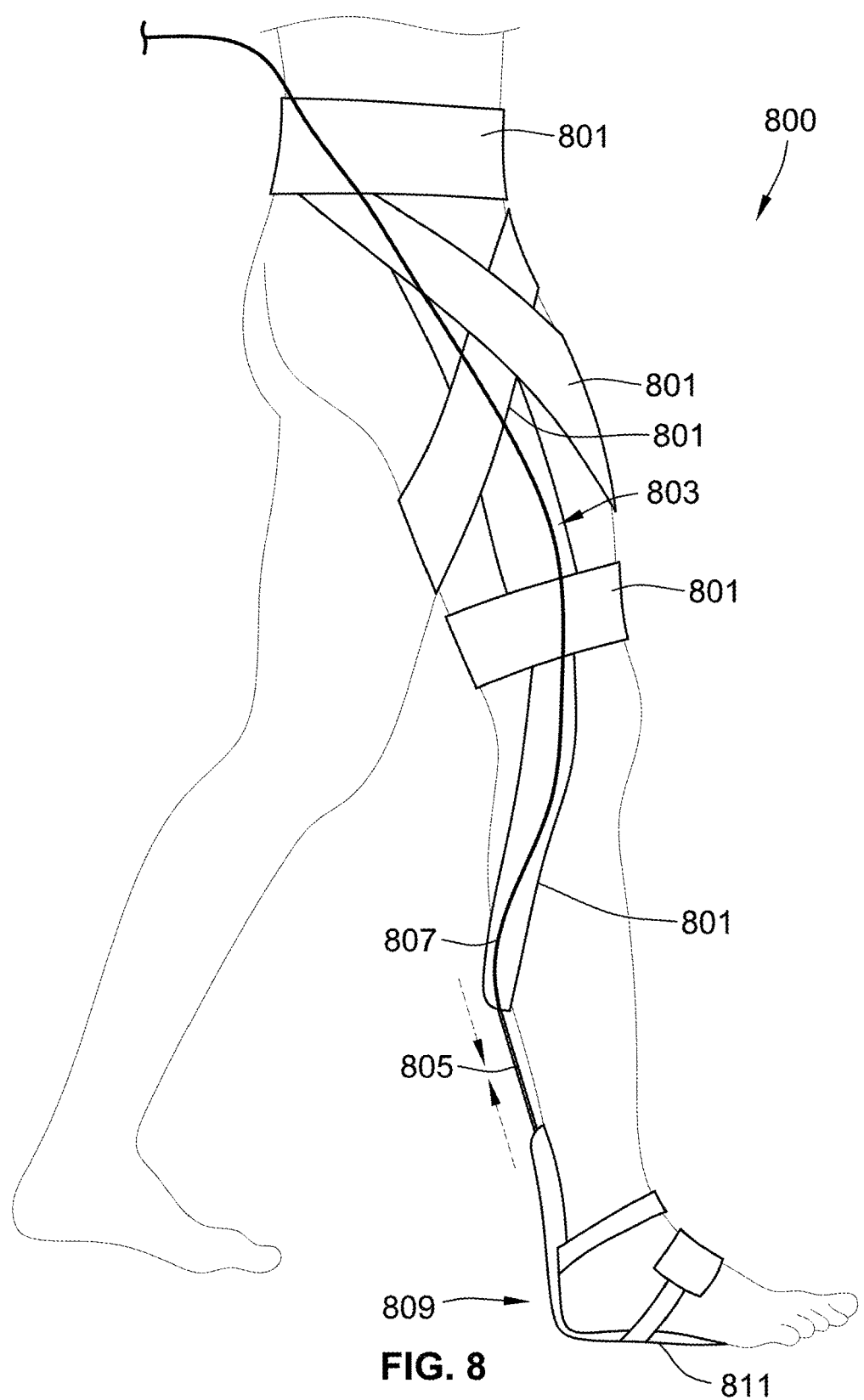
FIG. 8 shows a unilateral flexible exosuit in accord with at least some aspects of the present concepts.

FIG. 8 illustrates a flexible exosuit 800 for supporting transmission of a load path from an off board actuator in accord with concepts of the preset disclosure. As illustrated, the flexible exosuit 800 includes overlapping straps 801. The straps 801 together form the wearable garment of the flexible exosuit 800. In the embodiment illustrated, the straps 801 are worn on one leg (e.g., unilateral flexible exosuit). However, the number and pattern of straps 801 may vary according to the desired type of flexible exosuit and the desired application of assistance and/or cues. By way of example, both legs of the toddler may include a similar pattern of straps 801 to provide a bilateral flexible exosuit.

The straps 801 are connected to Bowden cable 803 (or any other type of force transmission element). The Bowden cable transmits a force generated by an off board power source (e.g., drive motor, not shown) to the flexible exosuit. The drive motor can provide a third of the biological torque required for movement. For a two-year old toddler, exemplary torque may be 2.3 Newton-meters (Nm) for 100 rotations-per-minute. By way of example, a drive motor can be a Maxon EC60 motor, overdriven at 20 amperes (A) with a built-in 1024 CPT encoder and an integrated ESCON controller from Maxon. The Bowden cable 803 includes a cable 805 that is surrounded along at least part of the length of the Bowden cable 803 by a sheath 807. The sheath 807 is attached to one or more of the straps 801 to provide support for and dissipate transmission of the forces on the toddler's body. The cable 805 attaches to a foot attachment 809, such as a shoe, a sock, or a footplate. The foot attachment 809 may include one or more sensors 811, such as a footswitch, an IMU, and/or a gyroscope to detect contact between the foot and the ground or other obstacle.

According to the flexible exosuit 800 illustrated in FIG. 8, assistance and/or cues may be applied from the off board power source to the ankle of the user. Such assistance and/or cues can be for applying a plantar flexion moment about the ankle According to such an arrangement, however, compressive, contractile, and shear forces on the user's body may cause discomfort.

In accordance with additional concepts of the present disclosure, FIG. 9 shows a drive arrangement 900 that includes an architecture that mimics the tendon and ligament structures of the human anatomy to transfer forces to the user while reducing uncomfortable forces, such as shearing forces. The drive arrangement 900 includes a flexible exosuit 901 connected to a flexible exosuit power unit 903. The flexible exosuit power unit 903 can be mechanical, electrical, and/or pneumatic, depending on the configuration of the flexible exosuit 901, and can be located on the mobile base of the modular system to minimize the weight on the user.

The flexible exosuit power unit 903 drives a force transmission element 905. An exemplary force transmission element can be a Bowden cable, which includes a cable within an outer sheath. Within the flexible exosuit power unit 903, a pulley (not shown) can be mounted on the shaft of a motor (not shown). When the motor turns in one direction, the motor applies a force through the force transmission element 905 (e.g., the Bowden cable) and to the flexible exosuit 901. The motor of the flexible exosuit power unit 903 can also rotate in the other direction to feed out slack. According to one embodiment, a slip clutch (not shown) can be between the pulley and motor to provide a safety limit to the force transmission element 905.

In the case of actuating the hip joint, the force transmission element 905 connects to a hip drive unit 907. The hip drive unit 907 converts the linear force applied by the force transmission element 905 to a rotational toque. The rotational torque is applied to the user through a multi-contact, flexible shaft 909 connected to the hip drive unit 901. According to one arrangement, the rotational torque causes hip flexion and/or hip flexion depending on the capabilities and characteristics of the driving arrangement of the force transmission element 905. The linear force of the force transmission element 905 is converted to a rotational torque to avoid a shearing force on the user's skin.

The flexible shaft 909 has a branched multi-contact structure for even and comfortable force distribution along the thigh, rather than a point application of force. The flexible shaft 909 is embedded within a thigh attachment 911. The thigh attachment can be a flexible piece of fabric that further spreads and dissipates the applied force from the flexible shaft 909. The rotational torque of the hip drive unit 907 applied through the flexible shaft 909 and the thigh attachment 911 causes a hip flexion moment at the user's hip, which can provide assistance and/or a cue in developing the user's walking. Alternatively, or in addition, the hip flexion moment can provide resistance, such as in an antagonistic arrangement, during hip extension to modulate joint stiffness. To passively accommodate abduction and adduction motion of the hip, the proximal section of the shaft can have a thin but wide section (not shown) which can easily bend laterally but remain rigid in the flexion/extension direction.

The drive arrangement 900 of the flexible exosuit 901 can be completely transparent to the user when needed to avoid impeding the natural motion of the user. FIG. 10A illustrates an enlarged view of the connection of the force transmission element 905 to the hip drive unit 907, in accord with an embodiment of the present disclosure. In a passive state, slack of the force transmission element 905 is fed out. In the example of a Bowden cable, a length of cable 1003 is fed out relative to the sheath 1005 such that a cable stop 1001 at the end of the force transmission element 905 disengages from a loop 1007 on the hip drive unit 907 through which the cable 1003 passes. The loop 1007 is connected to a pulley 1009 of the hip drive unit 907, which is connected to the flexible shaft 909. In the slack state, the toddler's hip and the flexible shaft 909 connected to the hip drive unit 907 are free to move without any impedance from the force transmission element 905. According to some embodiments, a spring 1011 can be connected to the cable stop 1001 on the distal end of the force transmission element 905 to provide a return force and maintain some tension in the force transmission element 905 during the slack state.

To provide assistance or a cue for the toddler, FIG. 10B illustrates the force transmission element 905 in an actuated state, in which the cable stop 1001 engages and applies pressure to the pulley 1009 of the hip drive unit 907 at the loop 1007. When the cable 1003 of the force transmission element 905 retracts far enough (as shown in FIG. 10B), the cable stop 1001 engages the loop 1007 and rotates the pulley 1009 of the hip drive unit 907, in addition to the flexible shaft 909 connected to the hip drive unit 907, and causes assistance and/or a cue for the toddler wearing the flexible exosuit 901.

FIGS. 11A and 11B illustrate another embodiment of a hip drive unit 1100, in accord with concepts of the present disclosure. Specifically, FIGS. 11A and 11B illustrate a compact, low-profile hip drive unit 1100. The hip drive unit 1100 of FIGS. 11A and 11B also provides a predictable engagement between an actuated force transmission element, such as a Bowden cable, and a flexible shaft attached to the hip, such as the flexible shaft 909.

Adverting to FIG. 11A, the hip drive unit 1100 includes a pulley 1101 and a thigh shaft 1103 (FIG. 11B) that rotate about a post 1005 that extends from a support plate 1107. According to some embodiments, the thigh shaft 1103 can connect to the flexible shaft 909, or the flexible shaft 909 can connect directly to the hip drive unit 1100 and rotate about the post 1105. The support plate 1107 can be affixed to the toddler in a wearable manner, such as part of a belt or waistband. The support plate is mounted in such a way so as to absorb counter-torque to distribute forces more evenly and comfortably (e.g., a rigid extension in the rear which braces against the lower back, with padding for comfort; fabric straps bracing against other sections of the body; integrated stiff paths in the belt/waistband fabric which prevent it from stretching and twisting in the direction caused by counter-torque). In a non-actuated state, the pulley 1101 and the thigh shaft 1103 are free to rotate with respect to each other about the post 1105.

The pulley 1101 includes a protruding peg 1109 that engages the thigh shaft 1103 if the pulley 1101 rotates far enough counterclockwise. The peg 1109 provides a predictable engagement between the movement and engagement of the pulley 1101 with the shaft 1103. Within the pulley 1101 is a torsional spring 1111. When the force transmission element 1203 (FIG. 12) is in a slack state, the torsional spring 1111 actuates the pulley 1101 so that the resting position of the pulley 1101 is such that the peg 1109 is not engaged with the thigh shaft 1103, and the thigh shaft 1103 is free to move.

The pulley 1101 further includes a slot 1113 and a recess 1115 that accept an end of a force transmission element (e.g., force transmission element 1203). Specifically in the example of a Bowden cable, the slot 1113 accepts the cable, and the recess 1115 accepts a cable stop to lock the Bowden cable within the pulley 1101.

Figure 12A:
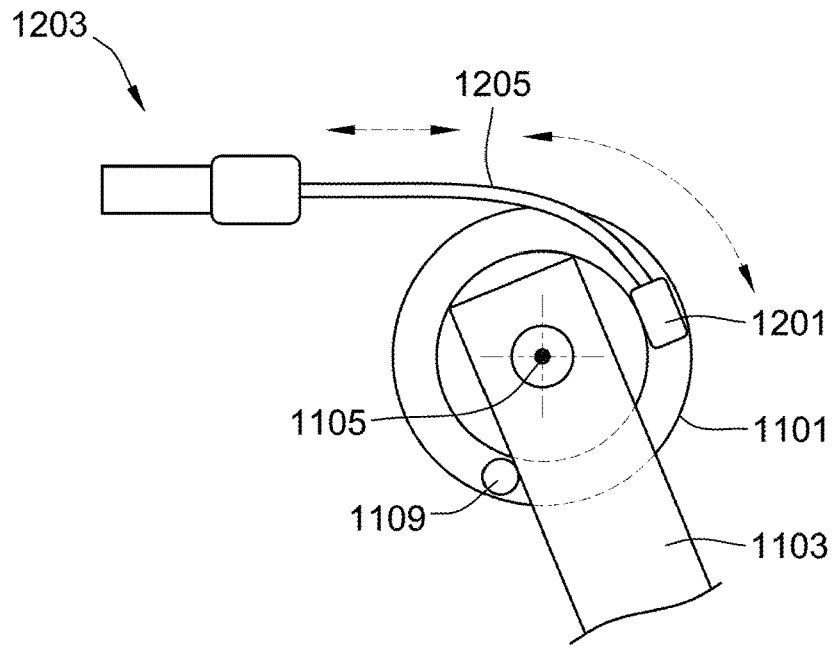
FIGS. 12A and 12B show detailed side views of hip drive units in accord with at least some aspects of the present concepts.
Figure 12B:
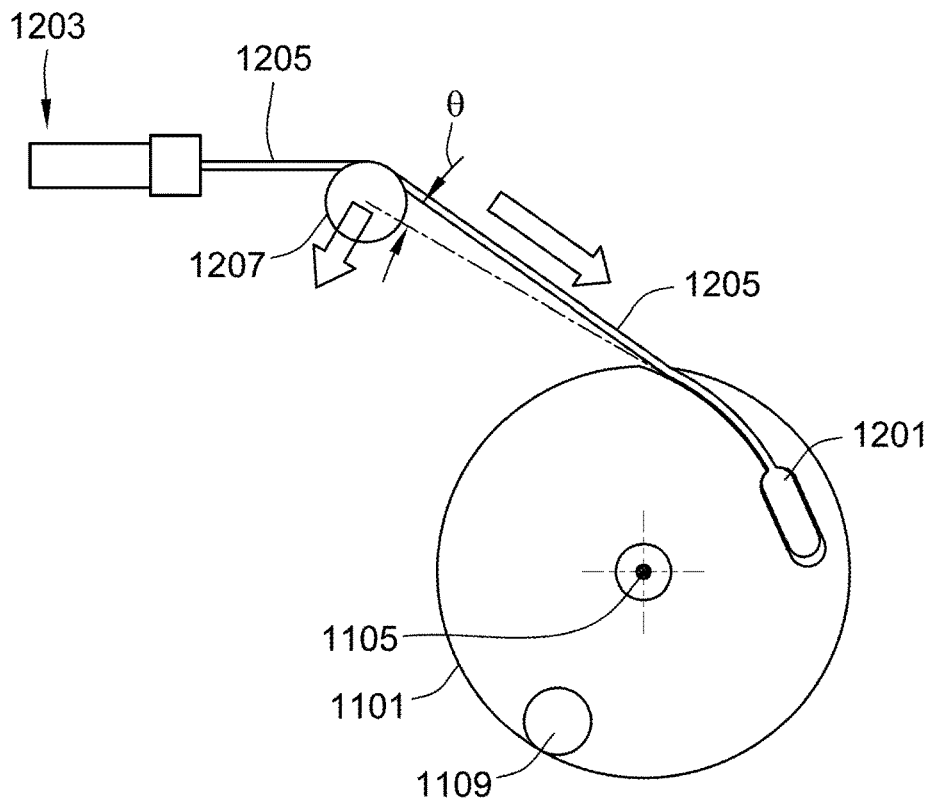

Adverting to FIG. 12A, the pulley 1101 is connected to the end 1201 of a force transmission element 1203. The end 1201 can be a detachable part that is locked into the recess 1115 during use. According to some embodiments, the end 1201 can include a load cell for determining the load applied by the cable 1205 to the pulley 1101. Although illustrated as not being wrapped around the pulley 1101, according to some embodiments, the cable 1205 can be wrapped around the pulley 1101 multiple times to maintain a single exit point of the cable 1205 out of the pulley 1101. When the cable 1205 of the force transmission element is retracted, the pulley 1101 rotates counterclockwise. If the cable 1205 is retracted far enough, the pulley 1101 rotates until the peg 1109 engages the thigh shaft 1103. Continued retraction of the cable 1205 and rotation of the pulley 1101 causes the thigh shaft 1103 to swing forward, which results in a hip flexion moment applied to the user's hip.

According to some embodiments, the peg 1109 can include an integrated sensor (not shown). The integrated sensor can detect the force applied to the shaft 1103. Alternatively, or in addition, the cable 1205 can be routed around an additional pulley 1207 (FIG. 12B) prior to the pulley 1101. One or more sensors (not shown) on the additional pulley 1207 can detect the shear/sideways force on the additional pulley 1207 to measure the tension in the cable 1205 The pulley 1101 can also include an encoder (not shown) that measures the user's hip joint angle. The information acquired from the integrated sensor and the encoder can be used to implement force limits in a controller of a flexible exosuit including the hip drive arrangement 1100, as well as to filter out the impact force of the peg 1109 engaging with the shaft 1103.

In addition to one or more sensory fail safes, the arrangement of the hip drive unit 1100 in combination with the force transmission element 1203 can include one or more mechanical fail safes to prevent injury to the user. By way of example, and without limitation, the connection between the cable 1205 and the recess 1115 can include a breakpoint, the end 1201 of the cable 1205 can include a breakpoint, the post 1105 can include a breakpoint, and the shaft 1103 can include a breakpoint at one or more positions along its length. The described breakpoints are configured to sustain normal loads transmitted to the user through the force transmission element 1203 and the hip drive unit and break to stop transmitting the loads, if the loads exceed a threshold (e.g., harmful) level.

In the arrangement of the hip drive unit 1100, the center of rotation of the thigh shaft 1103 may not be co-located with the center of rotation of the physical hip joint of the toddler, leading to an offset link/compression effect during movement. To compensate for the offset link/compression effect, the thigh shaft 1103 can include a prismatic joint.

FIG. 13A illustrates a thigh shaft 1301 with a center of rotation 1303 located at, for example, a waist of a toddler 1305. The center of rotation 1303 can correspond to a connection point at a proximal end of the thigh shaft 1301 to a hip drive unit (e.g., hip drive unit 1100). The distal end of the shaft 1301 can be located at a termination point 1307 along the user's limb (e.g., along the thigh and/or at the knee).

As illustrated, the center of rotation 1303 can be above the center of rotation 1309 of the toddler's hip, which causes a compressive force about the center of rotation 1309 of the toddler's hip during actuation of the shaft 1301 and/or movement of the leg. That is, the distance $D_1$ between the center of rotation 1303 and the termination point 1307 with the leg straight (FIG. 13A) is greater than the distance $D_2$ between the center of rotation 1303 and the termination point 1307 with the leg bent (FIG. 13B). Yet, the length $L_3$ of the shaft 1301 is fixed. Thus, with the leg bent, a compressive force is generated by the shaft 1301 with the fixed length $L_3$ connecting the center of rotation 1303 and the termination point 1307.

To accommodate this, the prismatic joint 1401 of FIGS. 14A and 14B can be located at the center of rotation 1303. The prismatic joint 1401 allows the shaft 1301 to pass through a pulley 1403 during actuation. Specifically, FIG. 14A illustrates the pulley 1403 with an opening 1405a that allows the shaft 1301 to extend into the pulley 1403. In a non-actuated state, the shaft 1301 extends partially into the pulley 1403. As illustrated in FIG. 14B, in an actuated state, the proximal end of the shaft 1301 slides within the pulley 1403 and out of opening 1405b. By being able to slide within the pulley 1403, the effective length of the shaft 1301 between the center of rotation 1303 (which, in the described embodiment, coincides with the location of the pulley 1403) and the center of rotation 1307 can decrease, which reduces or eliminates the compressive force on the center of rotation 1309 on the toddler's hip because the effective length of the shaft 1301 decreases with the decrease in distance.

Although the end 1301a of the shaft 1301 is illustrated as being within the pulley 1403 in a non-actuated state, the end 1301a may alternatively extend beyond the opening 1405b in the non-actuated state. Additionally, the end 1301a may include a stop (not shown) that prevents the end 1301a from passing into the pulley 1403 or out of the opening 1405a of the pulley.

Figure 15A:
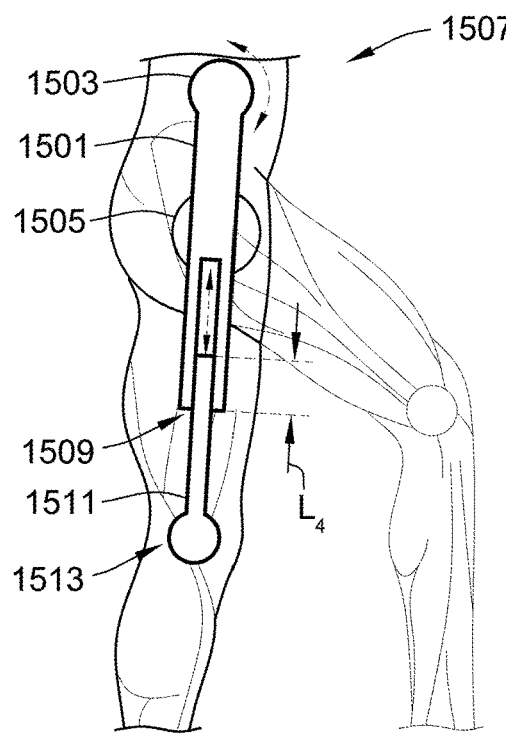
FIGS. 15A and 15B show centers of rotation of the leg in straight (FIG. 15A) and bent (FIG. 135) configurations with respect to an alternative drive shaft in accord with at least some aspects of the present concepts.

FIG. 15A illustrates another embodiment that reduces or eliminates compressive forces generated based on the center of rotation of a shaft being offset from the center of rotation of the hip, in accord with concepts of the present disclosure. The embodiment includes a shaft 1501 connected to a hip drive unit (not shown) about a center of rotation 1503. As before, the center of rotation 1503 may be vertically offset from the center of rotation 1505 of a hip of a toddler 1507. The distal end of the shaft 1501 can include an opening 1509. The opening 1509 accepts a shaft 1511 that extends up from an attachment point about the center of rotation 1513 of the knee of the toddler 1507.

In a non-actuated state, the shaft 1511 extends a length $L_4$ into the shaft 1501 through the opening 1509. In an actuated state, the shaft 1511 extends a length $L_5$ into the shaft 1501, in which $L_3$ is greater than $L_2$. The shaft 1511 extending farther into the shaft 1501 in an actuated state reduces or eliminates the compressive forces about the center of rotation 1505 on the hip of the toddler 1507.

Figure 15B:
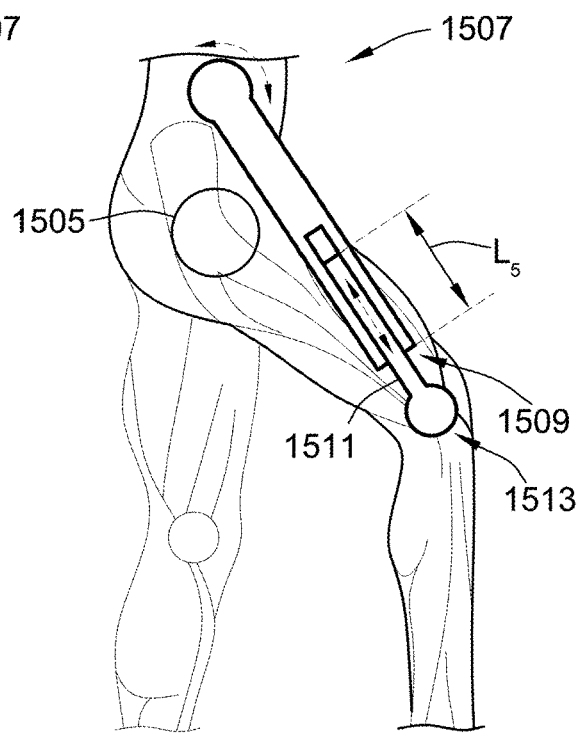
Figure 16A:
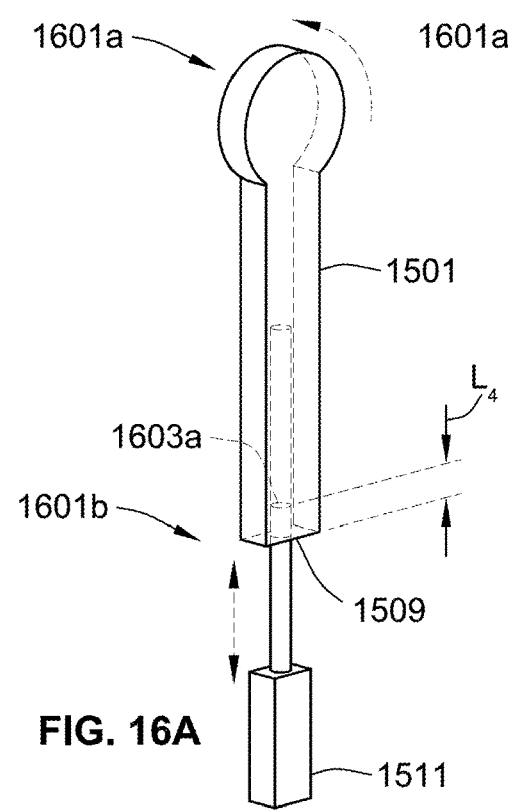
FIGS. 16A and 16B illustrate various configurations of a hip drive shaft of FIGS. 15A and 15B in accord with at least some aspects of the present concepts.
Figure 16B:
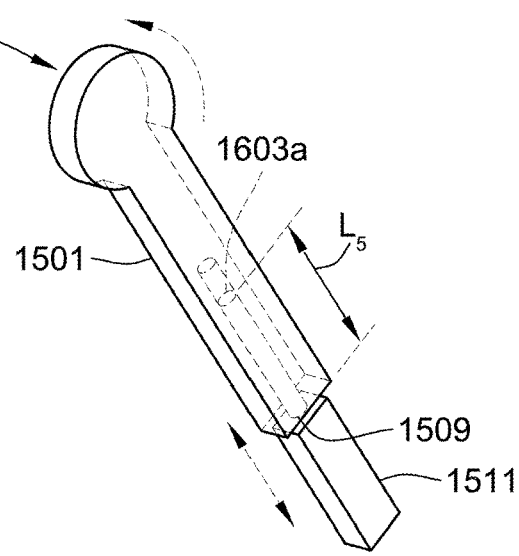

FIGS. 16A and 16B illustrate a detailed view of the shafts 1501 and 1511 of FIGS. 15A and 15B, in accord with aspects of the preset concepts. A proximal end 1601a of the shaft 1501 connects to a hip drive unit, such as the plate 1107 of hip drive unit 1100 about the post 1105. The distal end 1601b of the shaft 1501 includes the opening 1509 that accepts a proximal end 1603a of the shaft 1511. The shaft 1511 is connected to a thigh and/or knee attachment. According to some embodiments, the shaft 1511 is the flexible shaft 909 of FIG. 9. In the non-actuated state, the shaft 1511 extends the length $L_4$ into the shaft 1501 through the opening 1509. In the actuated state, the shaft 1511 extends the length $L_5$ into the shaft 1501, which compensates for the decreased distance between the center of rotation 1505 and the center of rotation 1513 and reduces or eliminates compressive forces about the center of rotation 1505 of the hip of the toddler 1507.

Throughout the flexible exosuit are sensors to determine the positions and actuation statuses of the actuator and flexible exosuit. As previously noted, one or more of the sensors can advantageously be hyper-elastic strain sensors. Such hyper-elastic strain sensors can be integrated with, for example, the PAMs discussed above. In particular, FIGS. 17A-17C illustrate a hyper-elastic strain sensor in accord with aspects of the present concepts.

Adverting to FIG. 17A, a hyper-elastic strain sensor 1700 includes micro-channels 1701 filled with liquid metal supported within an elastomeric base 1703. The micro-channels 1701 are formed in a pattern, such as a boustrophedon pattern. The micro-channels 1701 are above a pneumatic muscle 1705, such as a PAM, that is also supported within the elastomeric base 1703. The pneumatic muscle 1705 is connected to semi-rigid artificial tendons 1707. The hyper-elastic strain sensor 1700 is operatively connected to a micro-controller 1709 that determines strain based on the change in conductivity of the fluid in the micro-channels 1701 as the geometry of the micro-channels change under strain. The micro-channels 1701 can be filled with liquid metal, such as eutectic gallium indium (EGaIn), through micro-valves 1711. The micro-valves 1711 also control the flow of fluid into the pneumatic muscle 1705 during actuation.

FIG. 17B illustrates a non-actuated state of the hyperelastic strain sensor 1700 in accord with aspects of the present concepts. According to a non-actuated state, the pneumatic muscle does not apply strain to the microchannels 1701. During actuation, the pneumatic muscle 1705 contracts under pressure of a fluid flowing into the pneumatic muscle 1705. The contraction of the pneumatic muscle 1705 causes the micro-channels 1701 to contract in the horizontal direction and rise in a vertical direction. The micro-controller 1709 measures the strain on the micro-channels 1701. The strain correlates to the contractile force applied by the pneumatic muscle 1701. One or more of the controller of the flexible exosuit and the top-level controller receive the determined strain and modify control of the flexible exosuit and/or one or more other components of the modular system according to the detected strain.

As discussed above, the flexible exosuit is one of several components of the modular system that acts to develop propulsion, coordination, and stabilization of a toddler. The focus of the flexible exosuit is the application of forces and/or torques at various different joints and/or limbs of the toddler to provide assistance and/or cues for developing walking in a toddler. To mimic the assistive forces provided by an adult caregiver, the modular system may include a support module. That is, as discussed above, the support module is inspired in part by supported walking provided by adults to the exploratory walking of young children. The support module mimics adult assistance by modulating the toddler's center of mass (COM), as required, to facilitate walking, similar to the manner in which adults support exploratory walking of young children.

The support module is configured to apply three-dimensional forces and/or torques to the toddler to perform several functions, including stabilizing medial-lateral and/or anterior-posterior sway, purposely de-stabilizing the toddler to initiate the standing to walking transition, and providing body weight support, if needed. The requirements of the overall medial-lateral and anterior-posterior control will provide a desired three-dimensional force and moment to be applied to the child. The support module can further provide body weight support, if needed. The support module relies on integrated sensing to detect the toddler's COM position, status, balance, and intent, and prevents the toddler from injury by detecting a fall or imminent fall and limiting applied motions/forces.

With respect to the support module being in the form of an arm (such as support module 101a with arm 105), the arm is an actuated arm with a body attachment on the end that grasps the toddler's torso from behind. The arm is designed to be behind the toddler for ease of engaging/disengaging the toddler from the modular system, and also so that the toddler has a clear and unobstructed view of the path forward. The body attachment acts as the interface between the toddler and the support module, securely but comfortably holding the toddler and allowing the application of forces/torques by the support module onto the toddler. The body attachment is designed to be easy to don and doff, like a vest, as well as simple to adjust to fit tightly to the wearer.

FIGS. 18A and 18B show a perspective view (FIG. 18A) and a rear-facing view (FIG. 18B) of an exemplary body attachment in accord with aspects of the present concepts. The body attachment 1801 includes hands 1803 that grasp the toddler from both sides. The hands 1803 can be made of various materials, such as plastic, rubber, etc. The hands 1803 have an ergonomic curved shape to fit under the toddler's arms and around the torso. The hands 1803 can be padded with soft, conformable materials such as foam or molded silicone for further comfort.

FIGS. 19A through 18C show an ergonomic curved shape of the hands 1803 in accord with aspects of the present concepts. The hands 1803 can have a saddle shape and include a ledge 1811 for conforming to under the user's arms. The hands 1803 further include a connection point 1813 for connecting the hands 1803 to the adjustable mechanism 1805. According to some embodiments, the body attachment 1801 can be closed at the open end of the hands 1803, such as by a Velcro® strap, for safety.

The body attachment 1801 further includes an adjustable mechanism 1805 for easily placing the body attachment 1801 on the toddler, closing the body attachment 1801 until it firmly grabs the toddler with the appropriate force, then locking the body attachment 1801. According to some embodiments, the mechanism can be a rack and pinion gear to keep the body attachment 1801 centered. The mechanism 1805 can be manually set and locked by a user (e.g., physician, clinician, technician, parents, guardian, etc.), or the mechanism 1805 can be automated. According to some embodiments, the mechanism 1805 can be manually set according to a manual knob (not shown). Alternatively, or additionally, according to some embodiments, the body attachment 1801 can include an integrated load cell 1807 for detecting grasping force. The hands 1803 close until the load cell 1807 detects a threshold level of grip, which automatically stops and maintains the grasping force. According to some embodiments (not depicted), the adjustment mechanism can consist of more flexible and lower profile structures (as compared to a rack and pinion embodiment), such as laces, ratchets, textile straps, etc., to make the body attachment 1801 as wearable like a garment as possible.

Once the toddler is "wearing" the body attachment 1801 the body attachment 1801 is connected to the rest of the modular system (e.g., the support module and mobile base). The connection is secure during normal operation, but also allows for safe and easy disconnecting if the toddler needs to be quickly removed from the modular system. To this end, the body attachment 1801 has a connector 1815 on the back, with a complementary connector (e.g., connector 2115 of FIG. 21A) located on a flexible joint (e.g., flexible joint 2101 of FIG. 21A) of the support module. According to some embodiments, the connector 1815 consists of a steel plate at the back of the body attachment 1801 that corresponds to a magnetic receptacle of the connecter of the flexible joint. The strength of the magnets is selected such that the connection is strong but still can be manually broken by an adult pulling the toddler out of the system. The shape of the connector 1815 and the corresponding connector of the flexible joint is such that the two parts are fixed relative to each other with repeatable positioning every time the connection is made (e.g., no sliding motion is possible).

With respect to the flexible joint specifically, the flexible joint has flexibility to allow some freedom of motion out of plane by the toddler. In addition, the flexible joint can contain sensing for detecting the status of the toddler's COM, balance, and intent, and preventing the toddler from injury, such as detecting falling or an imminent fall, and limiting the applied motions/forces. According to some aspects of the present concepts, the flexible joint can be the primary component of the modular system that determines the toddler's intent.

FIGS. 21A and 21B illustrate two embodiments of flexible joints, in accord with concepts of the present disclosure. Adverting to FIG. 21A, a flexible joint 2101 includes a plate 2103 configured for quick attach and release from the body attachment 1801 according to conventional techniques. The plate 2103 includes the connector 2115 discussed above. However, according to some embodiments, the plate 2103 and the connector 2115 can be considered a single, integral piece.

The plate 2103 is attached to one or more springs 2105. The springs 2105 provide small rotational flexibility and reduce resistance to torso motion. The flexible joint 2101 further includes a ball joint 2107 that provides the center of rotation mechanically limiting flexibility in rotation only.

The flexible joint 2101 further includes a sensor 2109 between two horizontal plates 2111. The sensor 2109 is configured to detect all directional (6 DOF) loads from the toddler that are transmitted through the flexible joint 2101. The sensor 2109 can be an ATI Mini 40 (US-10-20E) sensor that can detect 40 Newtons (N) of horizontal force and 133 N of vertical force. The sensor 2109 is installed so that its vertical (Z) axis aligns with the weight force of the toddler. At the end of the flexible joint 2101 is a base 2113 for connecting the flexible joint 2101 to a mobile base.

Adverting to FIG. 21B, an alternative flexible joint 2151 includes a plate 2153 configured for quick attach and release from the body attachment 1801 according to conventional techniques. The plate 2153 connects to a base 2155 of the flexible joint 2151 through a Gough-Stewart platform (3R-3T) joint 2157. The 6 DOF joint 2157 can include custom force sensors and springs to provide small rotational flexibility and reduce resistance from torso motion.

The bases 2111 and 2155 of the flexible joints 2101 and 2151 can attach to or constitute actuators that attach the arms to a mobile base and provide movement of the arm relative to the mobile base. According to one embodiment, the bases 2111 and 2155 can be an XY table actuating the arm in the horizontal plane, with a passive mechanism for vertical motion and body weight support. By way of example, the XY table can be a Velmex XY table, model number MAXY4009W1-S4, manufactured by Velmex, Inc., of Bloomfield, N.Y., with a workable envelope of 18.5 inches in both directions and a capacity of 25 pounds of load. According to another embodiment, the bases 2111 and 2155 can be an XYZ table (or equivalent 3 DOF actuator) that actively actuates in the vertical degree of freedom.

Figure 20B:
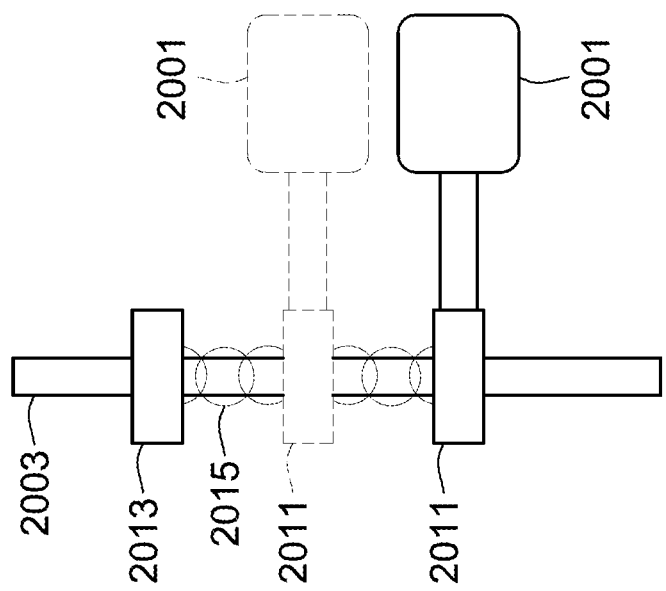
FIGS. 20A and 20B illustrate side views of connections of a support module to a base in accord with at least some aspects of the present concepts.
Figure 20A:
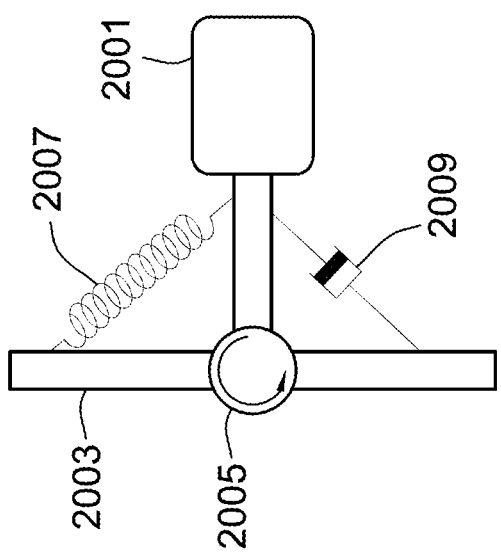

FIGS. 20A and 20B illustrate bases for arms of a support module that actuate in the vertical direction relative to the mobile base, in accord with concepts of the present disclosure. Adverting to FIG. 20A, the base 2001 attaches to a mobile base 2003 at a joint 2005 that allows the base 2001 to move vertically in a radial manner about the joint 2005. An adjustable spring 2007 attached to the mobile base 2003 and the base 2001 provides a vertical restoring force to the base 2001, pre-tensioned to provide the appropriate level of vertical body weight support. A damper 2009 attached to the mobile base 2003 and the base 2001 provides a vertical resistive force to the base 2001. One or more of the joint 2005, the spring 2007, and the damper 2009 can include a sensor to determine the position and load applied by the base 2001 in a vertical direction. Though not shown, the overall assembly can be vertically adjusted with a slide and lever lock to accommodate toddlers of different heights.

Adverting to FIG. 20B, the base 2001 may alternatively connect to the mobile base 2003 at a slide 2011 connected to a lever lock 2013 via a spring 2015 on the mobile base 2003. A user may manually adjust the position of the lever lock 2013 to set the position of the slide 2011. This adjustment accommodates different toddler heights as well as sets the pretension (and corresponding level of vertical force) of the spring. The base 2001 and the slide 2011 represented by the dotted line show the unloaded position of the base 2001 with the toddler not attached to the base 2001. The base 2001 and the slide 2011 represented by the solid line show the loaded position of the base 2001 with the toddler attached to the base 2001. According to the slide 2011, the lever lock 2013, and the spring 2015, the base 2001 can move vertically a threshold distance, such as 60 mm.

The above-described elements of the support module describe a support module that provides active support in the form of medial-lateral and/or anterior-posterior sway assistance and/or cues for developing toddlers through an arm. In addition, or in the alternative, to the above-discussed support structures, the modular system can include an active tether/scaffold-based support module, as discussed above with respect to FIG. 1B. The tether/scaffold-based support module actively adjusts tension in antagonistic tethers that result in stiffness control to allow a greater or lesser degree of COM motion in a particular body plane. The tethers can connect to a body attachment similar to the body attachment 1801 discussed above. The body attachment can be located at the pelvis of the toddler.

Tension in the individual tethers generates a desired force-moment at the pelvis. Each tether will have a cable in series with a spring, with the ability to modulate the tension within the cable. Modulation can be achieved by a DC motor to provide three-dimensional support to the pelvis both in position and orientation. The configuration of the tether/scaffold-based support module provides full or partial gravity balancing of the trunk as a toddler ambulates on the ground. The active modulation of tension in tethers further provides medial-lateral and/or anterior-posterior support to the toddler during motion. Although discussed above with respect to an active tether/scaffold-based support module being attached to the mobile base, according to some embodiments, the active tether/scaffold-based support module can be independent from (separate from) the mobile base. By way of example, the active tether/scaffold-based support module can be a separate, movable structure, such as a self-supported structure on the ground, suspended from the ceiling, suspended from a gantry crane, etc.

According to some aspects of the present concepts, the support module can be passive, rather than active. Such a support module can passively support the user (e.g., the COM and/or one or more limbs of the user) while the user explores the stability and instability of stance and motion. By way of example, a passive support module can passively support the user while one or more other modules (e.g., flexible exosuit, mobile base) dynamically perform one or more functions on the user to modulate the user's stance and/or movement.

According to one embodiment, a passive support module can include a passive arm. The passive arm can passively function according to one or more of the functions described herein with respect to the arm of an active support module. By way of example, a passive arm can support the full or partial weight of the user, while the flexible exosuit and the mobile base dynamically modify the user's stance and/or motion.

The structure of the passive arm can correspond substantially to the active arm disclosed herein, but may exclude the one or more controllers, one or more actuators, and/or one or more sensors of the active arm. According to some embodiments, an active arm, as disclosed herein, can be dynamically changed to an active mode and a passive mode. Whether the arm is set to an active mode or a passive mode configures the arm to actively interoperate with the other modules within the modular system (e.g., active mode), or passively interoperate (or not interoperate) with the other modules, such as being fixed according to one function.

According to some embodiments, a passive support module can include a suspension harness to catch the toddler in case of a fall. A suspension harness can be used alone or in combination with the above-described elements of the support modules. By way of example, although an arm of a support module is capable of safely supporting the full weight of the toddler, the support module can also include a suspension harness to support the entire weight or partial weight of the toddler. The suspension harness can be mounted so that it is slightly slack and does not bear any load during normal operation, and only bears load if the toddler falls, collapses, or tries to sit down.

According to some embodiments, one or more passive support modules include, by way of example, a gantry crane, a rail-based support, and a cart. Such passive support modules can be a designed to include a passive spring system to provide some support. The flexible exosuit, the mobile base, and/or an active support module can be used in combination with such a passive support module. Alternatively, or in addition, a passive support module can include upper-limb based support such as crutches/walking sticks.

As discussed above, the support structure, auxiliary components of the flexible exosuit (e.g., pump, compressor, and/or motors), and other control and power hardware are mounted on the mobile base. Placing these components on the mobile base prevents the toddler's natural motion from being hindered by the added inertia of these components. The mobile base and its components move along with the toddler as the toddler walks forward. As discussed above, the mobile base also has the potential to act as a support surface that the toddler can grasp and use as a source of tactile feedback that helps the toddler maintain a stable posture.

By way of example, in an assistive embodiment, the mobile base can have a top speed of 4 miles per hour (mph) powered by a 24 volt (V), 270 Watt (W), 4700 rotations per minute (rpm) motor. With respect to powering hip actuation, power can be provided by an EC60 flat 100 Watt motor from Maxon, operating at 48V, which has a maximum torque of 5.01 Newton meters. Normal applied torque can be 2.3 Nm, which is ⅓ of the biological hip flexion moment in a normal (e.g., 2-year-old) toddler. However, specific such values can vary depending on the user and the amount of assistance needed. In at least some aspects of the present concepts, the system is powered off a set of at least four 12V batteries, wired in series to provide the various voltages needed to power a variety of different actuators (e.g., mobile base motor runs on 24V, exosuit motors are 48V). The capacity of the batteries can also be selected to provide desired run times (e.g., 30 minutes of continuous use, 1 hour of continuous use, etc.). According to some embodiments, the controllers and sensors are on a separate power circuit to electrically isolate the user from high currents of the motor circuit, to reduce the risk of electric shock. However, the above-described specifications are exemplary and will vary depending on the size and type of the user and the type of therapy or assistance being provided to the user.

Each module of the modular system can function independently so that the support provided by the overall modular system can be scaled back. According to one embodiment, each module of the modular system can have its own controller. At the same time, the modules are capable of interoperability and integrate/coordinate with each other. To this end, the modular system includes a hierarchical control approach that includes a top-level controller that determines in real-time the dynamic reconfigurations required for the mobile base, support module, and flexible exosuit in order to perform the desired assistive functions. This top-level controller sends the appropriate commands to each module. The hierarchical system works together to behave cooperatively with the toddler, rather than forcibly overriding the toddler's natural motion. To this end, all modules of the modular system have integrated sensing for gathering information about the toddler's motion.

When all of the modules are in use, the modules function to achieve three specific goals to help toddlers with the transition from assisted to unassisted walking: coordination, propulsion, and stabilization.

With respect to coordination, a toddler or other user explores joint angle rotations and discovers how to coordinate rotations to preserve whole limb kinematics. For example, a toddler discovers how to allow a leg to behave like a mass-spring pendulum system. With respect to the goal of coordination, the support module provides partial loading and unloading with respect to gravity balancing. In combination with the flexible exosuit, the loading and unloading can be timed to coincide with actuations of the flexible exosuit, such as actuations at the hip and ankle joints. The flexible exosuit can provide hip and ankle actuations that maintain whole limb behavior.

With respect to propulsion, a toddler or other user can explore the forward propulsive behavior of the body's COM during swing phase, stance phase, and the footfall/load acceptance/COM redirection that occurs in the transition between the two phases. During this exploration, the support module can provide fine movement in conjunction with coarse movement of the mobile base and/or the toddler. The fine movement can maintain invariant position with respect to the child's assisted forward motion. The support module can further provide partial loading and unloading with respect to gravity balancing. In combination with the flexible exosuit, the loading and unloading can be timed to coincide with actuations of the flexible exosuit, such as actuations at the hip and ankle joints. The flexible exosuit can provide hip and ankle actuation that maintains whole limb behavior and remains within the stability region of the body's COM.

With respect to stabilization, the toddler can explore the medial-lateral motion and/or the forward component of anterior-posterior behavior of the body's COM during single and double support phases. During this exploration, the support module can modulate the equilibrium and tension/stiffness of the medial-lateral motion. The flexible exosuit can provide actuation, such as at the hip and ankle, and/or modulate the stiffness of the joints. The support module can further provide partial loading and unloading with respect to gravity balancing. In combination with the flexible exosuit, the loading and unloading can be timed to coincide with actuations of the flexible exosuit, such as actuations at the hip and ankle joints.

Adverting to FIGS. 22A and 22B, these figures illustrate the combinative motions of a support module 2205, with an arm, and a mobile base 2207 of a modular system 2200 relative to the motion of a toddler 2203, in accord with concepts of the present disclosure. The arrows 2201*a* through 2201*c* represent the movements of the toddler 2203, the support module 2205, and the mobile base 2207, respectively. The graphs 2211*a* through 2211*c* of FIG. 22B show the velocities as a function of time of the toddler 2203, the support module 2205 (relative to the mobile base 2207), and the mobile base 2207, respectively.

As the toddler 2203 begins to move according to arrow 2201a, the support module 2205 can move forward according to arrow 2201b to match the velocity of the toddler 2203. The graphs 2211a and 2211b match during the period 2213a. According to some embodiments, for safety, the mobile base accelerates slowly and then follows at a constant speed. More rapid movements can be performed by the support module.

As the modular system determines from one or more sensors that the toddler 2203 continues to move in the direction 2201a, the coarse movement control of the mobile base 2207 begins in the direction of arrow 2201c and complements the fine movement control of the support module 2205. During periods 2213b and 2213c, the combination of the graphs 2211b and 2211c matches the movement of the toddler 2203 within the graph 2211a. For a smooth transition between control of movement by the mobile base 2207 and the support module 2205, both can operate to match the movement of the toddler 2203 prior to the total control of the movement being handled by the mobile base 2207, as illustrated by the graphs 2211b and 2211c in FIG. 22B.

The same configuration may occur as above, in reverse, to stop the modular system 2200 when the toddler 2203 comes to rest. As toddler 2203 begins to slow down, fine movement control by the support module 2205 can decelerate the modular system 2200, as illustrated by period 2213e in graphs 2211a through 2211c. As the modular system determines that the toddler 2203 is further slowing down, the mobile base 2207 may begin to decelerate and complements the movement control of the support module 2205, as illustrated in period 2213f in graphs 2211a through 2211c. Once the toddler 2203 stops moving, the support module 2205 and the mobile base 2207 may continue to move to reset to a default configuration and position relative to the toddler 2203, as illustrated in period 2213g in graphs 2211a through 2211c.

FIGS. 23 and 24 show overall kinematic elementals for a modular system that includes a support module with an arm, a mobile base configured to actively follow a toddler, and a flexible exosuit (FIG. 24), in accord with aspects of the present concepts.

Adverting to FIG. 23, the kinematic elemental 2301a represents the active horizontal (e.g., forward-backward) movement 2303a of a mobile base configured to actively and dynamically follow a toddler's movement. Such movement can be powered by a motor and drive arrangement within the base, and controlled by the mobile base controller according to information from one or more proximity sensors and/or motion sensors. By way of example, the movement 2303a can have a continuous range of motion of 0.5 meters per second (m/s).

Kinematic element 2301b represents the manual vertical movement 2303b to adjust the vertical position of a support module. According to other embodiments, the vertical movement 2303b can be automated, such as being based on a vertical load sensor within the support module.

Kinematic element 2301c represents the passive vertical movement 2303c of, for example, the connection of the arm of the support module to the mobile base, with passive vertical movement capability. Such passive vertical movement 2303c may be according to a vertical range of motion allowed in the support module for vertical variations in a toddler's posture.

Kinematic element 2301d represents the active medial-lateral movement 2303d of the arm of the support module, and kinematic element 2301e represents the active anterior-posterior movement 2303e of the arm of the support module. The active medial-lateral movement 2303d and the active anterior-posterior movement 2303e provide sway support and triggers imbalances to, for example, initiate forward motion of the toddler. By way of example and without limitation, the ranges of both movements 2303d and 2303e can be 100 millimeters (mm) at a speed of 0.5 m/s.

Kinematic element 2301f represents the passive range of motion allowed between the body attachment and the flexible joint of the arm of the support module, which allows for a limited range of motion in two or more planes.

Kinematic element 2301g represents the manual range of motion 2303g of the body attachment attached to the arm. The range of motion 2303g can provide a toddler with a limited degree of freedom at the end of the support module.

Adverting to FIG. 24, kinematic elements 2301h and 2301i represent the hip drive units on a flexible exosuit that provide active circular ranges of motion 2303h and 2303i, respectively, about the user's hips (e.g., toddler's hips). The foregoing kinematic elements and corresponding motions provide the modular system with a full range of motion that allows a user to explore how to use the body during locomotion.

Figure 25:
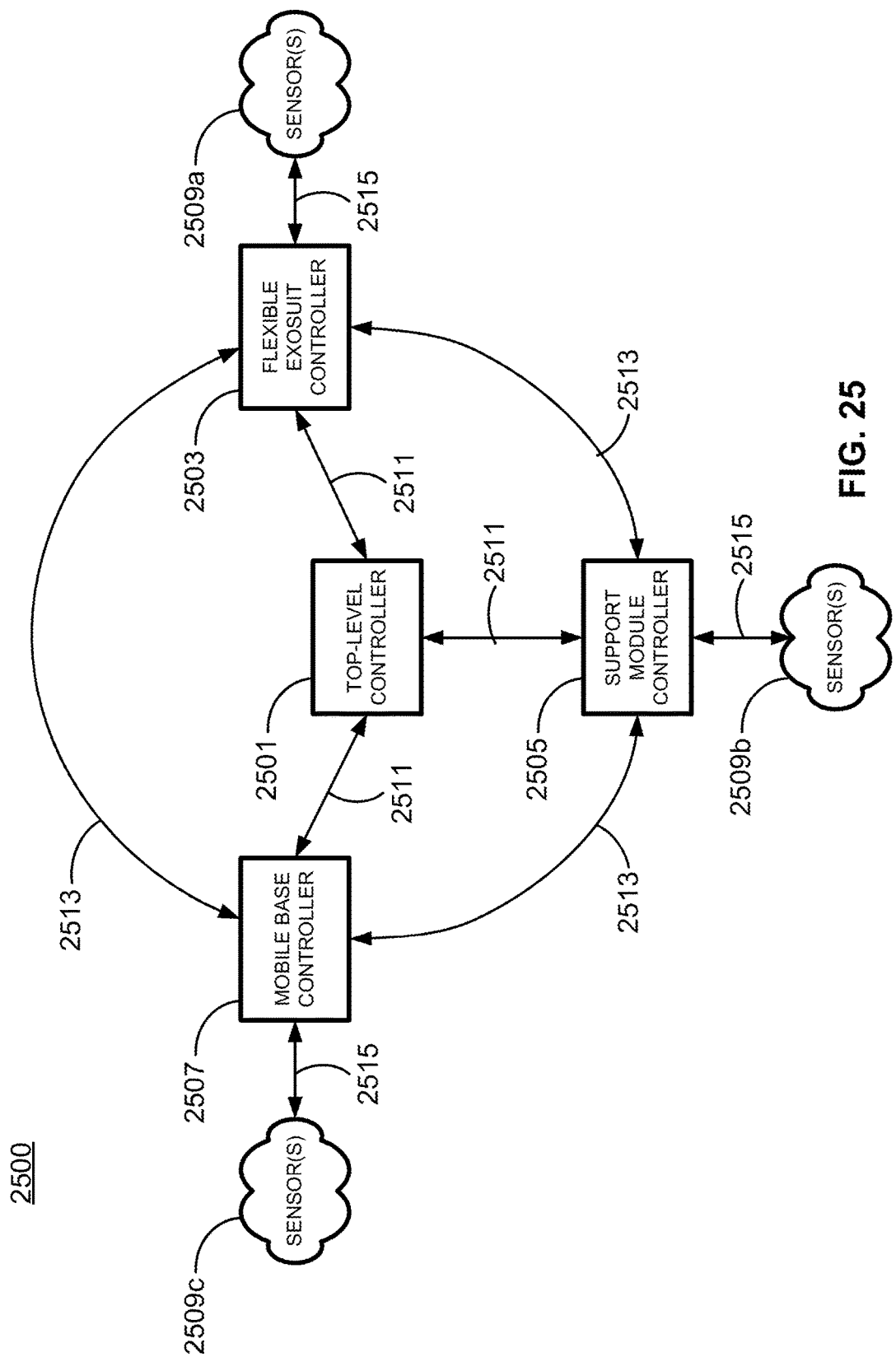
FIG. 25 shows a control arrangement in accord with at least some aspects of the present concepts.

FIG. 25 shows a control arrangement 2500 within the modular system in accord with aspects of the present concepts. The control arrangement 2500 includes the top-level controller 2501. As discussed above, the top-level controller 2501 can be included within the mobile base to off load weight from the toddler. The control arrangement 2500 further includes a flexible exosuit controller 2503, a support module controller 2505, and a mobile base controller 2507. The flexible exosuit controller 2503 and the support module controller 2505 can be located in each separate module, or can also be located within the mobile base. The flexible exosuit controller 2503, the support module controller 2505, and the mobile base controller 2507 are in communication with various sensors, represented by groups of sensors 2509a, 2509b, and 2509c, respectively. The groups of sensors 2509a-2509c are represented as separate and distinct groups for ease of illustration; however, one or more sensors can be considered as being within more than one group. For example, a single sensor (e.g., proximity sensor) may communicate with the flexible exosuit controller 2503, the support module controller 2505, and the mobile base controller 2507 such that the single sensor can be considered within any one or all of the groups of sensors 2509a-2509c. Further, although FIG. 25 illustrates a modular system associated with all three modules (e.g., flexible exosuit, support module, and mobile base), one or more of the modules can be removed based on the needs and/or progression of the toddler without departing from the spirit and scope of the control arrangement 2500 illustrated in FIG. 25.

The top-level controller 2501 communicates with the flexible exosuit controller 2503, the support module controller 2505, and the mobile base controller 2507 based on wired or wireless two-way or one-way communication paths, represented generally by arrows 2511. According to some embodiments, the flexible exosuit controller 2503, the support module controller 2505, and the mobile base controller 2507 communicate directly with each other based on wired or wireless two-way or one-way communication paths, represented generally by arrows 2513. Further, the top-level controller 2501, the flexible exosuit controller 2503, the support module controller 2505, and the mobile base controller 2507 communicate with the sensors of the sensor groups 2509a-2509c based on wired or wireless two-way or one-way communication paths, represented generally by arrows 2515. Although illustrated as separate and distinct communication paths, one of more of the communications paths 2511-2515 can be integrated into a single communication path.

The top-level controller 2501, the flexible exosuit controller 2503, the support module controller 2505, and the mobile base controller 2507 can be hardware-based controllers and/or software-based controllers. For software-based controllers, the controllers can be one or more processors that execute specific computer-readable instructions stored on one or more transitory and/or non-transitory computer-readable storage mediums that, when executed, cause the controllers to perform one or more functions and/or cause the controllers to cause one or more elements within the modular system to perform one or more functions. The mobile base can include one or more computer-readable storage mediums that store the computer-readable instructions, such as optical discs, random access memory (RAM), read only memory (ROM), flash drives, solid state drives, magnetic storage drives, etc.

According to a software-based controller approach, and by way of example, and without limitation, a system software architecture can be divided into two main layers: System Services Layer (SSL), and Application Layer (AL). The SSL implements fundamental components that manage local resources and provides primitives to support algorithms at the AL. The SSL implements a clock-driven scheduler, handles inter-module communication, accesses sensor information, and sets configuration and actuation parameters. The AL can specify application goals using the services provided by the SSL. The clock-driven scheduling provides predictable execution of specific tasks at individual modules, allowing simplification of control of timing of sensing, processing, and actuation tasks.

According to a hardware-based controller approach, by way of example, and without limitation, hardware-based controllers can be implemented based on a PC-104 stack, which can consist of, for example, one or more processors (e.g., an Aurora Single Board Computer with 1.6 GHz processor), one or more power supplies (e.g., a Jupiter-MM-LP DC/DC power supply), and one or more input/output modules (e.g., a Diamond-MM-32DX-AT Analog I/O module). The input/output modules can have analog and/or digital inputs and outputs (e.g., 32 single-ended analog inputs, 4 analog outputs, and 24 digital inputs/outputs), and can also include automatic calibration for temperature changes.

Modeling within the control arrangement 2500 to execute the functionality of the control arrangement 2500 can be accomplished according to various methods without departing from the spirit and scope of the present concepts. According to some embodiments, and without limitation, functionality within the control arrangement 2500 can be based on Simulink® models, and the models can be run based on dedicated hardware controllers. By way of example, one or more of the controllers of the control arrangement 2500 are designed as a Simulink® model containing both standard modeling blocks as well as xPC target-specific blocks that allow input/output with supported hardware.

One or more models executed within the control arrangement 2500 can be configured external to the control arrangement 2500 (e.g., on a host computer) and subsequently transferred to one or more of the controllers within the control arrangement 2500, such as by a wired or wireless connection (e.g., Wi-Fi, Bluetooth, Ethernet, serial connection, etc.). The controller(s) within the control arrangement 2500 can then operate independent of, for example, the host computer. Alternately, according to some embodiments, the connection between, for example, the host computer and the one or more controllers can be maintained for real-time parameter tuning while the model(s) are being executed within the control arrangement 2500. Maintaining a real-time connection also allows real-time interfacing with a graphical user interface (GUI), such as MATLAB, which can serve as the basis for allowing user input during operation.

Within the arrangement 2500 of FIG. 25, the learning assistance provided by each module may progress at different rates, which allows for a more dynamic learning process for the user by adjusting each module to meet the individual's specific needs. The task of learning to walk is simplified for the user according to the modularity permitting one module to provide maximum support for one task (e.g., by providing maximum medial-lateral stability) while relaxing support for another task, which allows the user to focus on the other task (e.g., learning to use stepping for forward propulsion). The division of computation and functionality between the various modules further simplifies the computational challenges of controlling the assisted learning.

According to the control arrangement 2500 of FIG. 25, the top-level controller 2501, the flexible exosuit controller 2503, the support module controller 2505, and the mobile base controller 2507 interoperate together to provide opportunities for a user to explore the body's stability and instability in different conditions and to explore how to use the body in consideration of the stability/instability for locomotion.

The top-level controller 2501, the flexible exosuit controller 2503, the support module controller 2505, and the mobile base controller 2507 together form and are controlled as a cyber-physical system of collaborating computational elements controlling physical entities. Specific techniques for modeling and controlling cyber-physical systems can be found in the following publications: "High-Confidence Medical Devices: Cyber-Physical Systems for 21st Century Health Care," High Confidence Software and Systems Coordinating Group of the Networking and Information Technology Research and Development Program, February 2009; "Body Sensor Networks: A Holistic Approach From Silicon to Users," Calhoun, B. H. et al., Proceedings of the IEEE, Vol. 100, No. 1, January 2012; "Toward a Science of Cyber—Physical System Integration," Sztipanovits, J. et al., Proceedings of the IEEE, Vol. 100, No. 1, January 2012; and "Special Issue on Cyber-Physical Systems," Poovendran, R. et al., Proceedings of the IEEE, Vol. 100, No. 1, January 2012, the entirety of each of which is herein incorporated by reference.

The control arrangement 2500 of FIG. 25 operates to control opportunities for the user (e.g., toddler) to explore the body's stability and instability in different conditions. These conditions can be, for example, and without limitation, during a standing mode and during a walking mode.

During a standing mode, the control arrangement 2500 controls the modules to provide a safe environment for the user to explore stability and instability while standing. As opposed to a rigid structure that restricts movements according to forced corrective motions, during a standing mode, the modular system allows a user to learn by doing, such as by exploring and/or experimenting with motion (e.g., walking) However, the modular system provides a limited and directed environment so that the user can focus on experiencing and learning the subtasks of standing as a precursor to walking.

By way of example, and without limitation, the control arrangement 2500 operates according to the following acts during the standing mode. Initially, the user is integrated into the modular system in a "zero" position. The user's weight is initially fully supported by the support module (e.g., such as the arm or tether/scaffold). The user can be wearing the flexible exosuit in an entirely passive state.

Upon integrating the user within the modular system, the control arrangement 2500 of the modular system operates to perform one or more acts with respect to allowing the user to explore standing in the vertical and horizontal planes. With respect to the vertical plane, according to one act, the user's weight is slowly loaded onto the user. That is, support of the user's weight by the support module is reduced by vertically lowering the support module so that the user supports more weight through his or her legs, rather than through the support module. Concurrently, one or more additional acts can occur.

By way of example, according to one additional act, sensor readings from the flexible exosuit may indicate that the user is not accepting the additional load. Instead, the user may be collapsing under the increased load. Such indications can be based on, for example, joint angle measurements from the flexible exosuit in comparison to weight load measurements from the support module. In response, one or more antagonistic forces to the collapsing joint are applied through the flexible exosuit to stiffen the flexible exosuit and help the user support his or her weight with their legs. The forces can be variable and dynamic. For example, as the user moves upwards, as detected by, for example, support module force sensors and/or joint angles measurement by IMUs in the flexible exosuit, the flexible exosuit will dynamically relax. As the user moves back downwards (detected by the same sensors or different sensors), the flexible exosuit can again stiffen to aid with the weight acceptance. The adjustments by the support module and the flexible exosuit can be finely tuned to allow the user to determine the maximum level of relaxation before collapse, while maintaining the user within a safe and secure environment.

By way of an additional example, according to another additional act, while loading the weight of the user onto the user's legs, the support module can lock the user's horizontal position while keeping the vertical position unlocked. Under these conditions, the user can move his or her body up and down against gravity, while stiffening, relaxing, or pushing with certain muscles, and experiencing how different muscles and coordinated movements correspond to vertical oscillation/bouncing.

With respect to the horizontal plane, upon integrating the user within the modular system, the control arrangement 2500 of the modular system can operate to perform another act. According to the other act, the support module can operate to allow motion in one of the anterior-posterior plane or medial-lateral plane, while leaving the other of the anterior-posterior plane or medial-lateral plane locked. According to this operation, the support module provides little to no resistance against the user's motion within the unlocked plane when the user is upright or near upright. However, if the user leans past a threshold of the COM stability or balance (e.g., forwards/backwards or side-to-side, depending on the plane), the support module provides more resistance to prevent uncontrolled falling towards the boundaries of the user's balance. Whether the user leans past the threshold of the COM stability or balance can be detected by, for example, position feedback of the actuator within the support module, such as the arm's actuator.

Rather than swaying within the stable boundaries of stability in the anterior-posterior plane, the user may become stuck at the boundary or beyond and be unable to restore himself or herself to an upright position. The support module can actively push or pull the user back to an upright position. Alternatively, or in addition, the flexible exosuit can apply one or more restorative forces to help the user reach an upright position. Alternatively, or in addition, the mobile base may actively move (e.g., forward/backward or left/right, depending on the plane) with the user's legs pivoting on the ground to restore the user to an upright position.

Control of the modular system to allow anterior-posterior or medial-lateral movement can occur until the user can stably oscillate/sway in the particular plane without falling towards boundaries, and until the user can restore himself or herself to an upright position. Upon the user being stable within one plane, the modular system can be controlled to focus on the other plane. Further, upon being stable in both planes, the modular system can be controlled to unlock both planes with respect to the support module and allow the user to move in a 3D upside down cone of stability.

Upon completion of one of the above-described acts, the control arrangement 2500 can control the modular system to perform one or more remaining acts. At the end of performing the above-described acts, the user has learned bodily control with respect to standing.

With respect to a walking mode, the control arrangement 2500 controls the modules to provide a safe environment for the user to explore stability and instability while walking. The walking mode consists of, for example, destabilizing the toddler to go from standing to stepping, and eventually achieving sustained forward walking.

According to one act, the control arrangement 2500 controls the modular system to induce an imbalance in the user to induce walking. The imbalance can be applied to the user through the support module. The imbalance moves the user sideways slightly to trigger a shift in weight to one leg (the stance leg in gait). Subsequently, the un-weighted leg (the swing leg) moves forward and accepts the weight of the user. According to some embodiments, for the first step, the forward motion is small so the mobile base does not move. Rather, the forward motion can be achieved by the support module and the flexible exosuit coordinating with each other.

Stepping involves all joints. However, with respect to toddlers, in particular, the hip, knee, and ankle are the most prominent. Toddlers generally do not have developed/strong hip extension, hip flexion, or ankle plantar flexion, which are the primary sources of propulsion in adults. According to some aspects of the present concepts, during and/or subsequent to triggering imbalance, the flexible exosuit can apply forces and/or cues with respect to hip flexion.

Based on the above, the control arrangement 2500 of the modular system operates to perform one or more acts with respect to allowing the user to explore the locomotion of walking According to one act, through a combination of the position information of the support module, such as the amount the user is leaning on the arm (as indicated by a force sensor), as well as the position of the leg (from joint angle measurements in the flexible exosuit), the modular system can detect when the user leans sideways and shifts his or her weight to one leg. Subsequently, the support module can provide a forward propulsive force to push the user forward, which induces the forward fall over the weight-bearing stance leg (like an inverted pendulum). Simultaneously, the flexible exosuit can support the stance leg and actuate a hip flexion moment in the swing leg. The flexible exosuit can subsequently stop actuating hip flexion, and become transparent to the wearer, allowing the swing leg to come back down and hit the ground. According to some embodiments, the flexible exosuit can also stiffen the swing leg to help with load acceptance immediately prior to this contact. The above actions can be repeated for alternating the left and right legs as the swing leg and the stance leg until the user is flexing his or her hip independently with the correct timing. This information can be detected according to a progression of measurements of one or more of the sensors within the flexible exosuit and/or the modular system as a whole.

Once going from standing to stepping progresses, control of the modular system can shift to the operation of continuous walking Continuous walking involves the rapid transition from one stance leg to the other over successive steps (e.g., left leg is stance leg, fall forward over left leg like an inverted pendulum, right leg flexes, steps forward, then becomes new stance leg, repeat inverted pendulum motion) and redirecting the COM velocity accordingly.

Toddlers have a relatively fast gait frequency so motion during continuous walking can be rapid. Accordingly, in some aspects of the present concepts, the support module follows the trajectory of the hip, torso, pelvis, or COM according to that of a typical/normal user (e.g., normally developing toddler), but the trajectory is scaled temporally to match the user's step frequency. The step frequency can be measured in real-time by, for example, gait sensors in the flexible exosuit. The step frequency can also be scaled spatially to match anthropometric parameters of the user. Such anthropometric parameters can be, for example, measured before integrating the user in the modular system, and can be entered into the modular system as controller parameters.

According to some embodiments, the support module can behave such that the motion of following the trajectory is freely permitted, while motion in other directions is met with some resistance. According to some aspects, the amount of resistance is scaled up the further the user goes from the "desired" motion. In one embodiment, if the user is providing a lot of resistance, the system will stop operation for safety.

The control arrangement 2500 can continue the above acts with respect to the walking mode as the user explores the motions of the body with respect to walking. As the user develops the correct motions, and at the end of performing the above-described acts, the user has learned to control his or her body with respect to walking.

The control discussed above with respect to the acts occurs according to, for example, two timescales. A first timescale occurs in real-time and pertains to inputs and outputs that dynamically control the modules of the modular system, such as the measurements force sensors of the support module and the IMUs in the flexible exosuit. A second timescale logs information that can be used by the modular system and/or a user (e.g., physician, clinician, technician) to modify to the control of the modular system over time as bodily control of the user progresses.

By way of example, information logged with respect to the second timescale allows the system to modify control as the user develops the various subtasks of walking, which include subtasks related to being able to stand. According to the logged information with respect to the second timescale, the modular system modifies control to continue development and the ability for the user to explore different aspects of locomotion, such as the modular system switching from unlocking movement in the medial-lateral plane to unlocking movement in the anterior-posterior plane.

Although the above-described acts include all three modules, one or more of the modules can be omitted either from the beginning, or during the progression, depending on the needs and/or capabilities of the user.

By way of example, in the case where a toddler has normal limb strength and muscle coordination, but needs assistance with balance, the flexible exosuit can be removed while the support module and mobile base can remain. In this example, sensors for limb motion and joint angles can be kept on the user's limbs (despite the user not wearing a flexible exosuit) to continue informing one or more controllers (e.g., top-level controller 2501, mobile base controller 2507, support module controller 2505) of the overall state of the system. Alternatively, or in addition, information acquired from one or more remaining sensors can be used to determine limb motion and joint angles in the absence of sensors on the flexible exosuit. Alternatively, the user may continue wearing the flexible exosuit, but the flexible exosuit can be disengaged from any power source, such as removing force transmission elements, disconnecting the force transmission elements from the power sources, etc. The above-described function with respect to the control aspects of the modular system can be the same, except for excluding the flexible exosuit operations.

By way of another example, in the case where the user has a well-developed sense of balance but is lacking the muscle strength to walk, the support module can be removed while the flexible exosuit and the mobile base remain. Such an example may be when a toddler suffers from abnormal joint alignments and motions because of conditions such as cerebral palsy. In this example, the flexible exosuit can be configured to provide corrective motion. In the absence of the support module, the mobile base can include proximity sensors to detect and maintain a safe distance of the mobile base from the user. According to an actively powered embodiment of the mobile base, the mobile base can follow the user from behind. Further, without the support module, according to some embodiments, a smaller or different mobile base can be used based on the smaller dimensional requirements of the flexible exosuit components on the mobile base as compared to the support module.

According to some concepts of the present disclosure, and without limitation or exclusion of various other control methods, the control arrangement 2500 can be modeled and controlled as a finite-state machine. By way of example, and without limitation or exclusion of various other control methods, the flexible exosuit controller 2503, the support module controller 2505, and the mobile base controller 2507 control the modular system as a six-state machine. Exemplary states of the six-state machine are safety, comfort, initialization, ready/stop, directed exploration, and repetition. At all times during operation, the state(s) of safety and/or comfort can be active. The safety state functions to provide physical safety of the toddler interfacing with the modular system, and the comfort state functions to minimize unnatural forces and/or sensations during operation.

During the safety state, the top-level controller 2501, the flexible exosuit controller 2503, the support module controller 2505, and/or the mobile base controller 2507 function to prevent falling and/or dragging of the toddler by the modular system, limit speed and/or acceleration of the modular system, maintain a threshold grasping force, and/or limit cable displacement. One or more sensors within the control arrangement 2500 provide information during the safety state can include a pressure sensor on the body attachment for indicating vertical security of the body attachment, a force sensor to detect leaning, encoders, an accelerometer, a DOF pressure sensor, and a cable range bracket.

During the comfort state, the top-level controller 2501, the flexible exosuit controller 2503, the support module controller 2505, and the mobile base controller 2507 control the modular system to provide passive vertical motion, allow rotational flexibility, provide soft contact, monitor gripping force, and minimize suit joint resistance.

The initialization state is for positing the toddler within the modular system. The role of the initialization state is to engage the toddler and zero or initialize the modular system. During the initialization state, the top-level controller 2501, the flexible exosuit controller 2503, the support module controller 2505, and/or the mobile base controller 2507 control the modular system to check that the toddler is positioned correctly, initiate a flexible exosuit position default or configuration, hold the toddler's torso, provide the correct holding force, minimize vertical load on the toddler, and initiate actuator positions.

The ready/stop state is for readying the modular system to move initially and between times of exploration (e.g., when the exploration state is disengaged). The role of the ready/stop state is to provide support and stability during no motion, and release during times of motion. During the ready/stop state, the top-level controller 2501, the flexible exosuit controller 2503, the support module controller 2505, and/or the mobile base controller 2507 control the modular system to stabilize the toddler (e.g., adjust the arm of the support module to minimize leaning force), sense forces/torques applied by the toddler, and provide a "stop" state that locks the modular system (e.g., support module, flexible exosuit) until it is stable release the toddler.

The directed exploration state directs the toddler according to specific motions by purposefully de-stabilizing the toddler in a specific direction (e.g., forward), and then stabilizing the toddler with respect to that direction. The role of directed exploration is to provide controlled recoverable instability and direction correction. During the directed exploration state, the top-level controller 2501, the flexible exosuit controller 2503, the support module controller 2505, and/or the mobile base controller 2507 control the modular system to sense the toddler's leaning force, guide the leaning forward, determine a threshold leaning force to initiate hip joint actuation on the flexible exosuit, and relocate the toddler's arms by the flexible exosuit to return to a threshold leaning force.

The repetition state trains the toddler in walking forward. Accordingly, the role of the repetition state is to provide repeated steps forward. During the repetition state, the top-level controller 2501, the flexible exosuit controller 2503, the support module controller 2505, and/or the mobile base controller 2507 control the modular system to simultaneously recover arm relocation, monitor the toddler's inertia with a leaning force, and synchronize hip joint manipulation.

According to some embodiments, during the above-described states, the control arrangement 2500 works to integrate control over the available modules according to the top-level controller 2501, while distributing control functions and tasks to specific modules. According to additional embodiments, the top-level controller 2501 can be considered a distributed controller that is embodied in one or more other controllers within the control arrangement 2500, such that any one of the flexible exosuit controller 2503, the support module controller 2505, and/or the mobile base controller 2507 can function according to the top-level controller 2501. The modular system takes a hierarchical approach, with the top-level controller 2501 determining in real-time the dynamic configurations for the mobile base, the support module, and the flexible exosuit to perform the desired assistive function. According to control provided by the top-level controller 2501, each controller functions according to known tasks based on task-specific parameters that are detected and/or derived from the specific module and/or the modular system as a whole. As discussed above, and without limitation, the parameters are, for example, cadence (steps/min), stride time (s), stride length, step width, duration of double support.

With respect to the flexible exosuit controller 2503, a specific task for control is to provide torque at joints (e.g., hip and/or ankle joints) at appropriate points in the gait cycle. This control results in the toddler's gait parameters exhibiting greater stride length and/or narrower step width, which indicate a more mature walking gait. This applied torque can serve an assistive function, particularly in toddlers lacking the muscle strength or control to move their limbs appropriately, or simply can act as an impulse to induce the toddler to step with the correct timing in the gait cycle.

Within the domain of the flexible exosuit controller 2503, control also can be based on a state-machine formulation. The discrete states represent the various phases of the gait cycle of typically developing toddlers, and sensors can determine the transitions between these states. Sensors can detect information with respect to joint angles and/or kinematics via the use of inertial measurement units (IMUs), encoders, and/or hyper-elastic soft strain sensors across joints. IMUs and foot switches can also sense gait events.

When used in conjunction with the support module, the gait information can be used to synchronize the COM motion as modulated by the support module with the toddler's limb motion(s) modulated by the flexible exosuit. The support module can actively guide the COM to follow a typical trajectory of a developed user that is in sync with assisted limb motion provided by the flexible exosuit. By way of example, such control is directed by the support module controller 2505 and the flexible exosuit controller 2503 through force control that impedes incorrect motion while admitting correct motion. Further, measurements from sensors throughout the flexible exosuit (e.g., IMUs) can be combined to provide absolute orientation of multiple limb segments with sufficient accuracy for kinematic estimation. Further, raw angular velocity and acceleration data, combined with accurate a priori estimates of limb moments of inertia, can be used to calculate joint torques and forces.

By way of example, each state of the state-machine formulation within the flexible exosuit controller 2503 includes a relationship between the current state of the flexible exosuit and the toddler's legs and the required torques for the actuation. The relationship can be based on an impedance control. Such assistive actuation provided by the flexible exosuit allows the child to explore the properties of the leg, as an example, in a gravitational field based on the commands from the top-level level controller 2501.

With respect specifically to the mobile base controller 2507, the mobile base may be operated under a passive, a hybrid, or an active state. In a passive state, the mobile base may include no control. The mobile base may include wheels that allow the mobile base to move according to forces applied by the toddler on the mobile base. In a hybrid state, the mobile base may have control only to prevent the mobile base from impacting the toddler. For the hybrid state, the mobile base may include a sensor that detects the proximity of the toddler and relays this information to the mobile base controller 2507. The mobile base may further include a motion sensor, such as an IMU or an accelerometer, to detect whether the mobile base is in motion. Depending on information from these sensors, the mobile base controller 2507 can operate a break to prevent the mobile base from continuing into a toddler in the event that the toddler stops moving forward.

In the active embodiment of the mobile base, the mobile base controller 2507 coordinates the forward motion of the mobile base with the forward motion of the toddler and/or the support module to achieve a forward trajectory of the toddler. As discussed above, given the larger inertia of the cart, small, rapid motions of the COM can be controlled by the support module, and coarse or overall forward speed of the toddler's walk can be matched by the mobile base according to control by the mobile base controller 2507.

In a configuration with the support module included, the support module on the mobile can maintain a minimum distance between the child and the mobile base. However, in cases without the support module (e.g., exosuit only), integrated sensors can detect the distance between the mobile base and the toddler to make sure a safe margin is maintained. Such proximity sensors can include string potentiometers, infrared, and/or ultrasonic sensors. Such sensors can further include the motion sensors discussed above with respect to the hybrid passive state.

The support module controller 2505 can implement various functions. By way of example, the support module can be actuated vertically at certain points in a toddler's gait cycle—based on sensory information acquired from the flexible exosuit—to provide partial unloading of body weight. The support module can additionally, or in the alternative, lock movement in one direction (e.g., anterior-posterior or medial-lateral) while allowing the toddler to freely move and explore in other directions. Additionally, or in the alternative, the support module can lock movement in all but one direction to allow the toddler to freely explore in the one direction without being burdened by stabilization and support within the other directions. The support module can actively guide the toddler's COM to follow a normal trajectory in sync with limb motion. Such guidance can be provided, by way of example, through force control that impedes incorrect motion while admitting correct motion.

In the arm embodiment of the support module, all loads are transmitted through the 6DOF sensor in the arm. This enables the support module controller 2505 and/or the top-level controller 2501 to detect the toddler's balance, and possibly intent. In the scaffold embodiment, the support module controller 2505 can execute a lower level control algorithm that determines the tensions in individual tethers to generate the desired force-moment at the pelvis.

Within the modular system and the six states discussed above, the top-level controller 2501 determines the dynamic configurations required for the support module and the flexible exosuit to assist children in stabilizing medial-lateral and anterior-posterior sway, forward propulsion, and the coordination of body movements. The top-level controller 2501 ensures interoperability of all the modules. The top-level controller 2501 also enables tuning the levels of assistance provided by the modular system depending on the child's ability. The tuning can be performed by a user, such as a physician, clinician, and/or technician analyzing the performance of the toddler, such as within a medical and/or clinical environment, or by one of the toddler's parents and/or guardians, such as within the home environment.

The top-level controller 2501 integrates sensor information obtained from all the different modules. Such sensor information can include COM information and body weight support levels from the support module, joint kinematics and spatial-temporal gait information such as stride time from the flexible exosuit, and overall velocity information from the mobile base. Based on a totality of the available sensory information from the modules, the top-level controller 2501 can determine the gait cycle state of the toddler. According to the gait cycle state of the toddler, the modular system can take action to facilitate progression through the gait cycle. This can occur according several different ways depending on the individual.

By way of example, according to some embodiments, the support module controller 2505 controls stabilization of the medial-lateral and anterior-posterior body sway during the addition of hip and ankle torques via the flexible exosuit. Concurrently, the flexible exosuit controller 2503 adjusts the magnitudes of hip and ankle torques to maintain forward propulsion as the support module and support module controller 2505 stabilize body sway.

By way of another example, according to some embodiments, a more active control approach can be taken. The more active control approach can purposely create imbalance in, for example, the medial-lateral plane to induce a weight-bearing shift and subsequent stepping. This more active control approach of purposeful destabilization is an automated robotic approach that is similar to what adults do when they lift the toddler's hands and pivot the toddler on one foot/leg as the other foot/leg swings in a forward stepping motion.

Integrated within the control of promoting the development of movement, and to enforce the safety of the modular system for the toddler, the top-level controller 2501 can further detect the instability of the toddler and control one or more of the modules accordingly to prevent and/or compensate for the instability. The control and compensation for instability prevents injury of the toddler from, for example, the toddler falling down or impacting an element of the modular system or other obstacle. Thus, in addition to falling, the modular system further monitors for other dangers, such as obstacles and/or abnormal joint motions that can lead to injury.

By way of example, control techniques that prevent and/or compensate for the instability can include the support module applying one or more forces to re-stabilize the toddler or allow the toddler to fall in a controlled manner. Additionally, or in the alternative, a control technique can include the support module going slack to allow the toddler to fall safely. Approaches of detecting instability can include concepts of bipedal walking, such as zero moment point/center of pressure, and biomechanical concepts, such as the inverted "cone of stability."

Based on the modularity of the modular system, according to some embodiments of the present concepts, the top-level controller 2501 determines the presence of the additional modules based on, for example, signals provided by the controllers of the other modules (e.g., heart beat signals). Based on the detected presence of the additional modules, the top-level controller 2501 can automatically and dynamically adjust the control of the modular system. Additionally, or in the alternative, the top-level controller 2501 can receive one or more inputs from a user (e.g., physician, clinician, technician, parent, etc.) that instructs the top-level controller 2501 regarding the modules that are present. Based on the received one or more inputs, the top-level controller 2501 adjusts the control of the modular system.

Accordingly to some exemplary embodiments, a combined approach can be taken. The top-level controller 2501 can automatically detect the present modules. The modules detected by the top-level controller 2501 can then be presented to a user, such as being presented on a graphical user interface, for confirmation of the present modules and/or selective enablement/disablement. According to aspects of the present concepts, indicators (e.g., visual, audio, tactile) on the modules indicate operation (e.g., power indicator), connectivity (e.g., in communication with the other modules), and/or readiness (e.g., sensor initialization) of each module. By way example, one or more LED indicators on the modules can indicate that the modules are powered on and in communication with the top-level controller 2501 and/or one or more controllers of one or more other modules.

Figure 26:
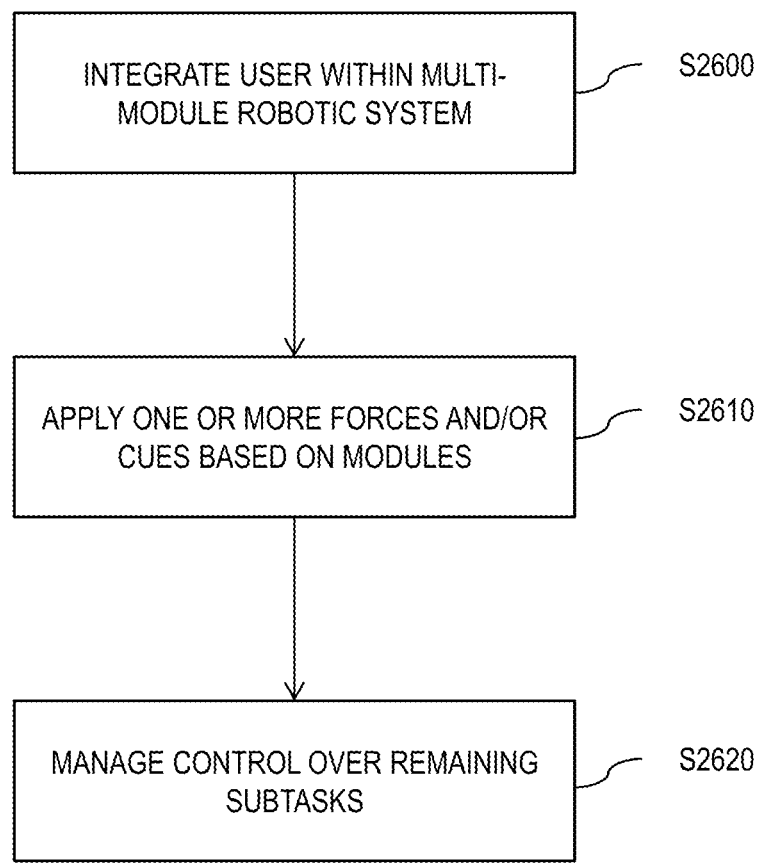
FIG. 26 shows acts in a method according to at least some aspects of the present concepts.

FIG. 26 shows acts in a method according to at least some aspects of the present concepts. The acts of the process shown with respect to FIG. 26 may be practiced in accord with the above disclosure to achieve the following steps. The method of FIG. 26 comprises an act of integrating a user (e.g., a toddler) within a multi-module robotic system (act 2600). The multi-module robotic system may include the above-described modules of a flexible exosuit, a support module, and a mobile base. Alternatively, the system can include the flexible exosuit and at least one of the support module and the mobile base, depending on the requirements of development of the user. The flexible exosuit is worn on the user and configured to modify motion of the user at one or more joint- and/or limb-specific locations. The support module is configured to influence a center-of-mass (COM) of the user. The mobile base provides a structural support for one or more of the flexible exosuit, the support module, and the user.

At act 2610, one or more subtask-specific functions of the modules apply one or more forces, cues, or a combination thereof on the user to cause a developing of one or more subtasks of the walking motion. The forces and/or cues can be any of the above-described forces and/or cues, such as applications of force and/or torque about a joint or to a limb, and stabilization and/or de-stabilization about the medial-lateral and/or anterior-posterior directions.

At act 2620, the modules manage control of one or more remaining subtasks of the walking motion, in place of, at least in part, the user, while applying the one or more forces, cues, or a combination thereof. By the modules managing control of the one or more remaining subtasks of the walking motion, the user is able to develop the one or more subtasks of the walking motion by being able to focus on the one or more subtasks. Acts 2610 and 2620 can be repeated for various different subtasks to develop the user's ability to walk. Thus, in the application of a developmentally-delayed toddler, the toddler can be integrated within the multi-module robotic system and have directed development of various subtasks of walking Each development progresses the toddler towards proper motion to overcome the developmental delay.

Based on the acts of the method of FIG. 26, and by way of example, the modular system can provide body support (e.g., variable anti-gravity unloading) in coordinating the functions that the mobile base and the flexible exosuit perform to assist with the user (e.g., a toddler) generating a normal walking pattern to help the user to train to have a normal walking gait. By way of another example, based on the acts of the method of FIG. 26, and in the case of a stroke victim, the modular system can coordinate functions done in the sub-acute phase of a stroke. From the beginning, the user, such as the stroke victim, is trained by the modular system to have normal movement patterns. Accordingly, the user does not develop bad walking patterns that could be later hard to correct.

It should be understood that any and all combinations and permutations of the features, functions and concepts discussed in detail herein are contemplated as being part of the inventive subject matter (provided such concepts are not explicitly disclaimed or mutually inconsistent). For example, although differing in appearance, the individual systems and devices and functional componentry depicted and discussed herein can each take on any of the various forms, optional configurations, and functional alternatives described above and below with respect to the other disclosed embodiments, unless explicitly disclaimed or otherwise logically prohibited. Also, the technology described herein may be embodied as various methods, of which numerous examples have been provided. The acts performed as part of any method may be ordered in any suitable way. Accordingly, embodiments may be constructed in which acts are performed in an order different than illustrated, even though shown as sequential acts in illustrative embodiments, in which some acts are performed simultaneously, in which some acts are omitted, and/or in which some acts are adopted from other illustrated embodiments.

Each of these embodiments and obvious variations thereof is contemplated as falling within the spirit and scope of the claimed invention, at least some aspects of which are set forth in the following claims. Moreover, the present concepts expressly include any and all combinations and sub combinations of the preceding elements and aspects.

What is claimed:

1. A drive arrangement for generating a torque about a body joint of a person of toddler age or older, the drive arrangement comprising:
    a power unit, a force transmission element, a drive unit, and a flexible shaft;
    wherein the force transmission element is operably connected to both the power unit and the drive unit so as to transmit a force from the power unit to the drive unit;
    wherein the drive unit is operably connected to a proximal portion of the flexible shaft and is configured to convert the force transmitted by the force transmission element into a torque for rotating the flexible shaft;
    wherein the power unit is configured to:
        (a) place the drive arrangement into an actuated state for rotating the flexible shaft, by retracting the force transmission element to either engage the drive unit or cause the drive unit to engage the flexible shaft; and
        (b) place the drive arrangement into a non-actuated state for allowing rotation of the flexible shaft without any impedance from the force transmission element, by feeding out the force transmission element to either disengage from the drive unit or cause the drive unit to disengage from the flexible shaft; and
    wherein a distal end of the flexible shaft is configured to be coupled to a body part of the person such that the drive arrangement applies a rotational torque to the body joint when the drive arrangement is in the actuated state.

2. The drive arrangement of claim 1 wherein the force transmission element is a cable.

3. The drive arrangement of claim 2,
    wherein the cable comprises a cable stop, the drive unit comprises a loop, and the cable is disposed within the loop, wherein, in the actuated state, retracting the cable causes the cable stop to engage the loop, and wherein, in the non-actuated state, feeding out the cable allows the cable stop to disengage from the loop.

4. The drive arrangement of claim 3 further comprising a spring connected to the cable stop to provide a return force and maintain tension in the force transmission element in the non-actuated state.

5. The drive arrangement of claim 2 wherein:

the drive unit comprises a peg and a pulley, the peg being fixedly attached to the pulley;

the cable is attached to the pulley;

the pulley is rotatable about a center of rotation of the flexible shaft;

the peg is located away from a center of rotation of the flexible shaft; and in the actuated state, retracting the cable causes the peg to engage the proximal portion of the flexible shaft, and in the non-actuated state, feeding out the cable allows the peg to disengage from the proximal portion of the flexible shaft.

6. The drive arrangement of claim 5 wherein the drive unit further comprises a torsional spring disposed so as to urge the pulley toward a predetermined resting position.

7. The drive arrangement of claim 1 further comprising a force sensor capable of detecting force or torque applied to the flexible shaft.

8. The drive arrangement of claim 2 further comprising a sensor capable of measuring the tension in the cable.

9. The drive arrangement of claim 1 further comprising an encoder capable of detecting the relative angular position of the flexible shaft with respect to the drive unit.

10. The drive arrangement of claim 1 wherein the drive unit is configured to be affixed to the person and to resist counter-torque generated by the drive arrangement in the actuated state.

11. The drive arrangement of claim 10 wherein the drive unit includes a support plate for affixing to the person.

12. The drive arrangement of claim 1 wherein the drive unit is operably connected to the proximal portion of the flexible shaft by a prismatic joint.

13. The drive arrangement of claim 1 wherein the flexible shaft comprises a prismatic joint between its proximal and distal portions.

14. The drive arrangement of claim 1 wherein the body joint is a hip joint of the person and wherein the body part is a thigh of the person.

15. The drive arrangement of claim 14 wherein the distal portion of the flexible shaft is branched for more even and more comfortable force distribution along the thigh of the person.

16. The drive arrangement of claim 15 further including a thigh attachment configured to spread and dissipate the applied force from the flexible shaft.

17. The drive arrangement of claim 1 wherein the rotational torque generated about the body joint provides at least one of motion assistance, motion resistance, and a cue to the wearer.

* * * * *